US010610508B2

(12) United States Patent
Manku et al.

(10) Patent No.: US 10,610,508 B2
(45) Date of Patent: *Apr. 7, 2020

(54) METHODS OF REDUCING APOLIPOPROTEIN C-III

(71) Applicant: Amarin Pharmaceuticals Ireland Limited, Dublin (IE)

(72) Inventors: Mehar Manku, Birmingham (GB); Ian Osterloh, Kent (GB); Pierre Wicker, Mystic, CT (US); Rene Braeckman, Richboro, PA (US); Paresh Soni, Mystic, CT (US); Joseph S. Zakrzewski, Bedminster, NJ (US)

(73) Assignee: Amarin Pharmaceuticals Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/191,204

(22) Filed: Nov. 14, 2018

(65) Prior Publication Data

US 2019/0076390 A1 Mar. 14, 2019

Related U.S. Application Data

(63) Continuation of application No. 14/261,160, filed on Apr. 24, 2014, now Pat. No. 10,265,290, which is a continuation-in-part of application No. 14/173,155, filed on Feb. 5, 2014, now Pat. No. 9,452,151.

(51) Int. Cl.
| | |
|---|---|
| *A61K 31/232* | (2006.01) |
| *A61K 31/23* | (2006.01) |
| *A61P 3/00* | (2006.01) |
| *A61P 43/00* | (2006.01) |
| *A61P 3/06* | (2006.01) |

(52) U.S. Cl.
CPC ............ *A61K 31/232* (2013.01); *A61K 31/23* (2013.01); *A61P 3/00* (2018.01); *A61P 3/06* (2018.01); *A61P 43/00* (2018.01)

(58) Field of Classification Search
CPC ......... A61K 31/232; A61K 31/23; A61P 3/00; A61P 3/06; A61P 43/00
See application file for complete search history.

(56) References Cited

U.S. PATENT DOCUMENTS

| | | |
|---|---|---|
| 4,377,526 A | 3/1983 | Fujita et al. |
| 4,526,902 A | 7/1985 | Rubin |
| 4,920,098 A | 4/1990 | Cotter et al. |
| 4,935,243 A | 6/1990 | Borkan et al. |
| 5,013,443 A | 5/1991 | Higashidate et al. |
| 5,116,871 A | 5/1992 | Horrobin et al. |
| 5,178,873 A | 1/1993 | Horrobin et al. |
| 5,198,468 A | 3/1993 | Horrobin |
| 5,215,630 A | 6/1993 | Hata et al. |
| 5,252,333 A | 10/1993 | Horrobin |
| 5,343,389 A | 8/1994 | Otvos |
| 5,385,929 A | 1/1995 | Bjorge et al. |
| 5,457,130 A | 10/1995 | Tisdale et al. |
| 5,502,077 A | 3/1996 | Breivik et al. |
| 5,567,730 A | 10/1996 | Miyashita et al. |
| 5,589,508 A | 12/1996 | Schlotzer et al. |
| 5,603,959 A | 2/1997 | Horrobin et al. |
| 5,618,558 A | 4/1997 | Horrobin et al. |
| 5,656,667 A | 8/1997 | Breivik et al. |
| 5,698,594 A | 12/1997 | Breivik et al. |
| 5,760,081 A | 6/1998 | Leaf et al. |
| 5,763,496 A | 6/1998 | Holland |
| 5,776,978 A | 7/1998 | Bruzzese |
| 5,792,795 A | 8/1998 | Buser et al. |
| 5,837,731 A | 11/1998 | Vaddadi |
| 5,840,944 A | 11/1998 | Furihata et al. |
| 5,886,037 A | 3/1999 | Klor et al. |
| 5,888,541 A | 3/1999 | Horrobin et al. |
| 5,948,818 A | 9/1999 | Buser et al. |
| 6,025,008 A | 2/2000 | Akahoshi |
| 6,069,168 A | 5/2000 | Horrobin et al. |
| 6,193,999 B1 | 2/2001 | Gennadios |
| 6,284,268 B1 | 9/2001 | Mishra et al. |
| 6,313,330 B1 | 11/2001 | Kiyohara et al. |
| 6,326,031 B1 | 12/2001 | Hsia et al. |
| 6,326,355 B1 | 12/2001 | Abbruzzese et al. |
| 6,331,568 B1 | 12/2001 | Horrobin |
| 6,368,621 B1 | 4/2002 | Engel et al. |
| 6,384,077 B1 | 5/2002 | Peet |
| 6,479,544 B1 | 11/2002 | Horrobin |

(Continued)

FOREIGN PATENT DOCUMENTS

| | | |
|---|---|---|
| CA | 2628305 | 5/2007 |
| CA | 2653787 | 12/2007 |

(Continued)

OTHER PUBLICATIONS

A study of AMR101 to evaluate its ability to reduce cardiovascular events in high risk patients with hypertriglyceridemia and on statin (REDUCE-IT). Available at: http://clinicaltrials.gov/show/NCT01492361. (3 pages).

Aarsland, et al., "On the Effect of Peroximsomal beta-Oxidation and Carnitine Palmitoyltransferase Activity by Eicosapentaenoic Aid in Live and Heart of Rats." Lipids, 25:546-548, (Sep. 1990).

Aas, V., et al., "Eicosapentaenoic acid (20:5 n-3) increases fatty acid and glucose uptake in cultured human skeletal muscle cells." Journal of Lipid Research, 47:366-374 (Feb. 2006).

Abbey, M., et al., "Effect of fish oil on lipoproteins, lecithin:cholesterol acyltransferase, and lipidtransfer protein activity in humans." Arterioscler. Thromb. Vasc. Biol. 10:85-94 (Jan./Feb. 1990).

Abele GS, Aziz K. "Cholesterol crystals cause mechanical damage to biological membranes: a proposed mechanism of plaque rupture and erosion leading to arterial thrombosis." Clin. Cardiol. (Sep. 2005);28(9):413-420.

(Continued)

*Primary Examiner* — My-Chau T. Tran

(57) ABSTRACT

In various embodiments, the present invention provides methods of treating and/or preventing cardiovascular-related disease and, in particular, a method of blood lipid therapy comprising administering to a subject in need thereof a pharmaceutical composition comprising eicosapentaenoic acid or a derivative thereof.

20 Claims, 2 Drawing Sheets

(56) References Cited

U.S. PATENT DOCUMENTS

| | | |
|---|---|---|
| 6,482,421 B2 | 11/2002 | Weidner |
| 6,531,150 B1 | 3/2003 | Sunohara et al. |
| 6,555,700 B1 | 4/2003 | Horrobin et al. |
| 6,596,766 B1 | 7/2003 | Igarashi et al. |
| 6,620,821 B2 | 9/2003 | Robl |
| 6,689,812 B2 | 2/2004 | Peet |
| 6,846,942 B2 | 1/2005 | Rubin |
| 7,022,713 B2 | 4/2006 | Aoki et al. |
| 7,112,609 B2 | 9/2006 | Hermelin et al. |
| 7,119,118 B2 | 10/2006 | Peet |
| 7,179,491 B1 | 2/2007 | Mag |
| 7,205,329 B2 | 4/2007 | Chien et al. |
| 7,405,302 B2 | 7/2008 | Hutchinson et al. |
| 7,498,359 B2 | 3/2009 | Yokoyama et al. |
| 7,511,131 B2 | 3/2009 | Crooke et al. |
| 7,598,227 B2 | 10/2009 | Crooke et al. |
| 7,776,881 B2 | 8/2010 | Aoki et al. |
| 8,188,146 B2 | 5/2012 | Peet et al. |
| 8,293,727 B2 | 10/2012 | Manku et al. |
| 8,293,728 B2 | 10/2012 | Manku et al. |
| 8,298,554 B2 | 10/2012 | Manku |
| 8,314,086 B2 | 11/2012 | Manku et al. |
| 8,318,715 B2 | 11/2012 | Manku et al. |
| 8,324,195 B2 | 12/2012 | Manku et al. |
| 8,357,677 B1 | 1/2013 | Manku et al. |
| 8,367,652 B2 | 2/2013 | Manku et al. |
| 8,377,920 B2 | 2/2013 | Manku et al. |
| 8,410,086 B2 | 4/2013 | Osterloh et al. |
| 8,431,560 B1 | 4/2013 | Manku et al. |
| 8,440,650 B1 | 5/2013 | Manku et al. |
| 8,455,472 B2 | 6/2013 | Osterloh et al. |
| 8,518,929 B2 | 8/2013 | Manku et al. |
| 8,524,698 B2 | 9/2013 | Manku et al. |
| 8,546,372 B2 | 10/2013 | Manku et al. |
| 8,551,521 B2 | 10/2013 | Manku et al. |
| 8,563,608 B2 | 10/2013 | Manku et al. |
| 8,617,593 B2 | 12/2013 | Manku et al. |
| 8,617,594 B2 | 12/2013 | Manku et al. |
| 8,618,168 B2 | 12/2013 | Fujii et al. |
| 8,623,406 B2 | 1/2014 | Manku et al. |
| 8,642,077 B2 | 2/2014 | Manku et al. |
| 8,669,245 B2 | 3/2014 | Osterloh et al. |
| 8,680,144 B2 | 3/2014 | Osterloh et al. |
| 8,691,871 B2 | 4/2014 | Osterloh et al. |
| 8,703,185 B2 | 4/2014 | Manku et al. |
| 8,709,475 B2 | 4/2014 | Manku et al. |
| 8,906,964 B2 | 12/2014 | Bobotas et al. |
| 9,006,285 B2 | 4/2015 | Ohnishi |
| 9,056,088 B2 * | 6/2015 | Osterloh .............. A61K 31/202 |
| 9,060,981 B2 | 6/2015 | Sato et al. |
| 9,138,415 B2 | 9/2015 | Manku et al. |
| 9,452,121 B2 | 9/2016 | Manku et al. |
| 9,452,150 B2 | 9/2016 | Ueshima et al. |
| 9,452,151 B2 * | 9/2016 | Manku .................. A61K 31/232 |
| 9,603,826 B2 | 3/2017 | Soni |
| 9,610,272 B2 | 4/2017 | Soni |
| 9,623,001 B2 | 4/2017 | Soni |
| 9,693,984 B2 | 7/2017 | Soni |
| 9,693,985 B2 | 7/2017 | Soni |
| 9,693,986 B2 | 7/2017 | Soni |
| 9,827,219 B2 * | 11/2017 | Manku .................. A61K 31/232 |
| 9,855,237 B2 | 1/2018 | Osterloh et al. |
| 9,918,954 B2 | 3/2018 | Soni |
| 10,058,521 B2 * | 8/2018 | Bobotas ............... A61K 31/202 |
| 10,166,209 B2 * | 1/2019 | Manku .................. A61K 31/232 |
| 10,265,290 B2 * | 4/2019 | Manku .................. A61K 31/232 |
| 2001/0035125 A1 | 11/2001 | Talieh et al. |
| 2002/0016312 A1 | 2/2002 | Seed et al. |
| 2002/0025983 A1 | 2/2002 | Horrobin |
| 2002/0035125 A1 | 3/2002 | Shear |
| 2002/0055529 A1 | 5/2002 | Bisgaier et al. |
| 2002/0055539 A1 | 5/2002 | Bockow et al. |
| 2002/0077361 A1 | 6/2002 | Peet et al. |
| 2002/0169209 A1 | 11/2002 | Horrobin |
| 2002/0183389 A1 | 12/2002 | Peet |
| 2002/0193439 A1 | 12/2002 | Peet et al. |
| 2002/0198177 A1 | 12/2002 | Horrobin et al. |
| 2003/0100610 A1 | 5/2003 | Shibuya |
| 2003/0104048 A1 | 6/2003 | Patel et al. |
| 2003/0161918 A1 | 8/2003 | Kendrick et al. |
| 2003/0166614 A1 | 9/2003 | Harrison |
| 2003/0232385 A1 | 12/2003 | Breit et al. |
| 2004/0009208 A1 | 1/2004 | Edson |
| 2004/0048919 A1 | 3/2004 | Dreon et al. |
| 2004/0062847 A1 | 4/2004 | Koiki et al. |
| 2004/0077723 A1 | 4/2004 | Granata |
| 2004/0106591 A1 | 6/2004 | Pacioretty et al. |
| 2004/0121000 A1 | 6/2004 | Bowe et al. |
| 2004/0162348 A1 | 8/2004 | Peet et al. |
| 2004/0082402 A1 | 9/2004 | Troup et al. |
| 2004/0204356 A1 | 10/2004 | Guenzler-Pukall |
| 2004/0258645 A1 | 12/2004 | Trejo et al. |
| 2005/0042214 A1 | 2/2005 | Gershwin et al. |
| 2005/0137253 A1 | 6/2005 | Phinney et al. |
| 2005/0147665 A1 | 7/2005 | Horrobin et al. |
| 2005/0187292 A1 | 8/2005 | Aoki et al. |
| 2005/0244367 A1 | 11/2005 | Hui et al. |
| 2005/0272095 A1 | 12/2005 | Wang |
| 2006/0034815 A1 | 2/2006 | Guzman et al. |
| 2006/0051418 A1 | 3/2006 | Cowen et al. |
| 2006/0088502 A1 | 4/2006 | Sata et al. |
| 2006/0111437 A1 | 5/2006 | Aoki et al. |
| 2006/0134178 A1 | 6/2006 | Doisaki et al. |
| 2006/0134206 A1 | 6/2006 | Iyer et al. |
| 2006/0135607 A1 | 6/2006 | Kobayashi et al. |
| 2006/0135610 A1 | 6/2006 | Bortz et al. |
| 2006/0141022 A1 | 6/2006 | Kawamura et al. |
| 2006/0142390 A1 | 6/2006 | Manku et al. |
| 2006/0172012 A1 | 8/2006 | Finley et al. |
| 2006/0189682 A1 | 8/2006 | Payne et al. |
| 2006/0211749 A1 | 9/2006 | Bobotas et al. |
| 2006/0211761 A1 | 9/2006 | Kumar et al. |
| 2006/0211762 A1 | 9/2006 | Rongen |
| 2006/0211763 A1 | 9/2006 | Fawzy et al. |
| 2006/0217356 A1 | 9/2006 | Wright et al. |
| 2006/0223838 A1 | 10/2006 | Jiang |
| 2006/0252833 A1 | 11/2006 | Peet et al. |
| 2007/0021504 A1 | 1/2007 | Yokoyama et al. |
| 2007/0060532 A1 | 3/2007 | Junien et al. |
| 2007/0098787 A1 | 5/2007 | Kakiuchi |
| 2007/0104779 A1 | 5/2007 | Rongen et al. |
| 2007/0105793 A1 | 5/2007 | Hendrix |
| 2007/0105954 A1 | 5/2007 | Puri |
| 2007/0141138 A1 | 6/2007 | Feuerstein et al. |
| 2007/0167520 A1 | 7/2007 | Bruzzese |
| 2007/0185198 A1 | 8/2007 | Yokoyama et al. |
| 2007/0191467 A1 | 8/2007 | Rongen et al. |
| 2007/0202159 A1 | 8/2007 | Mathur et al. |
| 2007/0212411 A1 | 9/2007 | Fawzy et al. |
| 2007/0219271 A1 | 9/2007 | Mittmann et al. |
| 2007/0265340 A1 | 11/2007 | Shalwitz et al. |
| 2007/0269507 A1 | 11/2007 | Sachetto et al. |
| 2008/0020018 A1 | 1/2008 | Moodley et al. |
| 2008/0057115 A1 | 3/2008 | Okamoto |
| 2008/0085911 A1 | 4/2008 | Rongen et al. |
| 2008/0089876 A1 | 4/2008 | Cavazza |
| 2008/0113046 A1 | 5/2008 | Gardette |
| 2008/0125490 A1 | 5/2008 | Svensson et al. |
| 2008/0185198 A1 | 8/2008 | Jones |
| 2008/0200453 A1 | 8/2008 | Cincotta |
| 2008/0200547 A1 | 8/2008 | Peet et al. |
| 2008/0200707 A1 | 8/2008 | Shimano et al. |
| 2008/0299187 A1 | 12/2008 | Opheim et al. |
| 2008/0306154 A1 | 12/2008 | Svensson et al. |
| 2008/0319077 A1 | 12/2008 | Suzuki et al. |
| 2009/0012167 A1 | 1/2009 | Rongen et al. |
| 2009/0018125 A1 | 1/2009 | Mittmann et al. |
| 2009/0042979 A1 | 2/2009 | Guzman et al. |
| 2009/0054329 A1 | 2/2009 | Willemsen et al. |
| 2009/0105340 A1 | 4/2009 | Yokoyama |
| 2009/0156675 A1 | 6/2009 | Yokoyama et al. |
| 2009/0182049 A1 | 7/2009 | Opheim |
| 2009/0227602 A1 | 9/2009 | Griffin et al. |
| 2009/0233843 A1 | 9/2009 | Marin |

(56) References Cited

U.S. PATENT DOCUMENTS

| | | |
|---|---|---|
| 2009/0239927 A1 | 9/2009 | Bobotas et al. |
| 2009/0304784 A1 | 12/2009 | Mane et al. |
| 2009/0311322 A1 | 12/2009 | Dlugatch et al. |
| 2010/0021555 A1 | 1/2010 | Geiringer et al. |
| 2010/0063018 A1 | 3/2010 | Pellicciari et al. |
| 2010/0069492 A1 | 3/2010 | Geiringen et al. |
| 2010/0113506 A1 | 5/2010 | Kawano et al. |
| 2010/0113811 A1 | 5/2010 | Yadav et al. |
| 2010/0119598 A1 | 5/2010 | Yoshinari et al. |
| 2010/0130608 A1 | 5/2010 | Ryan et al. |
| 2010/0160261 A1 | 6/2010 | Fortin |
| 2010/0233280 A1 | 9/2010 | Driscoll |
| 2010/0254951 A1 | 10/2010 | Shido et al. |
| 2010/0278879 A1 | 11/2010 | Manku |
| 2010/0285121 A1 | 11/2010 | Uchiyama et al. |
| 2010/0298379 A1 | 11/2010 | Jacobsen |
| 2010/0305205 A1 | 12/2010 | Yokoyama et al. |
| 2010/0311834 A1 | 12/2010 | Manku et al. |
| 2011/0034555 A1 | 2/2011 | Osterloh et al. |
| 2011/0065793 A1 | 3/2011 | Peet et al. |
| 2011/0071176 A1 | 3/2011 | Rowe |
| 2011/0082119 A1 | 4/2011 | Yano |
| 2011/0092592 A1 | 4/2011 | Yano |
| 2011/0105510 A1 | 5/2011 | Ishikawa |
| 2011/0130458 A1 | 6/2011 | Breivik et al. |
| 2011/0178105 A1 | 7/2011 | Gillies et al. |
| 2011/0195061 A1 | 8/2011 | Minatelli |
| 2011/0218243 A1 | 9/2011 | Rowe |
| 2011/0223158 A1 | 9/2011 | Sacks et al. |
| 2011/0236476 A1 | 9/2011 | Manku |
| 2011/0268811 A1 | 11/2011 | Minatelli et al. |
| 2011/0288171 A1 | 11/2011 | Manku et al. |
| 2012/0035105 A1 | 2/2012 | Geho et al. |
| 2012/0035262 A1 | 2/2012 | Osterloh et al. |
| 2012/0039997 A1 | 2/2012 | Manku et al. |
| 2012/0093922 A1 | 4/2012 | Manku et al. |
| 2012/0093924 A1 | 4/2012 | Manku et al. |
| 2012/0100208 A1 | 4/2012 | Manku |
| 2012/0108659 A1 | 5/2012 | Manku et al. |
| 2012/0108660 A1 | 5/2012 | Manku et al. |
| 2012/0108663 A1 | 5/2012 | Manku et al. |
| 2012/0121698 A1 | 5/2012 | Manku et al. |
| 2012/0156285 A1 | 6/2012 | Manku et al. |
| 2012/0157530 A1 | 6/2012 | Manku et al. |
| 2012/0157531 A1 | 6/2012 | Osterloh et al. |
| 2012/0172432 A1 | 7/2012 | Manku et al. |
| 2012/0184595 A1 | 7/2012 | Macdonald et al. |
| 2012/0195963 A1 | 8/2012 | Peet et al. |
| 2012/0207800 A1 | 8/2012 | Abu-Baker |
| 2012/0214771 A1 | 8/2012 | Sampalis |
| 2012/0225120 A1 | 9/2012 | Manku et al. |
| 2012/0232145 A1 | 9/2012 | Osterloh et al. |
| 2012/0237594 A1 | 9/2012 | Manku et al. |
| 2012/0264824 A1 | 10/2012 | Mizuguchi et al. |
| 2012/0295976 A1 | 11/2012 | Yokoyama |
| 2012/0302589 A1 | 11/2012 | Manku et al. |
| 2012/0329852 A1 | 12/2012 | Yokoyama |
| 2013/0004566 A1 | 1/2013 | Manku et al. |
| 2013/0004567 A1 | 1/2013 | Manku et al. |
| 2013/0004568 A1 | 1/2013 | Manku et al. |
| 2013/0004572 A1 | 1/2013 | Manku et al. |
| 2013/0005757 A1 | 1/2013 | Osterloh et al. |
| 2013/0005809 A1 | 1/2013 | Manku et al. |
| 2013/0011471 A1 | 1/2013 | Manku et al. |
| 2013/0011472 A1 | 1/2013 | Manku et al. |
| 2013/0012580 A1 | 1/2013 | Osterloh et al. |
| 2013/0017256 A1 | 1/2013 | Manku et al. |
| 2013/0065956 A1 | 3/2013 | Yokoyama |
| 2013/0079409 A1 | 3/2013 | Manku et al. |
| 2013/0090383 A1 | 4/2013 | Manku et al. |
| 2013/0095178 A1 | 4/2013 | Manku |
| 2013/0095179 A1 | 4/2013 | Davidson et al. |
| 2013/0096197 A1 | 4/2013 | Manku |
| 2013/0102674 A1 | 4/2013 | Manku |
| 2013/0115284 A1 | 5/2013 | Fujii |
| 2013/0131170 A1 | 5/2013 | Manku |
| 2013/0156852 A1 | 6/2013 | Manku et al. |
| 2013/0158120 A1 | 6/2013 | Manku et al. |
| 2013/0164375 A1 | 6/2013 | Manku et al. |
| 2013/0165513 A1 | 6/2013 | Manku et al. |
| 2013/0171249 A1 | 7/2013 | Manku et al. |
| 2013/0171250 A1 | 7/2013 | Manku et al. |
| 2013/0171251 A1 | 7/2013 | Manku et al. |
| 2013/0172413 A1 | 7/2013 | Manku |
| 2013/0189355 A1 | 7/2013 | Manku et al. |
| 2013/0195972 A1 | 8/2013 | Manku et al. |
| 2013/0252989 A1 | 9/2013 | Manku et al. |
| 2013/0252990 A1 | 9/2013 | Manku et al. |
| 2013/0253030 A1 | 9/2013 | Osterloh et al. |
| 2013/0253031 A1 | 9/2013 | Osterloh et al. |
| 2013/0260403 A1 | 10/2013 | Button et al. |
| 2013/0281534 A1 | 10/2013 | Osterloh et al. |
| 2013/0295173 A1 | 11/2013 | Machielse et al. |
| 2013/0324607 A1 | 12/2013 | Mason |
| 2013/0331447 A1 | 12/2013 | Manku et al. |
| 2014/0004183 A1 | 1/2014 | Soni et al. |
| 2014/0005264 A1 | 1/2014 | Soni et al. |
| 2014/0005265 A1 | 1/2014 | Soni et al. |
| 2014/0017306 A1 | 1/2014 | Manku |
| 2014/0057981 A1 | 2/2014 | Fujii |
| 2014/0073692 A1 | 3/2014 | Peet |
| 2014/0080850 A1 | 3/2014 | Mason |
| 2014/0080909 A1 | 3/2014 | Manku |
| 2014/0088194 A1 | 3/2014 | Manku |
| 2014/0094520 A1 | 4/2014 | Bobotas et al. |
| 2014/0107199 A1 | 4/2014 | Fawzy et al. |
| 2014/0127289 A1 | 5/2014 | Osterloh et al. |
| 2014/0128453 A1 | 5/2014 | Mullick et al. |
| 2014/0128464 A1 | 5/2014 | Rowe |
| 2014/0154310 A1 | 6/2014 | Osterloh et al. |
| 2014/0155455 A1 | 6/2014 | Osterloh et al. |
| 2014/0155481 A1 | 6/2014 | Osterloh et al. |
| 2014/0186438 A1 | 7/2014 | Manku et al. |
| 2014/0187633 A1 | 7/2014 | Manku et al. |
| 2014/0213648 A1 | 7/2014 | Manku et al. |
| 2014/0221358 A1 | 8/2014 | Zakrzewski |
| 2014/0221452 A1 | 8/2014 | Zakrzewski |
| 2014/0221486 A1 | 8/2014 | Manku et al. |
| 2014/0221676 A1 | 8/2014 | Braeckman et al. |
| 2014/0234410 A1 | 8/2014 | Moodley et al. |
| 2014/0235716 A1 | 8/2014 | Manku et al. |
| 2014/0243389 A1 | 8/2014 | Zakrzewski |
| 2014/0249200 A1 | 9/2014 | Braeckman et al. |
| 2014/0249214 A1 | 9/2014 | Braeckman et al. |
| 2014/0249220 A1 | 9/2014 | Braeckman et al. |
| 2014/0249225 A1 | 9/2014 | Mason |
| 2014/0256809 A1 | 9/2014 | Zakrzewski |
| 2014/0271841 A1 | 9/2014 | Grandolfi |
| 2014/0271907 A1 | 9/2014 | Zakrzewski |
| 2014/0275252 A1 | 9/2014 | Zakrzewski |
| 2014/0275253 A1 | 9/2014 | Zakrzewski |
| 2014/0357717 A1 | 12/2014 | Braeckman et al. |
| 2014/0364459 A1 | 12/2014 | Zakrzewski |
| 2015/0045431 A1 | 2/2015 | Zakrzewski |
| 2015/0051143 A1 | 2/2015 | Harada et al. |
| 2015/0051282 A1 | 2/2015 | Zakrzewski |
| 2015/0065572 A1 | 3/2015 | Zakrzewski |
| 2015/0073050 A1 | 3/2015 | Zakrzewski |
| 2015/0141510 A1 | 5/2015 | Kiyohara et al. |
| 2015/0157592 A1 | 6/2015 | Soni |
| 2015/0157593 A1 | 6/2015 | Braeckman et al. |
| 2015/0164850 A1 | 6/2015 | Osterloh et al. |
| 2015/0190361 A1 | 7/2015 | Osterloh et al. |
| 2015/0216831 A1 | 8/2015 | Manku et al. |
| 2015/0250754 A1 | 9/2015 | Ohta |
| 2015/0250756 A1 | 9/2015 | Mason |
| 2015/0250757 A1 | 9/2015 | Soni |
| 2015/0258051 A1 | 9/2015 | Manku et al. |
| 2015/0265566 A1 | 9/2015 | Osterloh et al. |
| 2015/0265574 A1 | 9/2015 | Rowe |
| 2015/0272917 A1 | 10/2015 | Manku et al. |
| 2015/0283074 A1 | 10/2015 | Fujii |
| 2015/0290154 A1 | 10/2015 | Roberts et al. |
| 2015/0335607 A1 | 11/2015 | Rowe |

(56) References Cited

U.S. PATENT DOCUMENTS

| | | |
|---|---|---|
| 2015/0359775 A1 | 12/2015 | Osterloh et al. |
| 2016/0058729 A1 | 3/2016 | Manku et al. |
| 2016/0120837 A1 | 5/2016 | Manku et al. |
| 2016/0143875 A1 | 5/2016 | Zakrzewski |
| 2016/0151319 A1 | 6/2016 | Kimura |
| 2016/0158184 A1 | 6/2016 | Ito |
| 2016/0213636 A1 | 7/2016 | Manku et al. |
| 2016/0213639 A1 | 7/2016 | Suzuki et al. |
| 2016/0220522 A1 | 8/2016 | Osterloh et al. |
| 2016/0287546 A1 | 10/2016 | Osterloh et al. |
| 2017/0014366 A1 | 1/2017 | Osterloh et al. |
| 2017/0035722 A1 | 2/2017 | Soni |
| 2017/0056361 A1 | 3/2017 | Soni |
| 2017/0079946 A1 | 3/2017 | Ohta |
| 2017/0087111 A1 | 3/2017 | Mason |
| 2017/0100363 A9 | 4/2017 | Zakrzewski |
| 2017/0119721 A1 | 5/2017 | Zakrzewski |
| 2017/0119722 A1 | 5/2017 | Manku et al. |
| 2017/0119723 A1 | 5/2017 | Soni |
| 2017/0119724 A1 | 5/2017 | Fujii |
| 2017/0128402 A1 | 5/2017 | Manku et al. |
| 2017/0128405 A1 | 5/2017 | Osterloh et al. |
| 2017/0128406 A1 | 5/2017 | Rowe |
| 2017/0136055 A1 | 5/2017 | Zakrzewski |
| 2017/0143656 A1 | 5/2017 | Soni |
| 2017/0143657 A1 | 5/2017 | Braeckman et al. |
| 2017/0143658 A1 | 5/2017 | Soni |
| 2017/0151202 A1 | 6/2017 | Mason |
| 2017/0151206 A1 | 6/2017 | Yokoyama |
| 2017/0258753 A1 | 9/2017 | Soni |
| 2017/0258754 A1 | 9/2017 | Soni |
| 2017/0258755 A1 | 9/2017 | Soni |
| 2017/0273928 A1 | 9/2017 | Yokoyama |
| 2017/0304249 A1 | 10/2017 | Abu-Baker |
| 2017/0333377 A1 | 11/2017 | Mason |
| 2017/0348268 A1 | 12/2017 | Kimura |
| 2017/0348273 A1 | 12/2017 | Ito |
| 2017/0368184 A1 | 12/2017 | Ito |
| 2018/0015038 A1 | 1/2018 | Ito |
| 2018/0015071 A1 | 1/2018 | Braeckman et al. |
| 2018/0028480 A1 | 2/2018 | Mason |
| 2018/0042880 A1 | 2/2018 | Osterloh et al. |
| 2018/0042883 A1 | 2/2018 | Manku et al. |
| 2018/0064676 A1 | 3/2018 | Zakrzewski |
| 2018/0085334 A1 | 3/2018 | Soni |
| 2018/0153846 A1 | 6/2018 | Soni |
| 2018/0185320 A1 | 7/2018 | Manku et al. |

FOREIGN PATENT DOCUMENTS

| | | |
|---|---|---|
| CA | 2675836 | 7/2008 |
| CA | 2724983 | 11/2009 |
| CA | 2772378 | 12/2010 |
| CN | 101252837 | 8/2008 |
| EP | 273708 | 7/1988 |
| EP | 277747 | 8/1988 |
| EP | 0302482 | 2/1989 |
| EP | 347509 | 12/1989 |
| EP | 0460917 | 12/1991 |
| EP | 606012 | 7/1994 |
| EP | 0610506 | 8/1994 |
| EP | 0641562 A1 | 3/1995 |
| EP | 0843972 | 5/1998 |
| EP | 1125914 | 8/2001 |
| EP | 1157692 | 11/2001 |
| EP | 1296670 | 4/2003 |
| EP | 1549299 | 12/2003 |
| EP | 1743644 | 1/2007 |
| EP | 1 790 339 A1 | 5/2007 |
| EP | 1 834 639 A1 | 9/2007 |
| EP | 1 982 710 A1 | 10/2008 |
| EP | 2022495 | 2/2009 |
| EP | 2395991 | 8/2010 |
| EP | 2308493 A1 | 4/2011 |
| EP | 2343066 A1 | 7/2011 |
| EP | 2719382 A1 | 4/2014 |
| EP | 2792746 | 10/2014 |
| FR | 2635263 | 2/1990 |
| GB | 2148713 | 6/1985 |
| GB | 2221843 | 2/1990 |
| GB | 2229363 | 9/1990 |
| GB | 9901809.5 | 1/1999 |
| GB | 2480146 | 11/2011 |
| IL | 55227 | 12/1982 |
| JP | 61035356 | 2/1986 |
| JP | 04 182426 | 6/1992 |
| JP | 2003306690 | 10/2003 |
| JP | 07 238598 | 9/2007 |
| JP | 08 050367 | 3/2008 |
| KR | 10-2006-0109988 | 10/2006 |
| KR | 10-2007-0058460 | 6/2007 |
| RU | 2290185 | 12/2006 |
| RU | 2402326 C1 | 10/2010 |
| WO | WO 1990/004391 | 5/1990 |
| WO | WO 1992/021335 | 12/1992 |
| WO | WO 1994/028891 | 12/1994 |
| WO | WO 1995/024459 | 9/1995 |
| WO | WO 1996/036329 | 11/1996 |
| WO | WO 1997/039759 | 10/1997 |
| WO | WO 1998/016216 | 4/1998 |
| WO | WO 1999/26583 | 6/1999 |
| WO | WO 1999/029316 | 6/1999 |
| WO | WO 2000/044361 | 8/2000 |
| WO | WO 2000/051573 | 9/2000 |
| WO | WO 2001/015552 | 3/2001 |
| WO | WO 2002/002105 | 1/2002 |
| WO | WO 2002/058793 | 8/2002 |
| WO | WO 2002/089787 | 11/2002 |
| WO | WO 2002/096408 | 12/2002 |
| WO | WO 2003/068216 | 8/2003 |
| WO | WO 2003/092673 | 11/2003 |
| WO | WO 2004/050913 | 6/2004 |
| WO | WO 2004/064716 | 8/2004 |
| WO | WO 2004/078166 | 9/2004 |
| WO | WO 2004/082402 | 9/2004 |
| WO | WO 2005/060954 | 7/2005 |
| WO | WO 2005/079797 | 9/2005 |
| WO | WO 2005/079853 | 9/2005 |
| WO | WO2005/102301 | 11/2005 |
| WO | WO 2005/123060 | 12/2005 |
| WO | WO 2005/123061 | 12/2005 |
| WO | WO 2006/017627 | 2/2006 |
| WO | WO 2006/029577 | 3/2006 |
| WO | WO 2006/062748 | 6/2006 |
| WO | WO 2006/096806 | 9/2006 |
| WO | WO 2007/011886 | 1/2007 |
| WO | WO 2007/016256 | 2/2007 |
| WO | WO 2007/017240 | 2/2007 |
| WO | WO 2007/073176 | 6/2007 |
| WO | WO 2007/075841 | 7/2007 |
| WO | WO 2007/091338 | 8/2007 |
| WO | WO 2007/128801 | 11/2007 |
| WO | WO 2007/142118 | 12/2007 |
| WO | WO 2008/004900 | 1/2008 |
| WO | WO 2008/045465 | 4/2008 |
| WO | WO 2008/088415 | 7/2008 |
| WO | WO 2008/106787 | 9/2008 |
| WO | WO 2008/115529 | 9/2008 |
| WO | WO 2008/145170 | 12/2008 |
| WO | WO 2009/004999 | 1/2009 |
| WO | WO2009/085386 | 7/2009 |
| WO | WO2009/085388 | 7/2009 |
| WO | WO 2010/028067 | 3/2010 |
| WO | WO 2010/093634 | 8/2010 |
| WO | WO 2010/127099 | 11/2010 |
| WO | WO 2010/127103 | 11/2010 |
| WO | WO 2010/147994 | 12/2010 |
| WO | WO2011/028689 | 3/2011 |
| WO | WO 2011/038122 | 3/2011 |
| WO | WO2011/085211 | 7/2011 |
| WO | WO 2011/109724 | 9/2011 |
| WO | WO 2012/074930 | 6/2012 |
| WO | WO2012/128587 | 9/2012 |
| WO | WO 2013/070735 | 5/2013 |

(56) References Cited

FOREIGN PATENT DOCUMENTS

| | | |
|---|---|---|
| WO | WO2013/103958 | 7/2013 |
| WO | WO2013/148136 | 10/2013 |
| WO | WO2014/004861 | 1/2014 |
| WO | WO2014/004993 | 1/2014 |
| WO | WO2014/005013 | 1/2014 |
| WO | WO 2014/057522 | 4/2014 |
| WO | WO2014/074552 | 5/2014 |
| WO | WO2014/130200 | 8/2014 |
| WO | WO2014/134466 | 9/2014 |
| WO | WO2014/143469 | 9/2014 |
| WO | WO2014/143523 | 9/2014 |
| WO | WO2015/021141 | 2/2015 |
| WO | WO2015/066512 | 5/2015 |
| WO | WO2015/195662 | 12/2015 |
| WO | WO2016/140949 | 9/2016 |

OTHER PUBLICATIONS

Abelo A, Andersson TB, Antonsson M, et al. "Stereoselective metabolism of omeprazole by human cytochrome P450 enzymes." Drug Metab. Dispos. Aug. 28, 2000 (8): 966-72.
Ackman et al., "The 'Basic' Fatty Acid Composition of Atlantic Fish Oils: Potential Similarties Useful for Enrichment of Polyunsaturated Fatty Acids by Urea Complexation," JAOCS, vol. 65, 1:136-138 (Jan. 1988).
Adan, Y, et al., "Effects of docosahexaenoic and eicosapentaenoic acid on lipid metabolism, eicosanoid production, platelet aggregation and atherosclerosis." Biosci. Biotechnol. Biochem. 63(1), 111-119 (Jan. 1999).
Adan, Y., et al., "Concentration of serum lipids and aortic lesion size in female and male apo E-deficient mice fed docosahexaenoic acid." Biosci. Biotechnol. Biochem. 63(2):309-313 (Feb. 1999).
Agren JJ, Vaisanen S, Hanninen O, et al. "Hemostatic factors and platelet aggregation after a fish-enriched diet or fish oil or docosahexaenoic acid supplementation." Prostaglandins Leukot Essent Fatty Acids (Oct. 1997) 57 (4-5): 419-21.
Agren, J.J., et al., "Fatty acid composition of erythrocyte, platelet, and serum lipids in strict vegans." Lipids 30:365-369 (Apr. 1995).
Agren, J.J., et al., "Fish diet, fish oil and docosahexaenoic acid rich oil lower fasting and postprandial plasma lipid levels." Eur J Clin Nutr., 50:765-771. (Nov. 1996).
Aguillar-Salinas et al., "High Prevalence of Low HDL Cholesterol Concentrations and Mixed Hyperlipidemia in a Mexican Nationwide Survey," J Lipid Res., (Aug. 2001), 42:1298-1307.
Ai M, Otokozawa S, Asztalos BF, Ito Y, Nakajima K, White CC, Cupples LA, Wilson PW, Schaefer EJ. "Small dense LDL cholesterol and coronary heart disease: results from the Framingham Offspring Study." Clin. Chem. (Jun. 2010);56(6):967-976.
Ait-Said, et al., "Inhibition by eicosapentaenoic acid of IL-1β-induced PGHS-2 expression in human microvascular endothelial cells: involvement of lipoxygenase-derived metabolites and p38 MAPK pathway." Biohimicia et Biophysica Acta, 1631:66-85 (Feb. 2003).
Alderman, J.D., et al., "Effect of a modified, well-tolerated niacin regimen on serum total cholesterol, high density lipoprotein cholesterol and the cholesterol to high density lipoprotein ratio," Am. J. Cardio, 64: 725-729.A (Oct. 1989).
Alessandri, J-M., et al., "Estradiol favors the formation of eicosapentaenoic acid (20:5n-3) and n-3 docosapentaenoic acid (22:5n-3) from alpha-linolenic acid (18:3n-3) in SH-SY5Y neuroblastoma cells." Lipids 43:19-28 (Jan. 2008).
Allard et al. "Nutritional assessment and hepatic fatty acid composition in non-alcoholic fatty liver disease (NAFLD): a cross-sectional study." J Hepatol. Feb. 2008;48(2):300-7.
Allred, C., et al., "PPARγ1 as a molecular target of eicosapentaenoic acid in human colon cancer (HT-29) cells." J. Nutr. 138:250-256 (Feb. 2008).
Almeida et al., "Effect of nebicapone on the pharmacokinetics and pharmacodynamics of warfarin in healthy subjects." Eur J Clin Pharmacol. (Oct. 2008);64(10):961-6.
Amarin Appoints Medpace as CRO for Two Phase 3 Cardiovascular Trials, published Oct. 19, 2009 (2 pages).
Amarin Corporation Announces First Patients Enrolled in Two Phase 3 Clinical Trials Assessing AMR101 for the Treatment of Cardiovascular Disease [online], Amarin Corporation, Jan. 11, 2010 [retrieved Apr. 27, 2011], Retrieved from the Internet: <http://inestor.amarincorp.com/releasedetail.cfm?ReleaseID=504380> (2 pages).
Amarin Corporation, press release (Jan. 18, 2008)(1 page).
Amarin Presentation "Next Generation Lipid Modification in Cardiovascular Disease," (Aug. 2011)(27 pages).
Amarin Presentation "Next Generation Lipid Modification in Cardiovascular Disease," (Mar. 2010)(25 pages).
Amarin Proceeding to Phase 3 with AMR101 for Hypertriglyceridemia, published Jul. 23, 2008 (1 page).
Amarin's Vascepa® Briefing Document for the Endocrinologic and Metabolic Drugs Advisory Committee Meeting dated Oct. 16, 2013, (117 pages).
Anber V, Griffin BA, McConnell M, Packard CJ, Shepherd J. Influence of plasma lipid and LDL-subfraction profile on the interaction between low density lipoprotein with human arterial wall proteoglycans. *Atherosclerosis*. Aug. 1996;124(2):261-271.
Anderson TJ, Gregoire J, Hegele RA, et al. 2012 update of the Canadian Cardiovascular Society guidelines for the diagnosis and treatment of dyslipidemia for the prevention of cardiovascular disease in the adult. Can. J. Cardiol. Feb. 2013;29:151-167.
Anderson TJ, Meredith IT, Yeung AC, Frei B, Selwyn AP, Ganz P. The effect of cholesterol-lowering and antioxidant therapy on endothelium-dependent coronary vasomotion. N. Engl. J. Med. Feb. 1995;332:488-493.
Anderson, "Lipoprotein-Associated Phospholipase A2: An Independent Predictor of Coronary Artery Disease Events in Primary and Secondary Prevention," 101 Am. J. Cardiology 23F-33F (Jun. 2008).
Ando, M., et al., "Eicosapentanoic acid reduces plasma levels of remnant lipoproteins and prevents in vivo peroxidation of LDL in dialysis patients." J. Am. Soc. Nephrol., 10:2177-2184 (Oct. 1999).
Ando, Y., et al., "Positional distribution of highly unsaturated fatty acids in triacyl-sn-glycerols of Artemia Nauplii enriched with docosahexaenoic acid ethyl ester." Lipids 36:733-740 (Jul. 2001).
Andrade, SE. et al., "Discontinuation of antihyperlipidaemic drugs_ do rates reported in clinical trials reflect rates in primary care settings?" New Eng. J. Med. 332: 1125-1131. (Apr. 1995).
Andrews HE, Bruckdorfer KR, Dunn RC, Jacobs M. Low-density lipoproteins inhibit endotheliumdependent relaxation in rabbit aorta. Nature. May 1987;327:237-239.
Angerer et al., "n-3 Polyunsaturated Fatty Acids and the Cardiovascular System", Current Opinion in Lipidology, 11(1):57-63, (Feb. 2000).
Anil, Eliz, "The Impact of EPA and DHA on Blood Lipids and Lipoprotein Metabolism: Influence of ApoE Genotype", Proceedings of the Nutrition Society, 66:60-68, (Feb. 2007).
Aoki T et al. "Experience of the use of ethyl eicosapentaenoic acid preparation (Epadel) in patients with arteriosclerosis obliterans complicated with diabetes mellitus. A study of the long-term effects on glycemic control and blood lipids," Rinsho to Kenkyu; 70:625-631. (1993) (with English translation).
Appendix A to Defendants' Invalidity Contentions, 3:14-CV-02550-MLC-DEA (D.N.J.), 478 pages. (Dec. 5, 2014).
Appleton, Katherine M., et al., "Effects of n-3 long-chain polyunsaturated fatty acids on depressed mood: systematic review of published trials", Am. J. Clin. Nutr., 84(6)1308-1316, (Dec. 2006).
Arca et al., "Treating statin-intolerant patients," Diabetes, Metabolic Syndrome and Obesity: Targets and Therapy, 4:155-156 (Apr. 28, 2011).
Arrol, S. et al., "The effects of fatty acids on apolipoprotein B secretion by human hepatoma cells (HEP G2)," Atherosclerosis 150:255-264. (Jun. 2000).
Arshad, A., et al., "Sudden cardiac death and the role of medical therapy." Progress in Cardiovascular Diseases, vol. 50, No. 6, 420-438, (May/Jun. 2008).

(56) References Cited

OTHER PUBLICATIONS

Arterburn, L., et al., "Distribution, interconversion, and dose response of n-3 fatty acids in humans." Am J Clin Nutr., 83:1467S-76S (Jun. 2006).
Asahara, EPA Products What is the Clinical Significance of Epadel? Obesity and Diabetes 10(6):903-905 (2011) (with English translation).
Asano, M., et al., "Eicosapentaenoic acid inhibits vasopressin-activated Ca2q influx and cell proliferation in rat aortic smooth muscle cell lines." European Journal of Pharmacology 379:199-209 (Aug. 1999).
Asano, M., et al., "Inhibitory effects of ω-3 polyunsaturated fatty acids on receptor-mediated non-selective cation currents in rat A7r5 vascular smooth muscle cells." British Journal of Pharmacology 120:1367-1375, (Apr. 1997).
Ascenta Health "Fish Oil as Triglycerides vs. Ethyl Esters: Why this Matters." (2015)(14 pages).
Atorvastatin Package Leaflet, Reg. No. LSR-005205/08, Sep. 30, 2016 [retrieved Sep. 30, 2016] retrieved from the internet: academ-clinic.ru/drugs/atorvastatin (6 pages).
ATP III guidelines, NIH publication No. 01-3305 (2001).(6 pages).
Attie AD, et al., "Relationship between stearoyl-CoA desaturase activity and plasma trigylcerides in human and mouse hypertriglyceridemia," J. Lipid Res. 2002;43:1899-907.
Ault, "Prescription omega-3 fatty acid formulation approved," OB.GYN.NEWS, (Jan. 15, 2005).
Avandia [package insert]. Research Triangle Park, NC: GlaxoSmithKline; 2011.(45 pages).
Avery et al., "Upper Gastrointestinal System," Integrating Therapeutic and Complementary Nutrition, Edited by Mary Marian, CRC Press (2006)(14 pages).
Aviram M, Rosenblat M, Bisgaier CL, Newton RS. Atorvastatin and gemfibrozil metabolites, but not the parent drugs, are potent antioxidants against lipoprotein oxidation. Atherosclerosis. Jun. 1998; 138(2):271-280.
Ayton, et al., "A pilot open case series of Ethyl-EPA supplementation in the treatment of anorexia nervosa," Prostaglandins, Leukotrienes and Essential Fatty Acids 71, pp. 205-209. (Oct. 2004).
Ayton, et al., "Rapid improvement of severe anorexia nervosa during treatment with ethyl-eicosapentaenoate and micronutrients," European Psychiatry 19, pp. 317-319. (Aug. 2004).
Baigent, C., et al., "Efficacy and safety of cholesterol-lowering treatment: prospective meta-analysis of data from 90,056 participants in 14 randomised trials of statins." Lancet; 366:1267-1278. (Oct. 2005).
Baldwin RM, Ohlsson S, Pedersen RS, et al. Increased omeprazole metabolism in carriers of the CYP2C19*17 allele; a pharmacokinetic study in healthy volunteers. *Br. J. Clin. Pharmacol.* May 2008 65 (5): 767-74.
Baldwin SJ, Clarke SE, Chenery RJ. Characterization of the cytochrome P450 enzymes involved in the in vitro metabolism of rosiglitazone. Br. J. Clin. Pharmacol. Sep. 1999;48:424-432.
Balk, E.M., et al., "Effects of omega-3 fatty acids on serum markers of cardiovascular disease risk: a systematic review. Atherosclerosis." 189:19-30. (Nov. 2006).
Ballantyne CM, Bays HE, Kastelein JJ, et al. Efficacy and safety of eicosapentaenoic acid ethyl ester (AMR 101) therapy in statin-treated patients with persistent high triglycerides (from the ANCHOR study). Am J Cardiol Oct. 2010 110 (7): 984-92.
Ballantyne et al., "Abstract 15071: AMR101 Lowers Triglycerides, Atherogenic Lipoprotein, Phospholipase $A_2$, and High-sensitivity C-reactive Protein Levels in Patients with High Triglycerides and on Background Statin Therapy (the ANCHOR Study)," Circulation, Lippincott Williams and Wilkins, vol. 124, No. 21, Suppl., Nov. 22, 2011.
Ballantyne et al., "Effects of icosapent ethyl on lipoprotein particle concentration and fatty acid desaturation index in statiotreated patients with persistent high triglycerides (the ANCHOR study)." Journ. Clin. Lipidology, 2013, 7(3):270-271.
Ballantyne et al., Influence of low-high density lipoprotein cholesterol and elevated triglyceride on coronary heart disease events and response to simvastatin therapy in 4S, Circulation, 104:3046-3051. (Dec. 2001).
Bang HO, Dyerberg J. "Plasma lipids and Lipoproteins in Greenlandic west coast Eskimos" Acta Med Scand, 192:85-94. (Jul./Aug. 1972).
Banga, A., et al., "Adiponectin translation is increased by the PPARγ agonists pioglitazone and ω-3 fatty acids." Am J Physiol Endocrinol Metab 296:480-489 (Mar. 2009).
Bangham et al., "Diffusion of univalent ions across the lamellae of swolloen phospholipids." J. Mol. Biol. (Aug. 1965) 13(1):238-252.
Bansal S, Buring JE, Rifai N, Mora S, Sacks FM, Ridker PM, "Fasting Compared With Nonfasting Triglycerides and Risk of Cardiovascular Events in Women," JAMA, 298:309-316 (Jul. 2007).
Barter et al., "Effectiveness of Combined Statin Plus Omega-3 Fatty Acid Therapy for Mixed Dyslipidemia." Am. J. Cardiol. 102(8):1040-1045 (Oct. 15, 2008).
Basu, A., et al., "Dietary Factors That Promote or Retard Inflammation." Arterioscler. Thromb. Vasc. Biol. 26:995-1001 (May 2006).
Baynes JW. Role of oxidative stress in development of complications in diabetes. Diabetes. Apr. 1991;40(4):405-412.
Bays HE et al. "Prescription omega 3 fatty acids and their lipid effects: physiologic mechanisms of action and clinical implications," Expert Rev Cardiovasc Ther., 6:391-409. (Mar. 2008).
Bays HE, Ballantyne CM, Braeckman RA, Stirtan WG, Soni PN. Icosapent ethyl, a pure ethyl ester of eicosapentaenoic acid: effects on circulating markers of inflammation from the MARINE and ANCHOR studies. Am. J. Cardiovasc. Drugs. Feb. 2013;13(1):37-46.
Bays HE, Braeckman RA, Ballantyne CM, et al. Icosapent ethyl, a pure EPA omega-3 fatty acid: Effects on lipoprotein particle concentration and size in patients with very high triglyceride levels (the MARINE study). J. Clin. Lipidol. Nov./Dec. 2012;6:565-572.
Bays HE, Safety considerations with omega-3 fatty acid therapy. Am. J. Cardiol. Mar. 2007 99 (6A): 35C-43C.
Bays, H., Clinical Overview of Omacor: A Concentrated Formulation of Omega-3 Polyunsaturated Fatty Acids, Am J Cardiol.; 98[suppl]:71i-76i (Aug. 2006).
Bays, H., "Rationale for Prescription Omega-3-Acid Ethyl Ester Therapy for Hypertriglyceridemia: A Primer for Clinicians," Drugs of Today, 44(3); 205-246. (Mar. 2008).
Bays, H.E., Eicosapentaenoic Acid Ethyl Ester (AMR101) Therapy in Patients With Very High Triglyceride Levels (from the Multi-center, plAcebo-controlled, Randomized, double-blINd, 12-week study with an open-label Extension [MARINE] Trial) Am J Cardiol;108:682-690. (Sep. 2011).
Bays, H.E., et al., "Long-term up to 24-month efficacy and safety of concomitant prescription omega-3-acid ethyl esters and simvastatin in hypertriglyceridemic patients." Curr Med Res Opin.; 26:907-915. (Apr. 2010).
Beal, M.F., Annals of Neurology, vol. 38, No. 3, "Aging, Energy, and Oxidative Stress in Neurodegenerative Diseases", pp. 357-366, (Sep. 1995).
Beaumont et al., Design of Ester Prodrugs to Enhance Oral Absorption of Poorly Permeable Compounds: Challenges to the Discovery Scientist, Current Drug and Metabolism. (Dec. 2003) 4:461-485.
Belarbi et al., "A process for high yield and scaleable recovery of high purity eicosapentaenoic acid esters from microalgae and fish oil," Enzyme and Microbail Technology 26:516-529 (Apr. 2000).
Belger et al., "Assessment of prefrontal activation by infrequent visual targets and non-target noval stimuli in schisophrenia: a function MRI study, " Presented at the 9th Biennial winter workshop on schizophrenia, Davos, Switzerland, Feb. 7-13, 1998, Abstract in Schizophrenia Research. vol. 29. No. 1/02, Jan. 1998.
Belikov, Pharmaceutical Chemistry in Two Parts, 1/General Pharmaceutical Chemistry 43-47 (1993) (with English translation)(9 pages).
Belmaker et al., "Addition of Omega-3 Fatty Acid to Maintenance Medication Treatment for Recurrent Unipolar Depressive Disorder," Am. J. Psychiatry, 159:477-479 (Mar. 2002).
Belmaker, et al., "Omega-3 Eicosapentaenoic Acid in Bipolar Depression: Report of a Small Open-Label Study," J Clin Psychiatry; 66:726-729. (Jun. 2005).

(56) References Cited

OTHER PUBLICATIONS

Bender NK, Kraynak MA, Chiquette E, et al. Effects of marine fish oils on the anticoagulation status of patients receiving chronic warfarin therapy. J. Thromb. Thrombolysis Jul. 5, 1998 (3): 257-61.
Bénistant, C., et al., "Docosapentaenoic acid (22:5, n-3): metabolism and effect on prostacyclin production in endothelial cells." Prostaglandins, Leukotrienes and Essential Fatty Acids, 55(4):287-292, (Oct. 1996).
Benn et al., Improving Prediction of Ischemic Cardiovascular Disease in the General Population Using Apolipoprotein B: The Copenhagen City Heart Study, 27 Arteriosclerosis, Thrombosis, & Ascular Biology 661 (Mar. 2007).
Bennett et al., "Treatment of IgA nephropathy with eicosapentanoic acid (EPA): a two-year prospective trial [Abstract Only]." Clin. Nephrol. 31(3):128-131 (Mar. 1989).
Berge, R.K., et al., "In contrast with docosahexaenoic acid, eicosapentaenoic acid and hypolipidaemic derivatives decrease hepatic synthesis and secretion of triacylglycerol by decreased diacylglycerol acyltransferase activity and stimulation of fatty acid oxidation." Biochem J.; 343(Pt 1):191-197. (Oct. 1999).
Berglund L, Brunzell JD, Goldberg AC, et al. Evaluation and treatment of hypertriglyceridemia: an endocrine society clinical practice guideline. J. Clin. Endocrinol. Metab. Sep. 2012 97 (9): 2969-89.
Berliner JA, Watson AD. A role for oxidized phospholipids in atherosclerosis. N. Engl. J. Med. Jul. 2005;353(1):9-11.
Bertelsen M, Anggard EE, Carrier MJ. Oxidative stress impairs insulin internalization in endothelial cells in vitro. Diabetologia. May 2001;44(5):605-613.
Betteridge, D.J., "Diabetic dyslipidaemia: past, present and future." Practical Diabetes Int, 21(2): 78-85. (Mar. 2004).
Bild et at., "Multi-Ethnic Study of Atherosclerosis: objectives and design," Am J Epidemiol 156(9):871-81 (Nov. 1, 2002).
Black et al., "Effect of intravenous eicosapentaenoic acid on cerebral blood flow, edema, and brain prostaglandins in ischemic gerbils", Prostaglandins, 28(4), pp. 545-546. (Oct. 1984).
Blankenhorn D.H. et al., "Beneficial effects of combined colestipol-niacin therapy on coronary atherosclerosis and coronary venous bypass grafts." JAMA 257: 3233-3240. (Jun. 1987).
Block, R. C., et al., "EPA and DHA in blood cell membranes from acute coronary syndrome patients and controls." Atherosclerosis, 197(2):821-828 (Apr. 2008).
Blumenthal, Advanced Studies in Medicine, 2:148-157 (2002).
Boden WE, Probstfield JL, Anderson T, Chaitman BR, Desvignes-Nickens P, Koprowicz K, IJ McBride R, Teo K, Weintraub W. and the Aim-High Investigators "Niacin in patients with low hdl cholesterol levels receiving intensive statin therapy," N. Engl. J. Med. Dec. 2011;365:2255-2267.
Bonaa, KH et al., Docosahexaenoic and Eicosapentaenoic acids in plasma phospholipids are divergently associated with high density lipoprotein in humans, Arterioscler. Thromb. Vasc. Biol.;12;675-681 (Jun. 1992).
Bonnet et al., "Comparative Effects of 10-mg Versus 80-mg Atorvastatin on High-Sensitivity C-Reactive Protein in Patients with Stable Coronary Artery Disease: Results of the CAP (Comparative Atorvastatin Pleiotropic Effects) Study," Clinical Therapeutics. 30(12):2298-2313 (Dec. 2008).
Borchman D, Lamba OP, Salmassi S, Lou M, Yapped MC. The dual effect of oxidation on lipid bilayer structure. Lipids. Apr. 1992;27(4):261-265.
Bordin et al., "Effects of fish oil supplementation on apolipoprotein B100 production and lipoprotein metabolism in normolipidaemic males," Eur. J. Clin. Nutr. 52: 104-9 (Feb. 1998).
Borow et al., "Biologic plausibility, cellular effects, and molecular mechanisms of eicosapentaenoic acid (EPA) in atherosclerosis," Atherosclerosis, 242(1):357-66 (Sep. 2015).
Borthwick et al., "The effects of an omega-3 ethyl ester concentrate on blood lipid concentrations in pateitns with hyperlipidemia," Clin. Drug Investig. (1998) 15(5): 397-404.

Bossaller C, Habib GB, Yamamoto H, Williams C, Wells S, Henry PD. Impaired muscarinic endothelium-dependent relaxation and cyclic guanosine 5'-monophosphate formation in atherosclerotic human coronary artery and rabbit aorta. J. Clin. Invest. Jan. 1987;79:170-174.
Bousserouel, S., et al., "Different effects of n-6 and n-3 polyunsaturated fatty acids on the activation of rat smooth muscle cells by interleukin-1 beta." J. Lipid Res. 44:601-611 (Mar. 2003).
Bousserouel, S., et al., "Modulation of cyclin D1 and early growth response factor-1 gene expression in interleukin-1beta-treated rat smooth muscle cells by n-6 and n-3 polyunsaturated fatty acids." Eur. J. Biochem. 271:4462-4473 (Nov. 2004).
Brady, L., et al., Increased n-6 polyunsaturated fatty acids do not attenuate the effects of long-chain n-3 polyunsaturated fatty acids on insulin sensitivity or triacylglycerol reduction in Indian Asians. Am J Clin Nutr 79:983-91(Jun. 2004).
Braeckman et al., "Abstract 18549: Effects of AMR101, a Pure Eicosapentaenoic Omega-3 Fatty Acid, on the Fatty Acid Profile in Plasma and Red Blood Cells in Statin-Treated Patients with Persistent High Triglycerides—Results from the ANCHOR study," Circulation 126(21S):A15071 (Nov. 20, 2012)(2 pages).
Braeckman et al., "Effect of Concomitant Icosapent Ethyl (Eicosapentaenoic Acid Ethyl Ester) on Pharmacokinetics of Atorvastatin," Clinical Drug Investigation. (Jan. 2015) (3)45-51.
Braeckman RA, Manku MS, Bays HE, Stirtan WG, Soni PN. Icosapent ethyl, a pure EPA omega-3 fatty acid: effects on plasma and red blood cell fatty acids in patients with very high triglyceride levels (results from the MARINE study). Prostaglandins Leukot Essent Fatty Acids. Sep. 2013;89(4):195-201.
Braeckman RA, Stirtan WG, Soni PN. Pharmacokinetics of eicosapentaenoic acid in plasma and red blood cells after multiple oral dosing with AMR101 (ethyleicosapentaenoic acid) in healthy subjects [abstract]. Presented at: Congress of the International Society for the Study of Fatty Acids and Lipids, Vancouver, Canada, May 26-30, 2012.
Braeckman RA, Stirtan WG, Soni PN. Pharmacokinetics of eicosapentaenoic acid in plasma and red blood cells after multiple oral dosing with icosapent ethyl in healthy subjects. Clin. Pharmacol. Drug Dev. 2013;3:101-108.
Braunersreuther V, Steffens S, Arnaud C, Pelli G, Burger F, Proudfoot A, Mach F. A novel rantes antagonist prevents progression of established atherosclerotic lesions in mice. Arterioscler. Thromb. Vasc. Biol. Jun. 2008;28:1090-1096.
Breslow, J., "n-3 Fatty acids and cardiovascular disease." Am J Clin Nutr., 83:1477S-82S (Jun. 2006).
Brinton EA, Ballantyne CM, Bays HE, Kastelein JJ, Braeckman RA, Soni PN. Effects of AMR101 on lipid and inflammatory parameters in patients with diabetes mellitus-2 and residual elevated triglycerides (200-500 mg/dl) on statin therapy at LDL-C goal: the ANCHOR study.[abstract 629-P] Diabetes. 2012;61(suppl 1):A159-A160.
Brossard, N., et al., "Retroconversion and metabolism of [13C]22:6n-3 in humans and rats after intake of a single dose of [13C]22:6n-3-3-triacyylglycerols." Am. J. Clin. Nutr. 64:577-86 (Oct. 1996).
Brouwer, I.A., et al., "Effect of fish oil on ventricular tachyarrhythmia and death in patients with implantable cardioverter defibrillators." JAMA. 295(22):2613-2619 (Jun. 2006).
Brovkovych V, Dobrucki LW, Brovkovych S, Dobrucki I, Do Nascimento CA, Burewicz A, Malinski T. Nitric oxide release from normal and dysfunctional endothelium. J. Physiol. Pharmacol. Dec. 1999;50:575-586.
Brown et al., Simvastatin and Niacin, Antioxidant Vitamins, or the Combination for the Prevention of Coronary Disease, N Engl J Med, vol. 345, No. 22, 1583-1592 (Nov. 29, 2001).
Brown, A. J., et al., "Administration of n-3 Fatty Acids in the Diets of Rats or Directly to Hepatocyte Cultures Results in Different Effects on Hepatocellular ApoB Metabolism and Secretion." Arterioscler. Thromb. Vasc. Biol. 19:106-114 (Jan. 1999).
Brown, A. J., et al., "Persistent changes in the fatty acid composition of erythrocyte membranes after moderate intake of n-3 polyunsaturated fatty acids: study design and implications." Am.J. Clin. Nutri. 54;668-73(Oct. 1991).

(56) References Cited

OTHER PUBLICATIONS

Brown, G., et al., "Regression of coronary artery-disease as a result of intensive lipid-lowering therapy in men with high levels of apolipoprotein," B., N. Engl. J. Med. 323: 1289-1298. (Nov. 1990).
Brownlee M. Biochemistry and molecular cell biology of diabetic complications. Nature. Dec. 2001; 414(6865):813-820.
Bryhn, M., et al., "The bioavailability and pharmacodynamics of different concentrations of omega-3 acid ethyl esters." Prostaglandins, Leukotrienes and Essential Fatty Acids 75:19-24 (Jul. 2006).
Budavari, S., Editor, "The Merck Index", Merck & Co., Inc., p. 725 item 4511 and p. 279 and item 2417 (1989).
Budoff, "Triglycerides and Triglyceride-Rich Lipoproteins in the Causal Pathway of Cardiovascular Disease," Am. J. Cardiol., 118(1):138-45 (Jul. 1, 2016).
Bunting et al. "Depression in Parkinson's Disease". J Neurosci Nurs.; 23(3):158-164. (Abstract Only) (Jun. 1991).
Burdge, G.C., et al., "Eicosapentaenoic and docosapentaenoic acids are the principal products of a-linolenic acid metabolism in young men." British Journal of Nutrition 88:355-363 (Oct. 2002).
Burdge, G.C., et al., "Lack of effect of meal fatty acid composition on postprandial lipid, glucose and insulin responses in men and women aged 50-65 years consuming their habitual diets." British Journal of Nutrition, 96:489-500 (Sep. 2006).
Burdge, G.C., et al., "The effect of altering the 20:5n-3 and 22:6n-3 content of a meal on the postprandial incorporation of n-3 polyunsaturated fatty acids into plasma triacylglycerol and non-esterified fatty acids in humans." Prostaglandins, Leukotrienes and Essential Fatty Acids 77:59-65 (Jul. 2007).
Burr, M. L., et al., "Effects of changes in fat, fish and fibre intakes on death and myocardial reinfarction: Diet and reinfarction trial." The Lancet, 2(8666):757-61 (Sep. 1989).
Buse JB, Ginsberg HN, Bakris GL, et al. Primary prevention of cardiovascular diseases in people with diabetes mellitus: a scientific statement from the American Heart Association and the American Diabetes Association. Diabetes Care. 2007;30: 162-172.
Calabresi, L., et al., "Omacor in familial combined hyperlipidemia: effects on lipids and low density lipoprotein subclasses." Atherosclerosis 148:387-396 (Feb. 2000).
Calder PC. The role of marine omega-3 (n-3) fatty acids in inflammatory processes, atherosclerosis and plaque stability. Mol. Nutr. Food Res. Jul. 2012;56(7):1073-1080.
Campos, H., et al., "Lowdensity lipoprotein size, pravastatin treatment, and coronary events." JAMA, 286:1468-1474 (Sep. 2001).
Canner P.L. et al., "Fifteen year mortality in Coronary Drug Project patients: long-term benefit with niacin," J. Am. Coll. Cardiol. 8. 1245-1255. (Dec. 1986).
Cao, et al., "Cloning, Expression, and Chromosomal Locatlization . . . ", Genomics, 49:327-331, (Apr. 15, 1998).
Cao, J., et al., "Incorporation and Clearance of Omega-3 Fatty Acids in Erythrocyte Membranes and Plasma Phospholipids." Clinical Chemistry 52(12):2265-2272 (Dec. 2006).
Capuzzi, DM et al., "Efficacy and safety of an extended-release niacin (Niaspan): a long-term study." Am. J. Cardiol. 82: 74U-81U. (Dec. 17, 1998).
Carlson, L.A. & Rosenhamer G., "Reduction of mortaility in the Stockholm Ischaemic Heart Disease Secondary Prevention Study by combined treatment with clofibrate and nicotinic acid." Acta Med. Scand. 223, 405-418 (1988).
Carlson, L.A., "Nicotinic acid: the broad spectrum lipid drug. A 50th Anniversary review", J. Int. Med., 258:94-114, (Aug. 2005).
Carrero et al., "Intake of Fish Oil, Oleic Acid, Folic Acid, and Vitamins B-6 and E for 1 Year Decreases Plasma C-Reactive Protein and Reduces Coronary Heart Disease Risk Factors in Male Patients in a Cardiac Rehabilitation Program", pp. 384-390 (Feb. 2007).
Carrero, J.J. et al. "Efectos cardiovasculares de los acidos grasos omega-3 y alternatives para incrementar su ingesta," Nutricion Hospitalaria. (2005) (1) 63-69 [with English abstract].
Carroll, D. N., et al., "Evidence for the Cardioprotective Effects of Omega-3 Fatty Acids." Ann Pharmacother., 36:1950-6 (Dec. 2002).

Cazzola, R., et al., "Age- and dose-dependent effects of an eicosapentaenoic acid-rich oil on cardiovascular risk factors in healthy male subjects." Atherosclerosis 193:159-167 (Jul. 2007).
Ceci et al., "The effects of oral 5-hydroxytryptophan administration on feeding behavior in obese adult female subjects," J Neural. Transm (1989) 76(2):109-117.
Cefali, E.A., et al., "Aspirin reduces cutaneous flushing after administration of an optimised extended-release niacin formulation", Int. J. Clin. Pharmacol. & Ther., 45(2):78-88, (Feb. 2007).
Center for Drug Evaluation and Research. Application No. 21-853, 21654s016, (Omacor). Statistical Review and Evaluation: Clinical Studies, Omacor (omega-3 acid ethyl ester) Capsules, 4 grams/day; 2007. Available at: http://www.accessdata.fda.gov/drugsatfda_docs/nda/2007/021853s000;%20021654s016_StaR.pdf. (Accessed Jan. 26, 2012) (156 pages).
Center for Drug Evaluation and Research. Approval Package for Application No. 202057Orig1s000. Review—Vascepa (formerly AMR101), 373 pages (Jul. 26, 2012)(in two parts).
Center for Drug Evaluation and Research. Approval Package for: 21-654 (Omacor/Lovaza). Statistical Review; 2004. Available at: http://www.accessdata.fda.gov/drugsatfda_docs/nda/2004/21-654_Omacor_AdminCorres_P1.pdf. Accessed Jan. 26, 2012. (54 pages).
Ceriello A, Motz E. Is oxidative stress the pathogenic mechanism underlying insulin resistance, diabetes, and cardiovascular disease? The common soil hypothesis revisited. Arterioscler. Thromb. Vasc. Biol. (May 2004);24(5):816-823.
Chait A, Brazg RL, Tribble DL, Krauss RM. Susceptibility of small, dense, low-density lipoproteins to oxidative modification in subjects with the atherogenic lipoprotein phenotype, pattern B. Am. J. Med. (Apr. 1993);94(4):350-356.
Chan et al., "Effect of Atorvastatin and Fish Oil on Plasma High-Sensitivity C-Reactive Protein Concentrations in Individuals with Visceral Obesity", Clin. Chem., vol. 48, pp. 877-883 (2002).
Chan et al., Factorial Study of the Effects of Atorvastatin and Fish Oil on Dyslipidaemia in Visceral Obesity, 32 Euro. J. Clinical Investigation. 32(6):429-36 (Jun. 2002).
Chan, D.C., et al., "Randomized controlled trial of the effect of n-3 fatty acid supplementation on the metabolism of apolipoprotein B-100 and chylomicron remnants in men with visceral obesity." Am J Clin Nutr 77:300-7 (2003).
Chapman, M.J., et al., "Cholesteryl ester transfer protein: at the heart of the action of lipid-modulating therapy with statins, fibrates, niacin, and cholesteryl ester transfer protein inhibitors." Eur Heart J., 31(2):149-164 (Jan. 2010).
Chatterjee SN, Agarwal S. Liposomes as membrane model for study of lipid peroxidation. Free Radic. Biol. Med. 1988;4(1):51-72.
Chemical Book, Eicosapentaenoic acid ethyl ester, copyright 2010, printed Jun. 16, 2011 from www.chemicalbook.com. (2010).
Chen, H., et al., "Eicosapentanoic acid inhibits hypoxia-reoxygenation-induced injury by attenuating upregulation of MMP-1 in adult rat myocytes." Cardiovascular Research 59:7-13 (Jul. 2003).
Chen, H., et al., "EPA and DHA attenuate ox-LDL-induced expression of adhesion molecules in human coronary artery endothelial cells via protein kinase B pathway." Journal of Molecular and Cellular Cardiology 35:769-775 (Jul. 2003).
Chen, I.S., et al., "In vitro clearance of chylomicron triglycerides containing (ω-3) eicosapentaenoate." Atherosclerosis, 65:193-198 (1987).
Cheng et al., "Antagonism of the prostaglandin D2 receptor 1 suppresses nicotinic acid-induces vasodilation in mice and humans," PNAS 103(17):6682-7 (Apr. 25, 2006).
Childs, M.T., et al., "Divergent lipoprotein Responses to Fish Oils With Various Ratios of Eicosapentaenoic Acid and Docasahexaenoic Acid", American Society for Clinical Nutrition, 52:632-9, (Oct. 1990).
Christensen, J. H., et al., "Effect of fish oil on heart rate variability in survivors of myocardial infarction: a double blind randomised controlled trial." BMJ, 312:677-678 (Mar. 16, 1996).
Christensen, M.S., et al., "Intestinal absorption and lymphatic transport of eicosapentaenoic (EPA), docosahexaenoic (DHA), and decanoic acids: dependence on intramolecular triacyiglycerol structure." Am J Clin Nutr 61:56-61 (Jan. 1995).

(56) References Cited

OTHER PUBLICATIONS

Classification of Hyperlipidaemias and Hyperlipoproteinaemias, Bulletin of the World Health Organization, 43(6): 891-915 (1970).
Cleland, L.G., et al., "A Biomarker of n-3 compliance in patients taking fish oil for rheumatoid arthritis." Lipids 38:419-424 (Apr. 2003).
Clinical Trial NCT01047501, Effect of AMR101 (Ethyl Icosapentate) on Triglyceride (Tg) Levels in Patients on Statins With High Tg Levels (>200 and <500 mg/dL) (ANCHOR), ClinicalTrials.gov [database online], U.S. National Institute of Health, Jan. 2010 [retrieved Apr. 27, 2011], Retrieved from the Internet: <http://clinicaltrials.gov/ct2/show/NCT01047501> (3 pages).
Cohen AW, Combs TP, Scherer PE, Lisanti MP. Role of caveolin and caveolae in insulin signaling and diabetes. American journal of physiology. Endocrinology and metabolism. (Dec. 2003);285(6):E1151-1160.
Cohen, J.D., et al., "30-year trends in serum lipids among United States adults: results from the National Health and Nutrition Examination Surveys II, III, and 1999-2006." Am J Cardiol., 106:969-975. (Dec. 15, 2010).
Cole et al., "Challenges and opportunities in the encapsulation of liquid and semi-solid formulations into capsules for oral administration," Advanced Drug Delivery Reviews, vol. 60, No. 6, pp. 747-756. (Mar. 17, 2007).
Colhoun, H. M., et al., "Primary prevention of cardiovascular disease with atorvastatin in type 2 diabetes in the Collaborative Atorvastatin Diabetes Study (CARDS): multicentre randomised placebo-controlled trial." Lancet 364: 685-9 (Aug. 21-24, 2004).
Collins, N., et al., "Differences between Dietary Supplement and Prescription Drug Omega-3 Fatty Acid Formulations: A Legislative and Regulatory Perspective." Journal of the American College of Nutrition, 27 (6):659-666 (Dec. 2008).
Committee Roster for the Oct. 16, 2013 Meeting of the Endocrinologic and Metabolic Drugs Advisory Committee, 2 pages. (2013).
Conklin, S. M., et al., "Serum ω-3 fatty acids are associated with variation in mood, personality and behavior in hypercholesterolemic community volunteers." Psychiatry Research 152: 1-10 (Jul. 30, 2007).
Connor et al., "Seminars in thrombosis and hemostasis," 14:271-284. (1988).
Connor, W.E., "Importance of n-3 Fatty Acids in Health and Disease", Am. J. Clin. Nutr., 71(1(S)):171S-175S, (Jan. 2000).
Conquer, J.A., et al., "Effect of supplementation with different doses of DHA on the levels of circulating DHA as non-esterified fatty acid in subjects of Asian Indian background. J Lipid Res." 39:286-292. (Feb. 1998).
Conquer, J.A., et al., "Supplementation with an algae source of docosahexaenoic acid increases (n-3) fatty acid status and alters selected risk factors for heart disease in vegetarian subjects." J Nutr., 126: 3032-3039. (Dec. 1996).
Contacos et al. Effect of pravastatin and omega-3 fatty acids on plasma lipids and lipoproteins in patients with combined hyperlipidemia, pp. 1755-1762 (Dec. 1993).
Coronary Artery Bypass Grafting, NIH, published online Feb. 23, 2012 (12 pages).
Coumadin [package insert], Princeton, NJ: Bristol-Myers Squibb; 2011. (10 pages).
Cox PJ, Ryan DA, Hollis FJ, et al. Absorption, disposition, and metabolism of rosiglitazone, a potent thiazolidinedione insulin sensitizer, in humans. Drug Metab. Dispos. Jul. 2000;28:772-780.
Creager MA, Gallagher SJ, Girerd XJ, Coleman SM, Dzau VJ, Cooke JP. L-arginine improves endothelium-dependent vasodilation in hypercholesterolemic humans. J. Clin. Invest. Oct. 1992;90:1248-1253.
Crevel et al., "Allergenicity of Refined Vegetable Oils," Food and Chemical Toxicology, 38, pp. 385-393 (Apr. 2000).
Criqui, M., "Triglycerides and Coronary Heart Disease Revisited (Again)," vol. 147 No. 6, pp. 425-427 (Sep. 18, 2007).
Cromwell et al., "LDL particle number and risk of future cardiovascular disease in the Framingham Offspring Study—Implications for LDL Management," Journal of Lipidololgy. (Dec. 2007) 1, 583-592.
Crowe, F. L., et al., "Serum phospholipid n-3 long-chain polyunsaturated fatty acids and physical and mental health in a population-based survey of New Zealand adolescents and adults." Am J Clin Nutr 86:1278-85 (Nov. 2007).
Cruz et al., "The metabolic syndrome in children and adolescents," Curr. Diab. Rep., vol. 4(1):53-62 (Feb. 2004).
Culhane et al., "Rosuvastatin for the treatment of hypercholesterolemia," Pharmacotherapy, 25(7):990-1000 (Jul. 2005).
Daggy, B., et al., Dietary fish oil decreases VLDL production rates. Biochimica et Biophysics Acta 920: 293-300 (Aug. 15, 1987).
Dall et al., "Clinical utility of low-density lipoprotein particle measurement in management of cardiovascular disease: a case report," Research Reports in Clin. Cardiol., vol. 2, pp. 57-62 (2011).
Das, U.N., Essential fatty acids as possible mediators of the actions of statins. Prostaglandins, Leukotrienes and Essential FattyAcids 65(1):37-40, (Jul. 2001).
Davidson MH, Ballantyne CM, Jacobson TA, et al. Clinical utility of inflammatory markers and advanced lipoprotein testing: advice from an expert panel of lipid specialists. J. Clin. Lipidol. Sep./Oct. 2011;5:338-367.
Davidson MH, et al., Effects of prescription omega-3-acid ethyl esters on lipo protein particle concentrations, apolipoproteins AI and CIII, and lipoprotein-associated phospholipase $A_2$ mass in statin-treated subjects with hypertrigylceridemia, J.Clin. Lipid., vol. 3(5), pp. 332-340 (Oct. 2009).
Davidson MH, Rosenson RS, Maki KC, Nicholls SJ, Ballantyne CM, Mazzone T, Carlson DM, Williams LA, Kelly MT, Camp HS, Lele A, Stolzenbach JC. Effects of fenofibric acid on carotid intima-media thickness in patients with mixed dyslipidemia on atorvastatin therapy: Randomized, placebo-controlled study (first). Arterioscler. Thromb. Vasc. Biol. Jun. 2014;34:1298-1306.
Davidson MH, Stein EA, Bays HE et al. "Efficacy and tolerability of adding prescription omega-3 fatty acids 4 g/d to simvastatin 40 mg/d in hypertriglyceridemic patients: an 8-week, randomized, double-blind, placebo-controlled study," Clin Ther., 29:1354-1367. (2007).
Davidson MH., "Mechanisms for the hypotriglyceridemic effect of marine omega 3 fatty acids." Am J Cardiol 98(4A):27i-33i. (2006).
Davidson, M.H., et al., "Effects of docosahexaenoic acid on serum lipoproteins in patients with combined hyperlipidemia: a randomized, doubleblind, placebo-controlled trial." J Am Coll Nutr., 16:236-243. (1997).
Davies-Tuck et al., "Total cholesterol and triglycerides are associated with development of new bone marrow lesions in asymptomatic middle-aged women—a prospective cohort study," Arthritis Research & Therapy. (2009) pp. 1-7.
De Caterina, R, et al., "Control of Endothelial Leukocyte Adhesion Molecules by Fatty Acids." Lipids, vol. 31:S57-S63 (1996).
De Caterina, R., et al., "The Omega-3 fatty acid docosahexaenoate reduces cytokine-induced expression of proatherogenic and proinflammatory proteins in human endothelial cells." Arterioscler. Thromb. Vasc. Biol. 14:1829-1836 (1994).
De Graaf J, Hak-Lemmers HL, Hectors MP, Demacker PN, Hendriks JC, Stalenhoef AF. Enhanced V susceptibility to in vitro oxidation of the dense low density lipoprotein subfraction in healthy subjects. Arterioscler. Thromb. 1991;11(2):298-306.
Deckelbaum,, R. J., et al., "Conclusions and recommendations from the symposium, Beyond Cholesterol: Prevention and Treatment of Coronary Heart Disease with n-3 Fatty Acids." Am J Clin Nutr 87:2010S-12S (2008).
Defendants' Invalidity Contentions, 3:14-CV-02550-MLC-DEA (D.N.J.), 520 pages (Dec. 5, 2014).
Defendants' Joint Invalidity Contentions, 3:14-CV-02550-MLC-TJB (D.N.J.), 901 pages (Dec. 5, 2014).
Dewailly, E., et al., "n-3 Fatty acids and cardiovascular disease risk factors among the Inuit of Nunavik." Am J Clin Nutr 74:464-73 (2001).
Di Spirito, M., Morelli, G., Doyle, R.T., Johnson, J. & McKenney, J. Effect of omega-3-acid ethyl esters on steady-state plasma

(56) References Cited

OTHER PUBLICATIONS pharmacokinetics of atorvastatin in healthy adults. Expert Opin. Pharmacother. 9, 2939-2945 (2008).
Diagnostic and Statistical Manual of Mental Disorders, 4.Ed. Text revision, published by the American Psychiatric Assoc., pp. 154-163 and 369-381 (2000).
Diagnostic and Statistical Manual of Mental Disorders, 4.sup.th Ed., published by the American Psychiatric Assoc., pp. 285-286, (1994).
Dijan, P., et al., Proc. Natl. Acad. Sci., vol. 93, "Codon repeats in genes associated with human diseases: Fewer repeats in the genes of nonhuman primates and nucleotide substitutions concentrated at the sites of reiteration," pp. 417-421, (1996).
Dijk, J. M., et al., "Carotid intima-media thickness and the risk of new vascular events in patients with manifest atherosclerotic disease: the SMART study." European Heart Journal 27:1971-1978 (2006).
Din et al., "Omega 3 fatty acids and cardiovascular disease—fishing for a natural treatment," BMJ, vol. 327, No. 7430, pp. 30-35 (2004).
Dodin, S., et al., "Flaxseed on cardiovascular disease markers in healthy menopausal women: a randomized, double-blind, placebo-controlled trial." Nutrition 24:23-30 (2008).
Dolecek, "Epidemiological Evidence of Relationships Between Dietary Polyunsaturated Farry Acids and Morality in the Multiple Risk Factor Intervention Trial", Society of Experimental Biology and Medicine, 200(2):177-182, (1991).
Draft Agenda for the Oct. 16, 2013 Meeting of the Endocrinologic and Metabolic Drugs Advisory Committee, 2 pages.
Draft Meeting Roster for the Oct. 16, 2013 Meeting of the Endocrinologic and Metabolic Drugs Advisory Committee, 2 pages.
Draft Questions for the Oct. 16, 2013 Meeting of the Endocrinologic and Metabolic Drugs Advisory Committee, 1 page.
Drexler H, Zeiher AM, Meinzer K, Just H. Correction of endothelial dysfunction in coronary microcirculation of hypercholesterolaemic patients by !-arginine. Lancet. 1991;338:1546-1550.
Dullenmeijer, C., et al., "n-3 Fatty acid proportions in plasma and cognitive performance in older adults." Am J Clin Nutr 86:1479-85 (2007).
Duncan, R. E., et al., "Regulation of HMG-CoA reductase in MCF-7 cells by genistein, EPA, and DHA, alone and in combination with mevastatin." Cancer Letters 224:221-228 (2005).
Durrington PN et al. "An omega 3 poly unsaturated fatty acid concentrate administered for one year decreased triglycerides in simvastatin treated patients with coronary heart disease and persistent Hypertriglyceridemia," Heart, 85:544-48 (2001).
Dwyer, J. H., et al., "Arachidonate 5-Lipoxygenase Promoter Genotype, Dietary Arachidonic Acid, and Atherosclerosis." N. Engl. J. Med., 350:1 (2004).
Dyerberg, J., et al., "Marine Oils and Thrombogenesis." Prog. Lipid Res. 21:255-269 (1982).
Egert, S., et al., "Dietary alpha-linolenic acid, EPA and DHA have differential effects on LDL fatty acids composition but similar effects on serum lipid profiles in normolipidemic humans." J Nutr., 139:861-868 (2009).
Ehara S, Ueda M, Naruko T, Haze K, Itoh A, Otsuka M, Komatsu R, Matsuo T, Itabe H, Takano T, Tsukamoto Y, Yoshiyama M, Takeuchi K, Yoshikawa J, Becker AE. Elevated levels of oxidized low density lipoprotein show a positive relationship with the severity of acute coronary syndromes. Circulation. 2001;103(15):1955-1960.
Eilat-Adar et al. "Association of Intentional Changes in Body Weight with Coronary Heart Disease Event Rates in Overweight Subjects who have an Additional Coronary Risk Factor," Amer. Journ. Epidemiol.161(4)pp. 352-358 (Sep. 9, 2004).
Eisenberg S, Bilheimer DW, Levy RI, Lindgren FT. "On the metabolic conversion of human plasma very low density lipoprotein to low density lipoprotein," Biochim Biophys Acta, 326:361-77 (1973).
Eisenberg S, Rachmilewitz D. "Metabolism of rat plasma very low density lipoprotein. I. Fate in circulation of the whole lipoprotein," Biochim Biophys Acta, 326:378-90 (1973).

El-Serag HB, Graham DY, Satia JA, et al. Obesity is an independent risk factor for GERD symptoms and erosive esophagitis. Am. J. Gastroenterol. Jun. 2005 100 (6): 1243-50.
Elam, M.B., et al., "Effect of niacin on lipid and lipoprotein levels and glycemic control in patients with diabetes and peripheral arterial disease study: a randomized trial", The ADMIT [Arterial Disease Multiple Intervention Trial] JAMA, 284:1263-1270, (2000).
El-Saadani M, Esterbauer H, El-Sayed M, Gober M, Nassar AY, Jurgens G. A spectrophotometric assay for lipid peroxides in serum lipoproteins using commercially available reagent. J. Lipid Res. 1989;30:627-630.
El-Sohemy, A., et. al., "Regulation of Mevalonate Synthesis in Low Density Lipoprotein Receptor Knockout Mice Fed n-3 or n-6 Polyunsaturated Fatty Acids." Lipids, 34 (10): 1037-43 (1999).
Emsley et al., "Randomized, Placebo-Controlled Study of Ethyl-Eicosapentaenoic Acid as Supplemental Treatment in Schizophrenia," Am. J. Psychiatry, 159:1596-1598 (2002).
Endo et al., "The Effects of Dietary Fatty Acids on Serum Lipids and Plasma Prostaglandin Levels in the Treatment of Obesity," Japanese Journal of Pediatric Gastroenterology and Nutrition 7(1):67-72 (Apr. 15, 1993) (with English translation)(22 pages).
ENews, "Cholesterol Crystals Induce Atherosclerosis-Associated Inflammation in Mice," 1-4 (Jun. 14, 2010)(4 pages).
Engler, et al., "Docosahexaenoic acid restores endothelial function in children with hyperlipidemia: results from the EARLY Study." International Journal of Clinical Pharmacology and Therapeutics, vol. 42—No. 12-2004 (672-679). (2004).
Engler, M.B., et al., "Mechanisms of vasorelaxation induced by eicosapentaenoic acid (20:5n-3) in WKY rat aorta." British Journal of Pharmacology 131:1793-1799 (2000).
Engler, M.M., et al., "The effects of a diet rich in docosahexaenoic acid on organ and vascular fatty acid composition in spontaneously hypertensive rats." Prostaglandins, Leukotrienes and Essential Fatty Acids 61(5):289-295 (1999).
Ennis JL, Cromwell WC. Clinical utility of low-density lipoprotein particles and apolipoprotein B in patients with cardiovascular risk. J. Fam. Pract. 2013;62:1-8.
Epadel—PubChem CID 9831415, Retrieved on Apr. 9, 2014 [Retrieved from the internet] <URL:http://pubchem.ncbi.nlm.nih.gov/compound/9831415> (19 pages).
Epadel 1990 and JELIS Study (4 pages).
Epadel Capsules 300, Japan Pharmaceutical Reference 369-371 (2nd ed.) (1991). (5 pages).
Epadel drug information brochure (2000), certified English translation(36 pages).
Epadel Package Insert 2007 (with Translation)(6 pages).
Epadel® [Complete prescribing information]. Update (Version 5). Tokyo, Japan: Mochida Pharmaceutical; Jan. 2007 (9 pages).
EPANOVA® (omega-3-carboxylic acids) capsules, for oral use, Prescribing information, 5 pgs., AstraZeneca Pharmaceuticals LP, (Revised: Mar. 2017)(5 pages).
Eritsland J, Arnesen H, Gronseth K, et al. Effect of dietary supplementation with n-3 fatty acids on coronary artery bypass graft patency. Am. J. Cardiol. Jan. 1996 77 (1): 31-6.
Eritsland J, Arnesen H, Seljeflot I, et al. Long-term effects of n-3 polyunsaturated fatty acids on haemostatic variables and bleeding episodes in patients with coronary artery disease. Blood Coagul. Fibrinolysis Feb. 6, 1995 (1): 17-22.
Errata to the FDA Briefing Document Endocrinologic and Metabolic Drug Advisory Committee Meeting Oct. 16, 2013, 1 page.
Esposito, "Effect of a Mediterranean-Style Diet on Endothelial Dysfunction and Markers of Vascular Inflammation in the Metabolic Syndrome: A Randomized Trial", Journal of the American Medical Association, 2004, 292(12), 1440-1446.
Essentials Inc. press release, "Essentials Meets Primary Endpoint in Phase 2b Trial of DCCR for Treatement of Hypertriglyceridemia and is Granted Extensive Patent Coverage in the US," PR Newswire (May 17, 2009)(2 pages).
Exhibit A to Defendants' Joint Invalidity Contentions, 3:14-CV-02550-MLC-TJB (D.N.J.), 48 pages (Dec. 5, 2014).
Exhibit B to Defendants' Joint Invalidity Contentions, 3:14-CV-02550-MLC-TJB (D.N.J.), 6 pages (Dec. 5, 2014).

(56) References Cited

OTHER PUBLICATIONS

Exhibit C to Defendants' Joint Invalidity Contentions, 3:14-CV-02550-MLC-TJB (D.N.J.), 14 pages (Dec. 5, 2014).
Exhibit D to Defendants' Joint Invalidity Contentions, 3:14-CV-02550-MLC-TJB (D.N.J.), 19 pages (Dec. 5, 2014).
Exhibit E to Defendants' Joint Invalidity Contentions, 3:14-CV-02550-MLC-TJB (D.N.J.), 6 pages (Dec. 5, 2014).
Exhibit F to Defendants' Joint Invalidity Contentions, 3:14-CV-02550-MLC-TJB (D.N.J.), 10 pages (Dec. 5, 2014).
Exhibit G to Defendants' Joint Invalidity Contentions, 3:14-CV-02550-MLC-TJB (D.N.J.), 21 pages (Dec. 5, 2014).
Exhibit H to Defendants' Joint Invalidity Contentions, 3:14-CV-02550-MLC-TJB (D.N.J.), 10 pages (Dec. 5, 2014).
Exhibit I to Defendants' Joint Invalidity Contentions, 3:14-CV-02550-MLC-TJB (D.N.J.), 14 pages (Dec. 5, 2014).
Exhibit J to Defendants' Joint Invalidity Contentions, 3:14-CV-02550-MLC-TJB (D.N.J.), 13 pages (Dec. 5, 2014).
Exhibit K to Defendants' Joint Invalidity Contentions, 3:14-CV-02550-MLC-TJB (D.N.J.), 5 pages (Dec. 5, 2014).
Exhibit L to Defendants' Joint Invalidity Contentions, 3:14-CV-02550-MLC-TJB (D.N.J.), 5 pages (Dec. 5, 2014).
Exhibit M to Defendants' Joint Invalidity Contentions, 3:14-CV-02550-MLC-TJB (D.N.J.), 7 pages (Dec. 5, 2014).
Exhibit N To Defendants' Joint Invalidity Contentions, 3:14-CV-02550-MLC-TJB (D.N.J.), 15 pages (Dec. 5, 2014).
Exhibit O to Defendants' Joint Invalidity Contentions, 3:14-CV-02550-MLC-TJB (D.N.J.), 6 pages (Dec. 5, 2014).
Exhibit P To Defendants' Joint Invalidity Contentions, 3:14-CV-02550-MLC-TJB (D.N.J.), 17 pages (Dec. 5, 2014).
Exhibit Q to Defendants' Joint Invalidity Contentions, 3:14-CV-02550-MLC-TJB (D.N.J.), 64 pages (Dec. 5, 2014).
Faggin, E., et al., "Fish Oil Supplementation Prevents Neointima Formation in Nonhypercholesterolemic Balloon-Injured Rabbit Carotid Artery by Reducing Medial and Adventitial Cell Activation." Arterioscler. Thromb. Vasc. Biol., 20:152-163 (2000).
FDA Briefing Document, Endocrinologic and Metaboloic Drugs Advisory Committee Meeting, dated Oct. 16, 2013, available publicly at least as of Oct. 16, 2013, 115 pages.
FDA News Release, "FDA approves new orphan drug Kynamro to treat inherited cholesterol disorder," U.S. Food and Drug Administration, Protecting and Promoting Your Health (Jan. 29, 2013)(2 pages).
Fer, M., et al., "Metabolism of eicosapentaenoic and docosahexaenoic acids by recombinant human cytochromes P450." Archives of Biochemistry and Biophysics 471:116-125 (2008).
Ferns, G., et al., "Investigation and management of hypertriglyceridaemia." J. Clin. Pathol. 61:1174-1183 (2008).
Feron O, Dessy C, Desager JP, Balligand JL. Hydroxy-methylgluataryl-coenzyme a reductase inhibition promotes endothelial nitric oxide synthase activation through a decrease in caveolin abundance. Circulation. 2001;103:113-118.
Final Agenda for the Oct. 16, 2013 Meeting of the Endocrinologic and Metabolic Drugs Advisory Committee, 2 pages.
Final Meeting Roster for the Oct. 16, 2013 Meeting of the Endocrinologic and Metabolic Drugs Advisory Committee, 2 pages.
Final Questions for the Oct. 16, 2013 Meeting of the Endocrinologic and Metabolic Drugs Advisory Committee, 1 page.
Finnen et al., "Purification and characterisation of phospholipase A2 from human epidermis,", Biochemical Society Trans,19(2):91S, 1991.
Fischer, R., et al., "Dietary n-3 polyunsaturated fatty acids and direct renin inhibition improve electrical remodeling in a model of high human renin hypertension." Hypertension 51:540-546 (2008).
Fisher et al., Journal of Biological Chemistry (2001) 276(3) 27855-27863.
Flaten, H., et al., "Fish-oil concentrate: effects on variables related to cardiovascular disease." Am. J. Clin. Nutr. 52:300-306 (1990).
Food and Drug Administration (FDA), (2005) NIASPAN niacin extended release tablets.
Food and Drug Administration (FDA), (2005) Tablets ZOCOR® (SIMVASTATIN).
Ford, E.S. et al., "Hypertriglyceridemia and Its Pharmacologic Treatment Among US Adults." Arch, Intern. Med., 169(6): 572-78 (2009).
Frangou et al., "Efficacy of ethyl-eicosapentaenoic acid in bipolar depression: randomised double-blind placebo-controlled study," British Journ. Psychiatry, 188, 46-50 (2006).
Frey R, Muck W, Kirschbaum N, et al. Riociguat (BAY 63-2521) and warfarin: a pharmacodynamic and pharmacokinetic interaction study. J. Clin. Pharmacol. Jul. 2011 51 (7): 1051-60.
Frick, MH, et al., "Helsinki Heart Study. Primary prevention trial with gemfibrozil in middle-aged men with dyslipidaemia. Safety of treatment, changes in risk factors and incidence of coronary heart disease", N. Eng. J. Med., 317:1237-1245, (1987).
Friedewald, W.T., et al., "Estimation of the concentration of low-density lipoprotein cholesterol in plasma, without use of the preparative ultracentrifuge." Clin Chem.,18:499-502 (1972).
Friedman, A. N., et al., "Fish Consumption and Omega-3 Fatty Acid Status and Determinants in Long-Term Hemodialysis." Amer. J. Kidney Diseases, 47(6):1064-1071 (2006).
Frøyland et al., "Chronic administration of eicosapentaenoic acid and docosahexaenoic acid as ethyl esters reduced plasma cholesterol and changed the fatty acid composition in rat blood and organs." Lipids 31(2):169-78 (Feb. 1996).
Frøyland, L., et al., "Hypotriacylglycerolemic component of fish oil." Prostaglandins, Leukotrienes and Essential Fatty Acids 57 (4 & 5):387-388 (1997).
Furuta T, Shirai N, Sugimoto M, et al. Influence of CYP2C19 pharmacogenetic polymorphism on proton pump inhibitor-based therapies. Drug Metab. Pharmacokinet Jun. 20, 2005 (3): 153-67.
Galeano NF, Al-Haideri M, Keyserman F, Rumsey SC, Deckelbaum RJ. Small dense low density lipoprotein has increased affinity for LDL receptor-independent cell surface binding sites: a potential mechanism for increased atherogenicity. J. Lipid Res. 1998;39(6):1263-1273.
Gallagher et al., "Germline BRCA Mutations Denote a Clinicopathalogic Subset of Prostate Cancer," Amer. Assoc. Cancer Res. Clin Cancer Res., 16(7):2115-21 (2010).
Garber AJ, Abrahamson MJ, Barzilay JI, et al. American Association of Clinical Endocrinologists' comprehensive diabetes management algorithm 2013 consensus statement. Endocr. Pract. 2013;19(suppl 2):1-48.
Gardner CD, Fortmann SP, Krauss RM. Association of small low-density lipoprotein particles with the incidence of coronary artery disease in men and women. JAMA. 1996;276(11):875-881.
Garg, R., et al., "Niacin treatment increases plasma homocyst(e)ine levels", Am. Heart. J., 138:1082-1087, (1999).
Garnett, "Interactions with Hydroxymethylglutaryl-coenzyme A reductase inhibitors," Am J Health-Sys Pharm vol. 52, 1639-1645, (1995).
Genest, JJ, et al., "Familial lipoprotein disorders in patients with premature coronary artery disease", 85:2025-2033, (1992).
Geppert, et al. "Microalgal docosahexaenoic acid decreases plasma triacylglycerol in normolipidaemic vegetarians: a randomized trial." British Journal of Nutrition, 95, 779-786. (2006).
Gillies, et al. "Effect of a Novel Eicosapentaenoic Acid-Rich Oil on Serum Cholesterol in Man," DuPont 2010.
Ginsberg HN, Elam MB, Lovato LC, Crouse JR, 3rd, Leiter LA, Linz P, Friedewald WT, Buse JB, Gerstein HC, Probstfield J, Grimm RH, Ismail-Beigi F, Bigger JT, Goff DC, Jr., Cushman WC, Simons-Morton DG, Byington RP. Effects of combination lipid therapy in type 2 diabetes mellitus. N. Engl. J. Med. 2010;362:1563-1574.
Ginsberg HN. "Hypertriglyceridemia: new insights and new approaches to pharmacologic therapy," Am J Cardiol, 87:1174-1180 (2001).
Girotti A W. Lipid hydroperoxide generation, turnover, and effector action in biological systems. J. Lipid Res. 1998;39(8):1529-1542.
GISSI-Prevenzione Investigators, "Dietary Supplementation with n-3 Polyunsaturated Fatty Acids and Vitamin E after Myocardial Infarction: Results of the GISSI-Prevenzione Trial", The Lancet, 354:447-455, (Aug. 7, 1999).
Glod, "Recent Advances in the Pharmacotherapy of Major Depression", Arch. Psychiatr. Nurs., 10(6):355-364 (Dec. 1996).

(56) References Cited

OTHER PUBLICATIONS

Goldberg, A C: "Combination therapy of dyslipidemia," Current Treatment Options in Cardiovascular Medicine Aug. 2007 GB, vol. 9, No. 4, pp. 249-258 (2007).
Goodman & Gilman (Robert W. Mahley & Thomas P. Bersot) Drug Therapy for Hypercholesterolemia and Dyslipidemia, in Goodman & Gilman's The Pharmacological Basis fo Therapeutics 971 (Hardman et al., eds 10th ed. 2001)(32 pages).
Gordon, DJ. et al., High density lipoprotein cholesterol and cardiovascular disease: four prospective American studies. Circulation. 79: 8-15. (1989).
Gorriz JL et al., "Rhabdomyolysis and Acute Renal Failure Associated with Gemfibrozil Therapy," Nephron 74(2): 437-438 (1996).
Gosai, P. et al. Effect of omega-3-acid ethyl esters on the steady-state plasma pharmacokinetics of rosuvastatin in healthy adults. Expert Opin. Pharmacother. 9, 2947-2953 (2008).
Goto, Y., et al., "Clinical Pharmacological Trial of Ethyl Icosapentate (MND-21)—Dose Finding Study." Journal of Clinical Therapeutic & Medicines 8:1293-309 (1992).
Gould, A.L., et al., "Cholesterol reduction yields clinical benefit: impact of statin trials." Circulation, 97:946-952 (1998).
Greenblatt DJ, von Moltke LL. Interaction of warfarin with drugs, natural substances, and foods. J. Clin. Pharmacol. Feb. 2005 45 (2): 127-32.
Grenyer, Brin F.S., et al., "Fish Oil Supplementation in the Treatment of Major Depression: A Randomised Double-Blind Placebo-Controlled Trial", Progress in Neuro-Psychopharmacology & Biological Psychiatry, 31:1393-1396, (2007).
Griffin, M.D., et al., "Effects of altering the ratio of dietary n-6 to n-3 fatty acids on insulin sensitivity, lipoprotein size, and postprandial lipemia in men and postmenopausal women aged 45-70 y: the OPTILIP Study." Am J Clin Nutr 84:1290-8 (2006).
Grimsgaard et al., "Effects of Highly Purified Eicosapentaenoic Acid and Docosahexaenoic Acid on Hemodynamics in Humans" American Society for Clinical Nutrition, 68:52-9, (1998).
Grimsgaard, Kaare H. Bonaa, John-Bjarne Hansen, and Arne Nordoy, "Highly purified eicosapentaenoic acid and docosahexaenoic acid in humans have similar triacylglycerol-lowering effects but divergent effects on serum fatty acids" Am J Clin Nutr, 66:649-659, (1997).
Grundy S.M et al., Efficacy, safety, and tolerability of once-daily niacin for the treatment of dyslipidemia associated with type 2 diabetes: results of the Assessment of Diabetes Control and Evaluation of the Efficacy of Niaspan Trial. Arch. Intern. Med. 162: 1568-1576 (2002).
Grundy SM, et al. Implications of Recent Clinical Trials for the National Cholesterol Education Prgram Adult Treatment Panel III Guidelines, Circulation. 2004; 110:227-39.
Grundy, Scott M., "Low-Density Lipoprotein, Non-High-Density Lipoprotein, and Apolipoprotein B as Targets of Lipid-Lowering Therapy" Circulation. 106:2526-2529 (2002).
Guallar, E., et al., "Omega-3 fatty acids in adipose tissue and risk of myocardial infarction—The EURAMIC study." Arterioscler. Thromb. Vasc. Biol., 19:1111-1118 (1999).
Guillot, et al., "Increasing intakes of the long-chain omega-3 docosahexaenoic acid: effects on platelet functions and redox status in healthy men," The FASEV Journal, vol. 23, pp. 2909-2916 (2009).
Guizy, M., et al.,"ω-3 and ω-6 Polyunsaturated fatty acids block HERG channels." Am J Physiol Cell Physiol 289:C1251-C1260 (2005).
Gyarmathy, M., "Selection from the industrial manufacturing. 5th part: Gelatine capsules. 5/2 part: Soft gelatine capsules," Gyogyszereszet, vol. 38, No. 2, pp. 105-109 (1994) (with English summary).
Hakonarson, H., et al., "Effects of a 5-lipoxygenase-activating protein inhibitor on biomarkers associated with risk of myocardial infarction—a randomized trial." JAMA, 293(8):2245-56 (2005).
Hall, W. L., et al., "A high-fat meal enriched with eicosapentaenoic acid reduces postprandial arterial stiffness measured by digital volume pulse analysis in healthy men." J. Nutr. 138: 287-291 (2008).
Hamazaki et al., "Docosahexaenoic Acid-Rich Fish Oil Does Not Affect Serum Lipid Concentrations of Normolipidemic Young Adults", American Institute of Nutrition, 126(11):2784-2789, Nov. 1996.
Hamazaki et al., "Effects of Orally Administered Ethyl Ester of Eicosapentaenoic Acid (EPA: C20:5, omega-3) on PG12-Like Substance Production by Rat Aorta" Prostaglandins, vol. 23 No. 4, pp. 557-567 (1982).
Hamazaki T. et al., "Reduction of microalbuminuria in diabetics by Eicosapentaenoic acid ethyl ester" Lipids. 25 (9):542-5 (1990).
Hampel H, Abraham NS, El-Se rag HB. Meta-analysis: obesity and the risk for gastroesophageal reflux disease and its complications. Ann. Intern. Med. Aug. 2005 143 (3): 199-211.
Han, J. J., et al., "Enhancement of both reaction yield and rate of synthesis of structured triacylglycerol containing eicosapentaenoic acid under vacuum with water activity control." Lipids 34:989-995 (1999).
Hanasaki, K., et al., "Potent modification of low density lipoprotein by group X secretory phospholipase A2 is linked to macrophage foam cell formation." J. Biol. Chem. 277(32):29116-24 (2002).
Haney, E.M., et al., "Screening for lipid disorders in children and adolescents; Systematic evidence review for the U.S. Preventive Services Task Force (evidence synthesis)." No. 47. Rockville, MD: Agency for Healthcare Research and Quality, US Department of Health and Human Services; AHRQ Publication No. 07-0598-EF-1; Jul. 2007. Available at: http://www.uspreventiveservicestaskforce.org/uspstf07/chlipid/chlipidsyn.pdf. (Accessed Mar. 23, 2011)(573 pages).
Hannah, J., et al., "Effect of dietary fatty acids on LDL binding." Ann N Y Acad Sci., 683:178-182 (1993).
Hansen et al., "Comparative effects of prolonged intake of highly purified fish oils as ethyl ester or triglyceride on lipids, haemostasis and platelet function in normolipaemic men." Eur. J. Clin. Nutr. 47(7):497-507 (Jul. 1993).
Hansen, J.B., et al., "Effects of highly purified eicosapentaenoic acid and docosahexaenoic acid on fatty acid absorption, incorporation into serum phospholipids and postprandial triglyeridemia." Lipids 33:131-38 (1998).
Harris, "n-3 Fatty acids and lipoproteins: a comparison of results from human and animal studies," Lipids 31, 243-252 (1996).
Harris, W. S. et al. "Safety and efficacy of Omacor in severe hypertriglyceridemia," Journal of Cardiovascular Risk, 4:385-391 (1997).
Harris, W. S., "Fish oils and plasma lipid and lipoprotein metabolism in humans: a critical review." J Lipid Res. 30:785-807 (1989).
Harris, W. S., "The omega-3 index as a risk factor for coronary heart disease." Am J Clin Nutr 87:1997S-2002S (2008).
Harris, W. S., et al., "n-3 Fatty acids and urinary excretion of nitric oxide metabolites in humans." Am. J. Clin. Nutr., 65:459-64 (1997).
Harris, W. S., et al., "Influence of n-3 fatty acid supplementation on the endogenous activities of plasma lipases." Am. J. Clin. Nutr. 66:254-60 (1997).
Harris, W.S., "Expert opinion: omega-3 fatty acids and bleeding-cause for concern?" The American Journal of Cardiology 99(6A): 45C-46C (2007).
Harris, W.S., "n-3 Fatty acids and human lipoprotein metabolism: an update." Lipids 34:S257-S258 (1999).
Harris, W.S., "n-3 Fatty acids and serum lipoproteins: human studies." Am J Clin Nutr 65:1645S-54S (1997).
Harris, W.S., "Omega-3 fatty acids in cardiac biopsies from heart transplantation patients." Circulation 110;1645-1649 (2004).
Harris, W.S., et al., "Comparison of the effects of fish and fish-oil capsules on the n-3 fatty acid content of blood cells and plasma phospholipids." Am J Clin Nutr 86:1621-5 (2007).
Harris, W.S., et al., "Stearidonic acid increases the red blood cell and heart eicosapentaenoic acid content in dogs." Lipids 42:325-333 (2007).
Harris, W.S., et al., "Tissue n-3 and n-6 fatty acids and risk for coronary heart disease events." Atherosclerosis 193:1-10 (2007).
Hartweg, J., et al., "Potential impact of omega-3 treatment on cardiovascular disease in type 2 diabetes." Curr Opin Lipidol., 20:30-38 (2009).
Hata et al, Geriatric Medicine, 30 (5), 799-852, 1992 (with English introduction).

(56) References Cited

OTHER PUBLICATIONS

Hawthorne, et al., "High dose eicosapentaenoic acid ethyl ester: effects on lipids and neutrophil leukotriene production in normal volunteers." Br. J. Clin. Pharmac., vol. 30, 187-194 (1990).

Hayashi et al., Decreases in Plasma Lipid Content and Thrombotic Activity by Ethyl Icosapentate Purified from Fish Oiles, Current Therapeutic Research, vol. 56, No. 1, pp. 24-31 (1995).

Herbette L, Marquardt J, Scarpa A, Blasie JK. A direct analysis of lamellar x-ray diffraction from hydrated oriented multilayers of fully functional sarcoplasmic reticulum. Biophys. J. 1977;20(2):245-272.

Higashihara et al. "Effects of Eicosapentaenoic Acid on Biochemical Failure after Radical Prostatectomy for Prostate Cancer," in vivo 24:561-566 (2010).

Hilpert, K.F., et al., "Postprandial effect of n-3 polyunsaturated fatty acids on apolipoprotein B-containing lipoproteins and vascular reactivity in type 2 diabetes." Am J Clin Nutr 85:369-76 (2007).

Hirafuji, M., et al., "Docosahexaenoic acid potentiates interleukin-1beta induction of nitric oxide synthase through mechanism involving p44/42 MAPK activation in rat vascular smooth muscle cells." British Journal of Pharmacology 136:613-619 (2002).

Hirai, A., et al., "The effects of the oral administration of fish oil concentrate on the release and the metabolism of [14C] arachidonic acid and [14C] eicosapentaenoic acid by human platelets", Thromb. Res., 28:285-298, (1982).

Hirano T, Ito Y, Koba S, Toyoda M, Ikejiri A, Saegusa H, Yamazaki J, Yoshino G. Clinical significance of small dense low-density lipoprotein cholesterol levels determined by the simple precipitation method. Arterioscler. Thromb. Vasc. Biol. 2004;24(3):558-563.

Hirano, R., et al., "Regulation by long-chain fatty acids of the expression of cholesteryl ester transfer protein in HepG2 cells." Lipids, 36:401-406 (2001).

Hofacer R, et al., Omega-3 fatty acid deficiency increases stearoyl-CoA desaturase expression and activity indicates in rat liver: Positive association with non-fasting plasma triglyceride levels, Prostaglandins Leukot. Essent. Fatty Acids. 2012;86:71-7.

Hohenester, "Primary Biliary Cirrhosis," Semin Immunopathol. 31L:283-307, 285 (2009).

Holmeide, A. K., et al., "Oxidative degradation of eicosapentaenoic acid into polyunsaturated aldehydes." Tetrahedron 59:7157-7162 (2003).

Holub, B.J., PhD, "Fish Oils and Cardiovascular Disease", Canadian Medical Association Journal, 141(10):1063 (1989).

Hom et al., "Soft Gelatin Capsules II: Oxygen Permeability Study of Capsule Shells," J Pharm Sci. (1975) 64(5):851-857.

Hombeck, M., et al., "Biosynthesis of the algal pheromone fucoserratene by the freshwater diatom Asterionella formosa (Bacillariophyceae)." Tetrahedron 54:11033-11042 (1998).

Horrobin, D.F. The Phospholipid Concept of Psychiatric Disorders and its Relationship to the Neurodevelopmental Concept of Schizophrenia. In M. Peet (ed.) Phospholipid Spectrum Disorder in Psychiatry pp. 1-19 (1999).

Hoskins et al., "Combination use of statins and omega-3 fatty acids: an emerging therapy for combined hyperlipidemia," Abstract, 1(5): 579-591(13) (2006).

Howe, P.R.C., et al., "Equal antithrombotic and triglyceride-lowering effectiveness of eicosapentaenoic acid-rich and docosahexaenoic acid-rich fish oil supplements." Lipids 34:S307-S308 (1999).

HPs2-thrive Collaborative Group, "randomized placebo-controlled trial in 25 673 high-risk patients of er niacin/laroprant: Trial design, pre-specified muscle and liver outcomes, and reasons for stopping study treatment." Eur. Heart J. 2013;34:1279-1291.

Hruska MW, Amico JA, Langaee TY, Ferrell RE, Fitzgerald SM, Frye RF. The effect of trimethoprim on CYP2C8 mediated rosiglitazone metabolism in human liver microsomes and healthy subjects. Br. J. Clin. Pharmacol. 2005;59:70-79.

Hughes et al., "Fish oil produces an atherogenic lipid profile in hypertensive men," Atherosclerosis, 84, pp. 229-237 (1990).

Hulthe J, Hulten LM, Fagerberg B. Low adipocyte-derived plasma protein adiponectin CJ concentrations are associated with the metabolic syndrome and small dense low-density lipoprotein particles: atherosclerosis and insulin resistance study. Metab. Clin. Exp. 2003;52(12):1612-1614.

Huntington's Disease Drug Works—The DHA Dilemma http://hddrugworks.org/index2.php?option=com_content&task=view&id=185&pop=1&pa . . . Printed on Aug. 22, 2008.(2 pages).

Ignarro LJ, Buga GM, Wood KS, Byrnes RE, Chaudhuri G. Endothelium-derived relaxing factor produced and released from artery and vein is nitric oxide. Proc. Natl. Acad. Sci. USA. 1987;84:9265-9269.

Illingworth, DR, et al., "Comparative effects of lovastatin and niacin in primary hypercholesterolemia: A prospective trial", Arch. Int. Med., 154:1586-1595, (1994).

Inoue, I., et al., "Expression of peroxisome proliferator-activated receptor α (PPARα) in primary cultures of human vascular endothelial cells." Biochem. Biophys. Res. Comm., 246, 370-374 (1998).

Ishida, Y., et al., "α-Lipoic Acid and Insulin Autoimmune Syndrome." Diabeters Care, 30(9): 2240-41 (2007).

Isley, et al., "Pilot study of combined therapy with ω-3 fatty acids and niacin in atherogenic dyslipidemia," Journal of Clinical Lipidology, 1, 211-217 (2007).

Itoh et al., "Increased adinponectin secretion by highly purified eicosapentaenoic acid in rodent models of obesity and human obses subjects," Arterioscler. Thromb. Vasc. Biol., pp. 1918-1925 (together with online Supplements 1-15) (2007).

Jacob RF, Mason RP. Lipid peroxidation induces cholesterol domain formation in model membranes. J. Biol. Chem. 2005;280(47):39380-39387.

Jacob RF, Walter MF, Self-Medlin Y, Mason RP. Atorvastatin active metabolite inhibits oxidative modification of small dense low-density lipoprotein. J. Cardiovasc. Pharmacol. 2013;62(2):160-166.

Jacobson et al. "Hypertriglyceridemia and Cardiovascular Risk Reduction", Clinical Therapeutics, vol. 29 pp. 763-777 (2007).

Jacobson TA. Opening a new lipid "apo-thecary": incorporating apolipoproteins as potential risk factors and treatment targets to reduce cardiovascular risk. Mayo Clin. Proc. 2011;86:762-780.

Jacobson, T. Secondary Prevention of Coronary Artery Disease with Omega-3 Fatty Acids. Am J Cardiol; 98 [suppl]: 61i-70i (2006).

Jacobson, T.A., "Role of n-3 fatty acids in the treatment of hypertriglyceridemia and cardiovascular disease." Am J Clin Nutr 87:1981S-90S (2008).

Jacobson, T.A., et al., "Effects of eicosapentaenoic acid and docosahexaenoic acid on low-density lipoprotein cholesterol and other lipids: A review." J. Clin. Lipidology, vol. 6, pp. 5-18 (2012).

Jakus V, Reitbrock N. Advanced glycation end-products and the progress of diabetic vascular complications. Physiol. Res. 2004;53(2):131-142.

Jenner, "Presymptomatic Detection of Parkinson's Disease". J Neural Transm Suppl., 40:23-36. (Abstract only) (1993).

Jialal I, Devaraj S. Antioxidants and atherosclerosis: Don't throw out the baby with the bath water. Circulation. 2003;107:926-928.

Jialal, I., "Editorial: Remnant lipoproteins: measurement and clinical significance." Clinical Chemistry 48(2):217-219 (2002).

Jong et al., "Role of ApoCs in Lipoprotein Metabolism: Function Differences Between ApoC1, ApoC2, and ApoC3," Arteriosclerosis, Thrombosis and Vascular Biology. (1999) 19(3):472-484.

Journal of the Japanese Diabetes Society, "A Case of Familial Combined Hyperlipidemia Associated with Obesity, Type 2 Diabetes Mellitus and Severe Hypertriglyceridemia," 51(3), pp. 233-237 (Mar. 30, 2008) (with English abstract).

Jung, U.J., et al., n-3 Fatty acids and cardiovascular disease: mechanisms underlying beneficial effects. Am J Clin Nutr 87: 2003S-9S (2008).

Kamido et al., Lipid Composition of Platelets from Patients with Atherosclerosis:Effect of Purified Eicosapentaenoic Acid Ethyl Ester Administration, 1988, Lipids, 23, pp. 917-923 [Abstract only] (7 pages).

Kaminski WE, Jendraschak E, Kiefl R, et al. Dietary omega-3 fatty acids lower levels of platelet-derived growth factor mRNA in human mononuclear cells. Blood Apr. 1993 81 (7): 1871-9.

(56) References Cited

OTHER PUBLICATIONS

Kanayasu, T., et al., "Eicosapentaenoic acid inhibits tube formation of vascular endothelial cells in vitro." Lipids 26:271-276 (1991).
Kastelein et al., Omega-3 Free Fatty Acids for the Treatment of Severe Hypertriglyceridemia: The EpanoVa for Lowering Very High Triglycerides (EVOLVE) Trial, J. Clin. Lipidol. (JACL 597) 2013 (54 pages).
Katan, M. B., et al., "Kinetics of the incorporation of dietary fatty acids into serum cholesteryl esters, erythrocyte membranes, and adipose tissue: an 18-month controlled study." J. Lipid Res. 38: 2012-2022 (1997).
Katayama et al., "Efficacy and Safety of Ethyl Icosapentate (Epadel) Given for a Long Term Against Hyperlipidemia," Prog. Med., 21:457-467 (2001) (with English translation).
Kato, T., et al., "Palmitate impairs and eicosapentaenoate restores insulin secretion through regulation of SREBP-1c in pancreatic islets." Diabetes, 57(9):2382-2392 (2008) (published online May 5, 2008.).
Kawamura et al., "Effects of 4 weeks' intake of polyunsaturated fatty acid ethylester rich in eicosapentaenoic acid (ethylester) on plasma lipids, plasma and platelet phsopholipid fatty acid composition and platelet aggregation; a double blind study," Nihon Naika Gakkai Zasshi, 72(1):18-24 (1983).
Kawano, H., et al., "Changes in aspects such as the collagenous fiber density and foam cell size of atherosclerotic lesions composed of foam cells, smooth muscle cells and fibrous components in rabbits caused by all-cis 5, 8, 11, 14, 17-icosapentaenoic acid", J. Atheroscler. Thromb., 9:170-177, (2002).
Kawashima, H., et al., "Oral Administration of Dihomo-γ-Linolenic Acid Prevents Development of Atopic Dermatitis in NC/Nga Mice." Lipids 43:37-43 (2008).
Keech A, Simes RJ, Barter P, Best J, Scott R, Taskinen MR, Forder P, Pillai A, Davis T, Glasziou P, Drury P, Kesaniemi Y A, Sullivan D, Hunt D, Colman P, d'Emden M, Whiting M, Ehnholm C, Laakso M. Effects of long-term fenofibrate therapy on cardiovascular events in 9795 people with type 2 diabetes mellitus (the FIELD study): Randomised controlled trial. Lancet. 2005;366:1849-1861.
Kelley, D. S., et al., "Docosahexaenoic Acid Supplementation Decreases Remnant-Like Particle-Cholesterol and Increases the (n-3) Index in Hypertriglyceridemic Men." J. Nutr. 138: 30-35 (2008).
Kelley, et al., "Docosahexaenoic acid supplementation improves fasting and postprandial lip profiles in hypertriglyceridemic men." The American Journal of Clinical Nutrition, 86: 324-333 (2007).
Kellner-Weibel G, Yancey PG, Jerome WG, Walser T, Mason RP, Phillips MC, Rothblat GH. Crystallization of free cholesterol in model macrophage foam cells. Arterioscler. Thromb. Vasc. Biol. 1999;19(8):1891-1898.
Kendall BJ, Macdonald GA, Hayward NK, et al. The risk of Barrett's esophagus associated with abdominal obesity in males and females. Int. J. Cancer May 2013 132(9): 2192-9.
Kerr, S., Brosnan MJ, Mcintyre M, Reid JL, Dominiczak AF, Hamilton CA. Superoxide anion production is increased in a model of genetic hypertension role of the endothelium. Hypertension. 1999;33:1353-1358.
Kew, S., et al., "Effects of oils rich in eicosapentaenoic and docosahexaenoic acids on immune cell composition and function in healthy humans." Am J Clin Nutr 79:674-81 (2004).
Kholodov et al., "Clinical Pharmacokinetics," M. Medicine. (1985) pp. 89-98, 134-138, 160, 378-380 [with English Summary](27 pages).
Kim F, Tysseling KA, Rice J, Gallis B, Haji L, Giachelli CM, Raines EW, Corson MA, Schwartz MW. Activation of IKKbeta by glucose is necessary and sufficient to impair insulin signaling and nitric oxide production in endothelial cells. J. Mol. Cell. Cardiol. 2005;39(2):327-334.
Kim KA, Park PW, Kim HK, Ha JM, Park JY. Effect of quercetin on the pharmacokinetics of rosiglitazone, a CYP2C8 substrate, in healthy subjects. J. Clin. Pharmacol. 2005;45:941-946.

Kimura, F., et al., "Long-term supplementation of docosahexaenoic acid-rich, eicosapentaenoic acid-free microalgal oil in n-3 fatty acid-deficient rat pups." Biosci. Biotechnol. Biochem., 72(2):608-610 (2008).
Kinoshita, "Anti-hyperlipidemic agents," Nihon Rinsho, 60(5):968-74 (May 2002) (with English Abstract)(11 pages).
Kinsella, J.E., et al., "Dietary n-3 polyunsaturated fatty acids and amelioration of cardiovascular disease: possible mechanisms." Am J Clin Nutr 52:1-28 (1990).
Kitada, 9th Diabetes Drug and Drug Related Seminar Diabetes Q&A, Kanazawa Medical University, Diabetes and Endocrine Internal Medicine (http://plaza.umin.ac.jp/iby/etcdata/yakuyaku110410.pdf)(Apr. 10, 2011) (with English translation)(105 pages).
Knapp HR. Dietary fatty acids in human thrombosis and hemostasis. Am. J. Clin. Nutr. May 1997 65 (5 Suppl): 1687S-98S.
Knopp, R.H., et al., "Contrasting effects of unmodified and time-release forms of niacin on lipoproteins in hyperlipidemic subjects: clues to mechanism of action of niacin", Metabolism, 34:642-650, (1985).
Koba S, Hirano T, Ito Y, Tsunoda F, Yokota Y, Ban Y, Iso Y, Suzuki H, Katagiri T. Significance of small dense low-density lipoprotein-cholesterol concentrations in relation to the severity of coronary heart diseases. Atherosclerosis. 2006;189(1):206-214.
Kohno, M., et al., "Inhibition by Eicosapentaenoic Acid of Oxidized-LDL- and Lysophosphatidylcholine-Induced Human Coronary Artery Smooth Muscle Cell Production of Endothelin." J. Vasc. Res. 38:379-388 (2001).
Kojda G, Harrison DG. Interactions between no and reactive oxygen species: Pathophysiological importance in atherosclerosis, hypertension, diabetes and heart failure. Cardiovasc. Res. 1999;43:562-571.
Kojima, T, et al., "Long-term administration of highly purified eicosapentaenoic acid provides improvement of psoriasis." Dermatologica, 182:225-230 (1991).
Koroshetz, W.J. Huntington's Disease. In Samuels, M. (ed.) Office Practice of Neurology, pp. 654-661 (1996).
Kosonen, O., et al., "Inhibition by nitric oxide-releasing compounds of E-selectin expression in and neutrophil adhesion to human endothelial cells." European Journal of Pharmacology 394:149-156 (2000).
Koyama et al., Plaque Reduction and Stabilization Observed in Borderline Diabetes Using Coronary CT Angiogram During Administration of Purified Eicosapentaenoic Acid (EPA) Ther. Res. 31(2):219-225 (Feb. 2010) (with English translation)(20 pages).
Krauss RM. Heterogeneity of plasma low-density lipoproteins and atherosclerosis risk. Curr. Opin. Lipidol. 1994;5(5):339-349.
Kris-Etherton, P. M., et al., "Omega-3 Fatty Acids and Cardiovascular Disease—New Recommendations From the American Heart Association." Arterioscler Thromb Vasc Biol. 23:151-152 (2003).
Kris-Etherton, et al., "Fish Consumption, Fish Oil, Omega-3 Fatty Acids, and Cardiovascular Disease" Circulation, 106:2747-2757 (2002).
Krzynowek et al., "Purification of Omega-3 Fatty Acids from Fish Oils Using HPLC: An Overview," National Marine Fisheries—Proceedings of the first joint conference of the Tropical and Subtropical Fisheries Technological Soceity of the Americas with the Atlantic Fisheries Technological Society, pp. 74-77 (1988).
Ku, K., et al., "Beneficial Effects of to-3 Fatty Acid Treatment on the Recovery of Cardiac Function After Cold Storage of Hyperlipidemic Rats." Metabolism, 48(10):123-1209 (1999).
Kunimoto M, Inoue K, Nojima S. Effect of ferrous ion and ascorbate-induced lipid peroxidation on liposomal membranes. Biochem. Biophys.Acta. 1981;646(1):169-178.
Kurabayashi, T., et al., "Eicosapentaenoic acid effect on hyperlipidemia in menopausal Japanese women." Obstet Gynecol 96:521-8 (2000).
Labor Diagnostik Karlsruhe, "Target Values of Lipid Metabolism [Recommendation for lipid plasma levels in Germany]," (exact publication date unknown; circa 2006) (with English abstract)(4 pages).
Lada et al., "Associations of Low Density Lipoprotein Particle Compositions with Atherogenicity," Curr. Opin. Lipidol. (2004) 15(1):19-24.

(56) References Cited

OTHER PUBLICATIONS

Lai, E., et al., "Suppression of niacin-induced vasodilation with an antagonist to prostaglandin D2 receptor subtype 1", Clin. Pharm. & Ther., 81:849-857, (2007).
Laidlaw, M., et al., "Effects of supplementation with fish oil-derived n-3 fatty acids and γ-linolenic acid on circulating plasma lipids and fatty acid profiles in women." Am J Clin Nutr 77:37-42 (2003).
Lamb RE, Goldstein BJ. Modulating an Oxidative-Inflammatory Cascade: Potential New Treatment Strategy for Improving Glucose Metabolism, Insulin Resistance, and Vascular Function. Int. J. Clin. Pract. 2008;62(7): 1087-1095.
Lamharzi N, Renard CB, Kramer F, Pennathur S, Heinecke JW, Chait A, Bomfeldt KE. Hyperlipidemia in concert with hyperglycemia stimulates the proliferation of macrophages in atherosclerotic lesions: potential role of glucose-oxidized LDL. Diabetes. 2004;53(12):3217-3225.
Landmesser U, Dikalov S, Price SR, McCann L, Fukai T, Holland SM, Mitch WE, Harrison DG. Oxidation of tetrahydrobiopterin leads to uncoupling of endothelial cell nitric oxide synthase in hypertension. J. Clin. Invest. 2003;111:1201-1209.
Larsen, L.N., et al., "Heneicosapentaenoate (21:5n-3): Its incorporation into lipids and its effects on arachidonic acid and eicosanoid Synthesis." Lipids 32:707-714 (1997).
Laufs et al., "Upregulation of endothelial nitric oxide synthase by hmg coa reductase inhibitors," Circulation (1998) 97:1129-1135.
Law, M.R., et al., "Quantifying effect of statins on low density lipoprotein cholesterol, ischaemic heart disease, and stroke: systematic review and meta-analysis." Br Med J., 326:1423-1427 (2003).
Lawson et al., "Human absorption of fish oil fatty acids as triacylglycerols, free acids or ethyl esters," Biochemical and Biophysical Research Communications 152(1):328-335 (Apr. 15, 1988).
Leaf, "Hypertriglyceridemia: A Guide to Assessment and Treatment," Hospital Physician 17-23 (Sep. 2008).
Leaf, A., "Historical overview of n3 fatty acids and coronary heart disease." Am J Clin Nutr 87:1978S-80S. (2008).
Lee and G.Y.H. Lip, "The Role of Omega-3 Fatty Acids in the Secondary Prevention of Cardiovascular Disease", Q J Med, 96:465-480, (2003).
Lee C, Sigari F, Segrado T, Horkko S, Hama S, Subbaiah PV, Miwa M, Navab M, Witztum JL, Reaven PD. All ApoB-containing lipoproteins induce monocyte chemotaxis and adhesion when minimally modified. Modulation of lipoprotein bioactivity by platelet-activating factor acetylhydrolase. Arterioscler. Thromb. Vasc. Biol. 1999; 19(6): 1437-1446.
Lee, J.H., et al., "Omega-3 fatty acids for cardioprotection." Mayo Clin Proc., 83(3):324-332 (2008).
Leigh-Firbank et al., "Eicosapentaenoic acid and docosahexanoic acid from fish oils: differential associations with lipid responses," Br. J. Nutr. 87:435-445 (2002).
Lemaitre, R.N., et al., "n-3 Polyunsaturated fatty acids, fatal ischemic heart disease, and nonfatal myocardial infarction in older adults: the Cardiovascular Health Study." Am J Clin Nutr 77:319-25 (2003).
Leonard, Brian E., "Neurological Aspects", Fundamentals of Psychopharmacology,186-187, (1997).
Leucht, S., et al., Schizophrenia Research, vol. 35, "Efficacy and extrapyramidal side-effects of the new antipsychotics olanzapine, quetiapine, risperidone, and sertindole compared to conventional antipsychotics and placebo. A meta-analysis of randomized controlled trials", pp. 51-68, (1999).
Li, D., et al., "Effect of dietary a-linolenic acid on thrombotic risk factors in vegetarian men." Am J Clin Nutr 69:872-82 (1999).
Li, H., et al., "EPA and DHA reduce LPS-induced inflammation responses in HK-2 cells: Evidence for a PPAR-γ-dependent mechanism." Kidney Int'l. 67:867-74 (2005).
Libby, "Inflammation and atherosclerosis," Nature (2002) 420(6917):868-874.
Lien, E.L., "Toxicology and safety of DHA." Prostaglandins Leukot Essent Fatty Acids., 81:125-132 (2009).

Lin, Pao-Yen, M.D., et al., "A Meta-Analytic Review of Double-Blind, Placebo-Controlled Trials of Antidepressant Efficacy of Omega-3 Fatty Acids", Psychiatry, 1056-1061 (Jul. 2007).
Lin, Y., et al., "Differential effects of eicosapentaenoic acid on glycerolipid and apolipoprotein B metabolism in primary human hepatocytes compared to HepG2 cells and primary rat hepatocytes." Biochimica et Biophysica Acta 1256:88-96 (1995).
Lindsey, S., et al., "Low density lipoprotein from humans supplemented with n-3 fatty acids depresses both LDL receptor activity and LDLr mRNA abundance in HepG2 cells." J Lipid Res., 33:647-658 (1992).
Lipitor [package insert]. New York, NY: Parke-Davis (2012). (22 pages).
Lipitor [product information] Dublin, Ireland: Pfizer Inc. ( 2007). (18 pages).
Liu et al., "Effects of stable fish oil and simvastatin on plasma lipoproteinc in patients with hyperlipidemia," Nutrion Res. , vol. 23, pp. 1027-1034 (2003).
Liu X, et al., Stearoyl CoA Desaturase 1: Role in Cellular Inflammation and Stress, Adv. Nutr. 2011;2:15-22.
Lohmussaar, E., et al., "ALOX5AP Gene and the PDE4D Gene in a Central European Population of Stroke Patients." Stroke, 36:731-736 (2005).
Lovaza (omega-3-acid ethyl esters) Capsules, Prescribing information, GlaxoSmithKline (Nov. 2008).(9 pages).
Lovaza [package insert]. Research Triangle Park, NC: GlaxoSmithKline (2012). (14 pages).
Lovaza Side Effects, web archived webpage, archived from Drugs.com website on (Jul. 31, 2010) Retrieved from URL <https://web.archive.org/web/20100731021902/https://www.drugs.com/sfx/lovaza-side-effects.html> (4 pages)(Jul. 2010).
Lovaza, (omega-3-acid ethyl esters) Capsules, Prescribing information Smith Kline Beechum (Jul. 2009).(17 pages).
Lovaza, GlaxoSmithKline, Lovaza Prescribing Information, Jun. 2008 [retrieved from the internet Jun. 6, 2012 <https://web.archive.org/web/20090206170311/http://us.gsk.com/products/assets/us_lovaza.pdf>]; Table 3, p. 1, section entitled 'Description;' p. 3, section entitled 'Very High Triglycerides: Monotherapy;' p. 4 section entitled 'Indications and Usage' and 'Information for Patients.' (12 pages).
LOVAZA® (omega-3-acid ethyl esters) Capsules, Prescribing information,GlaxoSmithKline, (Dec. 2010)(12 pages).
Lovaza®, Physicians' Desk Reference 2699-2701 (62d ed., 2008). (4 pages).
Lovegrove et al., "Moderate fish-oil supplementation reverses low-platelet, long chain n-3 polyunsaturated fatty acid status and reduced plasma triacylglycerol concentrations in British Indo-Asians," Am. J. Clin. Nutr., 79:974-982 (2004).
Lu, G., et al., "Omega-3 fatty acids alter lipoprotein subfraction distributions and the in vitro conversion of very low density lipoproteins to lowdensity lipoproteins." J Nutr Biochem., 10:151-158 (1999).
Lucas, M., et al., "Ethyl-eicosapentaenoic acid for the treatment of psychological distress and depressive symptoms in middle-aged women: a double-blind, placebo-controlled, randomized clinical trial." Am J Clin Nutr 89:641-51 (2009).
Luria, MH, "Effect of low-dose niacin on high-density lipoprotein cholesterol and total cholesterol/high density lipoprotein cholesterol ratio", Arch. Int. Med., 148:2493-2495, (1998).
Lvovich V, Scheeline A. Amperometric sensors for simultaneous superoxide and hydrogen peroxide detection. Anal. Chem. 1997;69:454-462.
Madhavi et al., "Effect of n -6 and n -3 fatty acids on the survival of vincristine sensitive and resistant human cervical carcinoma cells in vitro", Cancer Letters, vol. 84. No. 1, pp. 31-41 (1994).
Madsen, L., et al., "Eicosapentaenoic and Docosahexaenoic Acid Affect Mitochondrial and Peroxisomal Fatty Acid Oxidation in Relation to Substrate Preference." Lipids 34:951-963 (1999).
Mak IT, Weglicki WB. Antioxidant properties of calcium channel blocking drugs. Methods Enzymol. 1994;234:620-630.

(56) References Cited

OTHER PUBLICATIONS

Maki, K.C., et al., "Baseline lipoprotein lipids and low-density lipoprotein cholesterol response to prescription omega-3 acid ethyl ester added to simvastatin therapy." Am J Cardiol., 105:1409-1412 (2010).

Maki, PhD, et al., "Lipid Responses to a Dietary Docosahexaenoic Acid Supplement in Men and Women with Below Average Levels of High Density Lipoprotein Cholesterol." Journal of the American College of Nutrition, vol. 24, No. 3, 189-199 (2005).

Malinowski et al., "Elevation of Low-Density Lipoprotein Cholesterol Concentration with Over-the-Counter Fish Oil Supplementation." Annals of Pharmacotherapy 41:1296-1300 (Jul./Aug. 2007).

Malinski T, Taha Z. Nitric oxide release from a single cell measured in situ by a porphyrinic-based microsensor. Nature. 1992;358:676-678.

Mallat, Z., et al., "Apoptosis in the vasculature: mechanisms and functional importance." British Journal of Pharmacology 130:947-962 (2000).

Mallat, Z., et al., "Protective role of interleukin-10 in atherosclerosis." Circ. Res. 85:e17-e24 (1999).

Marangell, Lauren B., M.D., et al., "A Double-Blind, Placebo-Controlled Stury of the Omega-3 Fatty Acid Docosahexaenoic Acid in the Treatment of Major Depression", Am. J. Psychiatry, 160(5):996-998, (May 2003).

Marckmann, P., "Fishing for heart protection." Am J Clin Nutr, 78:1-2 (2003).

Marder, "An Approach to Treatment Resistance in Schizophrenia," British Journ. Psychiatry, 37:19-22 (1999).

Margolis, Simeon "What is Hyperlipidemia?" (http:www.healthcommunities.com/highcholesterol/whatishyperlipidemia.shtml, accessed Oct. 20, 2015, published Aug. 25, 2011)(4 pages).

Martinez-Gonzalez J, Raposo B, Rodriguez C, Badimon L. 3-hydroxy-3-methylglutaryl coenzyme a reductase inhibition prevents endothelial no synthase downregulation by atherogenic levels of native ldls: Balance between transcriptional and posttranscriptional regulation. Arterioscler. Thromb. Vasc. Biol. 2001;21:804-809.

Martinez-Gonzalez, Jose et al., "Estatinas y acidos grasos omega-3. Disminucion de la mortalidad cardiovascular dependiente e independiente de la reduccion de la colesterolemia," (2006) Rev Esp Cardiol Suppl., 6(D):20D-30D [with English abstract].

Martin-Jadraque, R. et al., Effectiveness of low dose crystalline nicotinic acid in men with low density lipoprotein cholesterol levels. Arch. Int. Med. 156: 1081-1088. (1996).

Martz, "Moving Upstream in Huntington's," Science-Business eXchange, 2 pgs., 2008.

Mason et al., "Comparative lipid antioxidant effects of omega-3 fatty acids in combination with HMG-CoA reductase inhibitors," Journ. Clin. Lipidology (2011) 5(3):20.

Mason et al., "Direct evidence for cholesterol crystalline domains in biological membranes: role in human pathobiology," Biochimica et Biophysica Acta 198-207 (Mar. 10, 2003).

Mason et al., "Eicosapentaenoic Acid (EPA) inhibits the formation of membrane cholesterol crystalline domains by a potent antioxidant mechanism," Journ. Clin. Lipid., 7(3): 272-273 (2013) [Abstract only].

Mason et al., "Eicosapentaenoic acid inhibits glucose-induced membrane cholesterol crystalline domain formation through a potent antioxidant mechanism," Biochim. Biophy. Acta., 1848(2):502-9, (Feb. 2015).

Mason et al., "Eicosapentaenoic Acid Inhibits Oxidation of ApoB-containing Lipoprotein Particles of Different Size In Vitro When Administered Alone or in Combination With Atorvastatin Active Metabolite Compared With Other Triglyceride-lowering Agents," J. Cardiovasc. Pharmacol., 68(1):33-40 (Jul. 2016).

Mason et al., "Eicosapentaenoic acid reduces membrane fluidity, inhibits cholesterol domain formation, and normalizes bilayer width in atherosclerotic-like model membranes," Biochim. Biophy. Acta., 1858(12):3131-3140 (Dec. 2016).

Mason RP, Gonye GE, Chester DW, Herbette LG. Partitioning and location of Bay K 8644, 1,4-dihydropyridine calcium channel agonist, in model and biological membranes. Biophys. J. 1989;55(4):769-778.

Mason RP, Jacob RF, Kubant R, Walter MF, Bellamine A, Jacoby A, Mizuno Y, Malinski T. Effect of enhanced glycemic control with saxagliptin on endothelial nitric oxide release and CD40 levels in obese rats. J. Atheroscler. Thromb. 2011;18:774-783.

Mason RP, Jacob RF. Membrane microdomains and vascular biology: Emerging role in atherogenesis. Circulation. May 6, 2003; 107:2270-2273.

Mason RP, Kalinowski L, Jacob RF, Jacoby AM, Malinski T. Nebivolol reduces nitroxidative stress and restores nitric oxide bioavailability in endothelium of black americans. Circulation. 2005;112:3795-3801.

Mason RP, Kubant R, Heeba G, Jacob RF, Day CA, Medlin YS, Funovics P, Malinski T. Synergistic effect of amlodipine and atorvastatin in reversing ldl-induced endothelial dysfunction. Pharm. Res. 2008;25:1798-1806.

Mason RP, Walter MF, Day CA, Jacob RF. Active metabolite of atorvastatin inhibits membrane cholesterol domain formation by an antioxidant mechanism. J. Biol. Chem. 2006;281(14):9337-9345.

Mason RP, Walter MF, Day CA, Jacob RF. Intermolecular differences for HMG-CoA reductase inhibitors contribute to distinct pharmacologic and pleiotropic actions. Am. J Cardiol. 2005;96(5A):11F-23F.

Mason RP, Walter MF, Jacob RF. Effects of hmg-coa reductase inhibitors on endothelial function: Role of microdomains and oxidative stress. Circulation. 2004;109:II34-II41.

Mason RP, Walter MF, Mason PE. Effect of oxidative stress on membrane structure: Small angle x-ray diffraction analysis. Free Radic. Biol. Med. 1997;23(3):419-425.

Mason RP. Molecular basis of differences among statins and a comparison with antioxidant vitamins. Am. J. Cardiol. 2006;98:34P-41P.

Mataki et al., "Effect of Eicosapentaenoic Acid in Combination with HMG-CoA Reductase Inhibitor on Lipid Metabolism," Int. Med. J. 5(1):35-36 (Mar. 1998).

Mater, M.K., et al., "Arachidonic acid inhibits lipogenic gene expression in 313-L1 adipocytes through a prostanoid pathway." J. Lipid Res. 39:1327-1334 (1998).

Matsumoto, M., et al., "Orally administered eicosapentaenoic acid reduces and stabilizes atherosclerotic lesions in ApoE-deficient mice." Atherosclerosis, 197(2):524-533 (2008).

Matsuzaki et al., "Incremental Effects of Eicosapentaenoic Acid on Cardiovascular Events in Statin-Treated Patients with Coronary Artery Disease," Circ. J. 73:1283-1290 (2009).

Matsuzawa, Y., et al., "Effect of Long-Term Administration of Ethyl Icosapentate (MND-21) in Hyperlipaemic Patients," J. Clin Therapeutic & Medicines, 7: 1801-16 (1991).

Mattson MP. Modification of ion homeostasis by lipid peroxidation: roles in neuronal degeneration and adaptive plasticity. Trends Neurosci. 1998;21(2):53-57.

Mayatepek, E., et al., The Lancet, vol. 352, Leukotriene C4-synthesis deficiency: a new inborn error of metabolism linked to a fatal developmental syndrome, pp. 1514-1517 (1998).

Mayo Clinic at http://www.mayoclinic.org.diseases-conditions/high-blood-cholesterol/in-depth/cholesterol (2014)(5 pages).

McElroy, S.L., et al., "Clozapine in the Treatment of Psychotic Mood Disorders, Schizoaffective Disorder, and Schizophrenia", Journal of Clinical Psychiatry, vol. 52, No. 10, pp. 411-414 (1991).

McIntyre M, Hamilton CA, Rees DD, Reid JL, Dominiczak AF. Sex differences in the abundance of endothelial nitric oxide in a model of genetic hypertension. Hypertension. 1997;30:1517-1524.

McKenney et al., "Prescription omega-3 fatty acids for the treatment of hypertriglyceridemia," Am. J. Health Syst. Pharm., 64(6):595-605 (2007).

McKenney et al., CMRO, "Comparison of the efficacy of rosuvastatin versus atorvastatin, simvastatin and pravastatin in achieving lipid goals: results from the STELLAR trial", 689-98 (2003).

McKenney, J., "Niacin for dyslipidemia: considerations in product selection", Am. J. Health Syst. Pharm., 60:995-1005, (2003).

(56) References Cited

OTHER PUBLICATIONS

McKenney, J.M. et al. Study of the pharmacokinetic interaction between simvastatin and prescription omega-3-acid ethyl esters. J. Clin. Pharmacol. 46, 785-791 (2006).
McKenney, James et al., "Role of prescription omega-3 fatty acids in the treatment of Hypertriglyceridemia," Pharmacotherapy, LNKD—Pubmed: 17461707, vol. 27, No. 5, pp. 715-728 (2007).
McKeone et al., "Alterations in serum phosphatidylcholine fatty acyl species by eicosapentaenoic and docosahexaenoic ethyl esters in patients with severe hypertriglyceridemia." J. Lipid Res. 38:429-436 (1997).
McMurchie, E.J., et al., "Incorporation and effects of dietary eicosapentaenoate (20 : 5( n-3)) on plasma and erythrocyte lipids of the marmoset following dietary supplementation with differing levels of linoleic acid." Biochimica et Biophysics Acta, 1045:164-173 (1990).
McNamara JR, et al., Remnant-like particle (RLP) Cholesterol is an independent cardiovascular disease risk factor in women: results from the Framingham Heart Study, Atherosclerosis, vol. 154(1), pp. 229-236 (2001).
MedlinePlus. "Coronary heart disease," Available at: https://medlineplus.gov/ency/article/007115.htm (review date Jul. 14, 2015)(accessed Sep. 2, 2016)(5 pages).
Menuet, R. et al., "Importance and management of dyslipidemia in the metabolic syndrome," American Journal of the Medical Sciences Dec. 2005 US, vol. 33, No. 6, pp. 295-302 (2005).
Merched, A.J., et al., "Atherosclerosis: evidence for impairment of resolution of vascular inflammation governed by specific lipid mediators." FASEB J. 22:3595-3606 (2008).
Merkl et al., "Antisense Oligonucleotide Directed to Human Apolipoprotein B-100 Reduces Lipoprotein(a) Levels and Oxidized Phospholipids on Human Apolipoprotein B-100 Particles in Lipoprotein(a) Transgenic Mice," Circulation, vol. 118, pp. 743-753 (2008).
Mesa, M., "Effects of oils rich in Eicosapentaenoic and docosahexaenoic acids on the oxidizability and thrombogenicity of low-density lipoprotein," Artherosclerosis 175, pp. 333-343 (2004).
Metcalf, R.G. et al., "Effect of dietary n-3 polyunsaturated fatty acids on the inducibility of ventricular tachycardia in patients with ischemic cardiomyopathy." Am J Cardiol 101:758-761 (2008).
Metcalf, R.G., et al., "Effects of fish-oil supplementation on myocardial fatty acids in humans." Am J Clin Nutr 85:1222-28 (2007).
Meyer, et al., "Dose-Dependent Effects of Docosahexaenoic Acid Supplementation on Blood Lipids in Statin-Treated Hyperlipidaemic Subjects." Lipids, 42:109-115 (2007).
Meyers, et al., "Nicotinic acid induces secretion of prostaglandin D2 in human macrophages: An in vitro model of the niacin-flush", Atherosclerosis, 192:253-258, (2007).
Micheletta F, Natoli S, Misuraca M, Sbarigia E, Diczfalusy U, Iuliano L. Vitamin E supplementation in patients with carotid atherosclerosis: Reversal of altered oxidative stress in plasma but not in plaque. Arterioscler. Thromb. Vasc. Biol. 2004;24:136-140.
Michos et al., "Niacin and Statin Combination Therapy for Atherosclerosis Regression and Prevention of Cardiovascular Disease Events," Journ. Amer. Coll. Cardiol., vol. 59, No. 23:2058-2064 (2012).
Mii, S., et al., "Perioperative use of eicosapentaenoic acid and patency of infrainguinal vein bypass: a retrospective chart review." Curr Ther Res Clin Exp. 68:161-174 (2007).
Miles, et al., "Effect of orlistat in overweight and obese patients with type 2 diabetes treated with metformin," Diabetes Care, 25(7):1123-1128 (2002).
Miller AK, DiCicco RA, Freed MI. The effect of ranitidine on the pharmacokinetics of rosiglitazone in healthy adult male volunteers. Clin. Ther. 2002;24:1062-1071.
Miller AK, Inglis AM, Culkin KT, Jorkasky DK, Freed MI. The effect of acarbose on the pharmacokinetics of rosiglitazone. Eur. J. Clin. Pharmacol. 2001;57:105-109.
Miller M, Stone NJ, Ballantyne C, et al. Triglycerides and cardiovascular disease: a scientific statement from the American Heart Association. Circulation. 2011;123:2292-2333.
Miller, M., et al., "Impact of lowering triglycerides on raising HDL-C in hypertriglyceridemic and non-hypertriglyceridemic subjects." International Journal of Cardiology 119:192-195 (2007).
Minihane, A.M., et al., "ApoE polymorphism and fish oil supplementation in subjects with an atherogenic lipoprotein phenotype." Arterioscler. Thromb. Vasc. Biol. 20:1990-1997 (2000).
Mishra, A., et al., "Oxidized omega-3 fatty acids inhibit NF-κB activation via a PPARα-Dependent Pathway." Arterioscler Thromb Vasc Biol. 24:1621-1627 (2004).
Missouri DUReport, Statin Therapy (Oct./Nov. 2003) Drug Use Review Newsletter 8(6):1-9.
Mita, T. et al., Eicosapentaenoic acid reduces the progression of carotid intima-media thickness in patients with type 2 diabetes, Atherosclerosis 191:162-167 (2007).
Mizota M, Katsuki Y, Mizuguchi K, Endo S, Miyata H, Kojima M, Kanehiro H et al. "Pharmacological studies of eicosapentaenoic acid ethylester (EPA E) on high cholesterol diet-fed rabbits," Nippon Yakurigaku Zasshi, 91:255-66 (1988) (with English abstract).
Mizota M, Katsuki Y, Mizuguchi K, Endo S, Miyata H, Kojima M, Kanehiro H et al. "The effects of eicosapentaenoic acid ethylester (EPA E) on arterial thrombosis in rabbits and vascular lesions in rats," Nippon Yakurigaku Zasshi, 91:81-9 (1988)(with English abstract).
Mizuguchi K, Yano T, Kojima M, Tanaka Y, Ishibashi M, Masada A, Sato M et al. "Hypolipidemic effect of ethyl all-cis-5,8,11,14,17-eicosapentaenoate (EPA-E) in rats," Jpn J Pharmacol., 59:3307-12 (1992).
Mizuguchi, K., et al., "Ethyl all-cis-5,8,11,14,17-icosapentaenoate modifies the biochemical properties of rat very low-density lipoprotein." European Journal of Pharmacology, 231:221-227 (1993).
Mizuguchi, K., et al., "Mechanism of the lipid-lowering effect of ethyl all-cis-5,8,11,14,17-icosapentaenoate." European Journal of Pharmacology, 231:121-127 (1993).
Mochida Press Release, Pharmaceutical Col., Ltd.: Conclusion of Distributorship Agreement Concerning Switch-OTC Drug for Hyperlipidemia Treatment, Epadel, (2009)(1 page).
Mochida, Announcement, "Mochida Announces Completion of "JELIS" Major Clinical Trial for Epadel," Mar. 22, 2005 (2 pages).
Mochida's Epadel Reduces Risk of Stroke Recurrence—New Results of JELIS Major Clinical Trial, JCNNetwork Newswire Nov. 13, 2006 (2 pages).
Mora, S., et al., "LDL particle subclasses, LDL particle size, and carotid atherosclerosis in the Multi-Ethnic Study of Atherosclerosis (MESA)." Atherosclerosis. 2007;192:211-217 (2007).
Mori et al., "Differential Effects of Eicosapentaenoic Acid and Docosahexaenoic Acid on Vascular Reactivity of the Forearm Microcirculation in Hyperlipidemic, Overweight Men," Circulation, 102:1264-1269 (2000).
Mori TA, Woodman RJ. "The independent effects of eicosapentaenoic acid and docosahexaenoic acid on cardiovascular risk factors in humans," Curr Opin Clin Nutr Metab Care 2006; 9:95-104 (2006).
Mori, et al., "Purified Eicosapentaenoic and docosahexaenoic acids have differential effects on serum lipids and lipoproteins, LDL particle size, glucose, and insulin in mildly hyperlipidemic men," Am J Clin Nutr 71:1085-1094 (2000).
Mori, T. et al., Effect of Eicosapentaenoic acid and docosahexaenoic acid on oxidative stress and inflammatory markers in treated-hypertensive type 2 diabetic subjects, Free Radical Biology & Medicine, vol. 35, No. 7, pp. 772-781 (2003).
Mori, Trevor A., et al., "Docosahexaenoic Acid but Not Eicosapentaenoic Acid Lowers Ambulatory Blood Pressure and Heart Rate in Humans", Hypertension, 34(2):253-60 (Aug. 1999).
Morita, I., et al., "Effects of purified eicosapentaenoic acid on arachidonic acid metabolism in cultured murine aortic smooth muscle cells, vessel walls and platelets." Lipids 18:42-490 (1983).
Morrow, JD, "Release of markedly increased quantities of prostaglandin D2 in vivo in humans following the administration of nicotinic acid", Prostaglandins, 38:263-274, (1989).
Morton, R.E., "Specificity of lipid transfer protein for molecular species of cholesteryl ester." J Lipid Res., 27:523-529 (1986).

(56) References Cited

OTHER PUBLICATIONS

Mosher LR et al., "Nicotinic Acid Side Effects and Toxicity: A review," Am J Psychiat., 126: 1290-1296 (1970).
Mostad et al., "Effects of Marine N-3 Fatty Acid Supplementation on Lipoprotein Subclasses Measured by Nuclear Magnetic Resonance in Subjects with Type II Diabetes," European Journ. Clin. Nutr., 62(3):419-429 (2007).
Mostad, I.L, et al., "Effects of n-3 fatty acids in subjects with type 2 diabetes: reduction of insulin sensitivity and time-dependent alteration from carbohydrate to fat oxidation." Am J Clin Nutr 84:540-50 (2006).
Mozaffarian et al., "Omega-3 fatty acids and cardiovascular disease: effects on risk factors, molecular pathways and clinical events," J. Am. Coll. Cardiol. (2011) 58(2):2047-2067.
Mozaffarian, "JELIS, fish oil, and cardiac events," www.thelancet.com vol. 369, pp. 1062-1063 (2007).
Mozaffarian, D., "Fish and n-3 fatty acids for the prevention of fatal coronary heart disease and sudden cardiac death." Am J Clin Nutr, 87:1991S-6S (2008).
Mozaffarian, D., et al., "Dietary fish and ω-3 fatty acid consumption and heart rate variability in US adults." Circulation, 117:1130-1137 (2008).
Naba, H., et al., "Improving effect of ethyl eicosapentanoate on statin-induced rhabdomyolysis in Eisai hyperbilirubinemic rats." Biochemical and Biophysical Research Communications, 340:215-220 (2006).
Nagakawa et al., Effect of [EPA] on the Platelet Aggregation and Composition of Fatty Acid in Man: A Double Blind Study, Atherosclerosis 47(1):71-75 (1983).
Naik H, Wu JT, Palmer R, McLean L. The effects of febuxostat on the pharmacokinetic parameters of rosiglitazone, a CYP2C8 substrate. Br. J. Clin. Pharmacol. Jan. 13, 2012;74:327-335.
Nakamura et al., Remnant lipoproteniemia is a risk factor for endothelial vasomotor dysfuction and coronary artery disease in metabolic syndrome, Atherosclerosis, vol. 181(2), pp. 321-327 (2005).
Nakamura, et al., "Effects of Eicosapentaenoic Acids on Remnant-like Particles, Cholesterol Concentrations and Plasma Fatty Acid Composition in Patients with Diabetes Mellitus." in vivo 12: 311-314 (1998).
Nakamura, H., et al., "Evaluation of ethyl icosapentate in the treatment of hypercholesterolemia in kidney transplant recipients." Transplantation Proceedings, 30:3047-3048 (1998).
Nakamura, N. et al., "Joint effects of HMG-CoA reductase inhibitors and eicosapentaenoic acids on serum lipid profile and plasma fatty acid concentrations in patients with hyperlipidemia," International Journal of Clinical and Laboratory Research, Springer, Berlin, DE LNKD-DOI: 10.1007/S005990050057, vol. 29, No. 1, pp. 22-25 (1999).
Nambi, V., et al., "Combination therapy with statins and omega-3 fatty acids." Am J Cardiol 98:34i-38i (2006).
Nasa, et al., "Long-Term Supplementation With Eicosapentaenoic Acid Salvages Cardiomyocytes From Hypoxia/Reoxygenation-Induced Injury in Rats Fed With Fish-Oil-Deprived Diet," Jpn. J. Pharmacol. 77, 137-146 (1998).
Natsuno et al., "Clinical Effects of Eicosapentaenoic Acid on Type-2 Diabetes Effects on Serum Lipids, Pulse Wave Speed, and Ankle-Brachial Blood Pressure Index," Diagnosis and Treatment 93(12):133-137 (2005)(16 pages).
Nattel, S., et al., "Atrial remodeling and atrial fibrillation: Mechanisms and implications." Circ Arrhythmia Electrophysiol, 1:62-73 (2008).
Negre-Salvayre, A., et al., "Advanced lipid peroxidation end products in oxidative damage to proteins. Potential role in diseases and therapeutic prospects for the inhibitors." British Journal of Pharmacology 153:6-20 (2008).
Nelson, G.J., et al., "The Effect of Dietary Docosahexaenoic Acid on Plasma Lipoproteins and Tissue Fatty Acid Composition in Humans", Lipids, 32(11):1137-1146, (1997).

Nemets, Boris, M.D., "Addition of Omega-3 Fatty Acid to Maintenance Medication Treatment for Recurrent Unipolar Depressive Disorder", Am. J. Psychiatry, 159(3):477-479, (Mar. 2002).
Nemoto et al., "Ethyl-eicosapentaenoic Acid Reduces Liver Lipids and Lowers Plasma Levels of Lipids in Mice Fed a High-Fat Diet, in vivo," 23:685-690 2009).
Nenseter, MS et al., "Effect of dietary supplementation with n-3 polyunsaturated fatty acids on physical properties and metabolism of low density lipoprotein in humans," Arterioscler. Thromb. Vasc. Biol., 12;369-379 (1992).
Nestel, et al., "The n-3 fatty acids eicosapentaenoic acid and docosahexaenoic acid increase systemic arterial compliance in humans," Am J Clin Nutr., 76:326-30 (2002).
Nestel, P.J., "Effects of N-3 fatty acids on lipid metabolism." Ann Rev Nutr., 10:149-167 (1990).
Niemi M, Backman JT, Grantors M, Laitila J, Neuvonen M, Neuvonen PJ. Gemfibrozil considerably increases the plasma concentrations of rosiglitazone. Diabetologia. 2003;46: 1319-1323.
Niemi M, Backman JT, Neuvonen PJ. Effects of trimethoprim and rifampin on the pharmacokinetics of the cytochrome P450 2C8 substrate rosiglitazone. Clin. Pharmacol. Ther. 2004;76:239-249.
Nigon F, Lesnik P, Rouis M, Chapman MJ. Discrete subspecies of human low density lipoproteins are heterogeneous in their interaction with the cellular LDL receptor. J. Lipid Res. 1991;32(11):1741-1753.
Nishikawa M. et al., "Effects of Eicosapentaenoic acid (EPA) on prostacyclin production in diabetics. GC/MS analysis of PGI2 and PGI3 levels" Methods Find Exp Clin Pharmacol. 19(6):429-33 (1997).
Nobukata, H., et al., "Age-related changes in coagulation, fibrinolysis, and platelet aggregation in male WBN/Kob rats." Thrombosis Research 98: 507-516 (2000).
Nobukata, H., et al., "Long-term administration of highly purified eicosapentaenoic acid ethyl ester improves the dysfunction of vascular endothelial and smooth muscle cells in male WBN/Kob rats." Metabolism, 49(12): 1588-1591 (2000).
Noguchi et al., "Chemoprevention of DMBA-induced mammary carcinogenesis in rats by low-dose EPA and DHA." Br. J. Cancer 75(3): 348-353 (1997).
Nomura et al., "The effects of pitavastatin, eicosapentaenoic acid and combined therapy on platelet-derived microparticles and adiponectin in hyperlipidemic, diabetic patients." Platelets, 20(10:16-22 (2009).
Nourooz-Zadeh, J., et al., "Urinary 8-epi-PGF2α and its endogenous β-oxidation products (2,3-dinor and 2,3-dinor-5,6-dihydro) as biomarkers of total body oxidative stress." Biochemical and Biophysical Research Communications 330:731-736 (2005).
Nozaki S. et al., "Effects of purified Eicosapentaenoic acid ethyl ester on plasma lipoproteins in primary hypercholesterolemia" Int J Vitam Nutr Res. 62(3):256-260 (1992).
Obata, et al., "Eicosapentaenoic acid inhibits prostaglandin D2 generation by inhibiting cyclo-oxygenase in cultured human mast cells", Clin. & Experimental Allergy, 29:1129-1135, (1999).
O'Donnell, C.J., et al., "Leukocyte telomere length and carotid artery intimal medial thickness—the Framingham heart study." Arteriosclerosis, Thrombosis, and Vascular Biology.28:1165-1171 (2008).
Oemar BS, Tschudi MR, Godoy N, Brovkovich V, Malinski T, Luscher TF. Reduced endothelial nitric oxide synthase expression and production in human atherosclerosis. Circulation. 1998;97:2494-2498.
Oh, Robert C et al., Management of Hypertriglyceridemia, American Family Physician, LNKD-PUBMED: 17508532, vol. 75, No. 9, pp. 1365-1371 (2007).
Ohara Y, Peterson TE, Harrison DG. Hypercholesterolemia increases endothelial superoxide anion production. J. Clin. Invest. 1993;91:2546-2551.
Okuda, Y. et al., Eicosapentaenoic acid enhances nitric oxide production by cultured human endothelial cells. Biochem. Biophys. Res. Commun. 232: 487-491 (1997).
Okuda, Y., et al., "Long-term effects of eicosapentaenoic acid on diabetic peripheral neuropathy and serum lipids in patients with type II diabetes mellitus." Journal of Diabetes and Its Complications 10:280-287 (1996).

(56) References Cited

OTHER PUBLICATIONS

Okumura, T., et al., "Eicosapentaenoic acid improves endothelial function in hypertriglyceridemic subjects despite increased lipid oxidizability." Am J Med Sci 324(5):247-253 (2002).
Oliw, E.H., et al., "Biosynthesis of prostaglandins from 17(18)epoxy-eicosatetraenoic acid, a cytochrome P-450 metabolite of eicosapentaenoic acid." Biochimica el Biophysica Acta, 1126, 261-268 (1992).
Olofsson et al., "Apolipoprotein B: a clinically important apolipoprotein which assembles atherogenic lipoproteins and promotes the development of atherosclerosis" Journal of Internal Medicine, 258: 395-410 (2005).
OMACOR® Prescribing Information (Omega-3-acid ethyl esters, capsules) (2004). (9 pages).
Omacor®, Physicians' Desk Reference 2735 (60th ed. 2006)(3 pages).
Ona, V.O., et al., Nature, vol. 399, Inhibition of caspase-1 slows disease progression in a mouse model of Huntington's disease, pp. 263-267 (1999).
Ooi EM, "Apolipoprotein C-III: Understanding an emerging cardiovascular risk factor", Clin.Sci. (London), vol. 114, pp. 611-624 (2008).
Opalinska et al., "Increasing Level of Prostate-Specific Antigen and Prostate Cancer Risk Factors Among 193 Men Examined in Screening Procedure," Ann. Univ. Curie Sklowoska Med., 58(2):57-63 (Abstract Only)(2003)(2 pages).
O'Riordan, "DHA and EPA have differential effects on LDL-cholsterol," May 24, 2011 [online][Retrieved on Aug. 21, 2015] Retrieved from website: http://www.medscape.com/viewarticle/743305 (2 pages).
Osher et al., "Omega-3 Eicosapentaenoic Acid in Bipolar Depression: Report of a Small Open-Label Study," J. Clin. Psych. 66:726-729 (2005).
Ou Z, Ou J, Ackerman AW, Oldham KT, Pritchard KA, Jr. L-4f, an apolipoprotein a-1 mimetic, restores nitric oxide and superoxide anion balance in low-density lipoprotein-treated endothelial cells. Circulation. 2003;107:1520-1524.
Ozaki M, Kawashima S, Yamashita T, Hirase T, Namiki M, Inoue N, Hirata K, Yasui H, Sakurai H, Yoshida Y, Masada M, Yokoyama M. Overexpression of endothelial nitric oxide synthase accelerates atherosclerotic lesion formation in apoe-deficient mice. J. Clin. Invest. 2002; 110:331-340.
Ozawa, Akio, Nakamura E, Jinbo H. Fujita T, Hirai A, Terano T, Hamazaki T et al., "Determination of highger fatty acids in various lipid fractions of human plasma, platelets, and erythrocyte membrane using thin layer chromatography and gas chromatography," Bunseki Kagaku, 32:174-8 (1982) (with English abstract).
Park JH, Park DI, Kim HJ, et al. Metabolic syndrome is associated with erosive esophagitis. World J. Gastroenterol. Sep. 14, 2008 (35): 5442-7.
Park JY, Kim KA, Kang MH, Kim SL, Shin JG. Effect of rifampin on the pharmacokinetics of rosiglitazone in healthy subjects. Clin. Pharmacol. Ther. 2004;75:157-162.
Park, Y., et al., "Omega-3 fatty acid supplementation accelerates chylomicron triglyceride clearance." J. Lipid Res. 44:455-463 (2003).
Patel et al., "Rosiglitazone monotherapy improves glycaemic control in patients with type 2 diabetes: a twelve-week, randomized, placebo-controlled study," Diabetes, Obesity and Metabolism, vol. 1, pp. 165-172 (1999).
Paton, CM, Ntambi, JM., Biochemical and physiological function of stearoyl-CoA desaturase, Am. J. Physiol. Endocrinol. Metab. 2009;297:E28-E37.
PCT/GB00/00164 International Search Report dated Oct. 20, 2000 (8 pages).
PCT/US2011/062247 International Search Report and Written Opinion dated Jun. 14, 2012 (12 pages).
PCT/US2013/020526 International Search Report dated Mar. 29, 2013 (2 pages).
PCT/US2013/048241 International Search Report dated Dec. 13, 2013 (3 pages).

PCT/US2013/048516 International Search Report dated Dec. 20, 2013 (3 pages).
PCT/US2013/048559 International Search Report dated Dec. 13, 2013 (3 pages).
PCT/US2013/068647 International Search Report and Written Opinion dated May 13, 2014 (18 pages).
PCT/US2014/019454 International Search Report and Written Opinion dated Jun. 3, 2014 (12 pages).
Pedersen RS, Damkier P, Brosen K. The effects of human CYP2C8 genotype and fluvoxamine on the pharmacokinetics of rosiglitazone in healthy subjects. Br. J. Clin. Pharmacol. 2006;62:682-689.
Pedersen, T., et al., "Randomised trial of cholesterol lowering in 4444 patients with coronary heart disease: the Scandinavian Simvastation Survival Study (4S)", The Lancet, No. 19, vol. 344, 8934, p. 1383-1389 (1994).
Peet et al., "A Dose-Ranging Study of the Effects of Ethyl-Eicosapentaenoate in Patients with Ongoing Depression Despite Apparently Adequate Treatment with Standard Drugs", Arch. Gen. Psychiatry, 59:913-919 (2002).
Peet, M., et al., Phospholipid Spectrum Disorder in Psychiatry pp. 1-19, (1999).
Pejic et al., "Hypertriglyceridimia," Journ. Amer. Board Fam. Med., vol. 19(3):310-316 (2006).
Pennathur S, Heinecke JW. Mechanisms for oxidative stress in diabetic cardiovascular disease. Antioxid. Redox Signal. 2007;9(7):955-969.
Piccini, Monica, et al., Genomics, vol. 47, "FACL4, a new gene encoding long-chain acyl-CoA synthetase 4, is deleted in a family with Alport syndrome, elliptocytosis, and mental retardation," pp. 350-358 (1998).
Piche, "Tumor Necrosis Factor-Alpha, and Fibrinogen to Abdominal Adipose Tissue, Blood Pressure, and Cholesterol and Triglyceride Levels in Healthy Postmenopausal Women", American Journal of Cardiology, 2005, 96(1), 92-97.
Pike, NB, "Flushing out the role of GPR109A (HM74V) in the clinical efficacy of nicotinic acid", J. Clin. Invest., 115:3400-3403, (2005).
Plusepa® Product brochure "Super Critically Different from Other Omega-3 Fish Oil Supplements for Depression and ADHD," by Minami Nutrition (Apr. 2009, pp. 1-6).
Pownall, H.J., et al., "Correlation of serum triglyceride and its reduction by ω-3 fatty acids with lipid transfer activity and the neutral lipid compositions of high-density and low-density lipoproteins." Atherosclerosis 143:285-297 (1999).
Press Release: Amarin Corporation Says Huntington's Diease Drug Failed in Trials, http://www.fiercebiotech.com/node/6607/print (Apr. 24, 2007) (Printed on Aug. 22, 2008)(2 pages).
Pritchard KA, Ackerman AW, Ou J, Curtis M, Smalley DM, Fontana JT, Stemerman MB, Sessa WC. Native low-density lipoprotein induces endothelial nitric oxide synthase dysfunction: Role of heat shock protein 90 and caveolin-1. Free Radic. Biol. Med. 2002;33:52-62.
Pritchard KA, Jr., Groszek L, Smalley DM, Sessa WC, Wu M, Villalon P, Wolin MS, Stemerman MB. Native low-density lipoprotein increases endothelial cell nitric oxide synthase generation of superoxide anion. Circ. Res. 1995;77:510-518.
Puri, B., et al., "Eicosapentaenoic Acid in Treatment-Resistant Depression Associated with Symptom Remission, Structural Brain Changes and Reduced Neuronal Phospholipid Turnover," Int J Clinical Practice, 55:560-563 (2001).
Puri, B., et al., Archives of General Psychiatry, No. 55, "Sustained remission of positive and negative symptoms of schizophrenia following treatment with eicosapentaenoic acid," pp. 188-189, (1998).
Puri, B.K., et al., "Ethyl-EPA in Huntington Disease: A Double-Blind, Randomized, Placebo-Controlled Trial", Neurology, 65:286-292, (2005).
Qi, K., et al., "Omega-3 fatty acid containing diets decrease plasma triglyceride concentrations in mice by reducing endogenous triglyceride synthesis and enhancing the blood clearance of triglyceride-rich particles." Clinical Nutrition 27(8):424-430 (2008).
Rader, Lipid Disorders, in Eric J. Topol (ed.)Textbook of Cardiovascular Medicine pp. 55-75 (2007).

(56) References Cited

OTHER PUBLICATIONS

Rahimy M, Hallen B, Narang P. Effect of tolterodine on the anticoagulant actions and pharmacokinetics of single-dose warfarin in healthy volunteers. Arzneimittelforschung 2002 52 (12): 890-5.
Raitt, M.H., et al., "Fish oil supplementation and risk of ventricular tachycardia and ventricular fibrillation in patients with implantable defibrillators—a randomized controlled trial." JAMA. 293(23):2884-2891 (2005).
Rambjor, Gro S., et al., "Eicosapentaenoic Acid is Primarily Responsible for Hypotrigylceridemic Effect of Fish Oil in Humans", Fatty Acids and Lipids from Cell Biology to Human Disease: Proceedings of the 2nd international Congress of the ISSFAL (International Society for the Study of Fatty Acids and Lipids, AOCS Press, 31:S-45-S-49, (1996).
Randomised trial of cholesterol lowering in 4444 patients with coronary heart disease. The Scandinavian Simvastatin Survival Study, Lancet. 344: 1383-1389 (1994).
Rao MN, Mullangi R, Katneni K, et al. Lack of effect of sucralfate on the absorption and pharmacokinetics of rosiglitazone. J. Clin. Pharmacol. 2002;42:670-675.
Rees DD, Palmer RM, Moncada S. The role of endothelium-derived nitric oxide in the regulation of blood pressure. Proc. Natl. Acad. Sci. USA. 1989;86:3375-3378.
Reich, "Formulation and physical properties of soft capsules," Pharmaceutical capsules. (2004) Chapter 11:201-212.
Reiffel, J.A., et al., "Antiarrhythmic effects of omega-3 fatty acids." Am J Cardiol 98:50i-60i (2006).
Reiner Z, Catapano AL, De BG, et al. ESC/EAS Guidelines for the management of dyslipidaemias: the Task Force for the management of dyslipidaemias of the European Society of Cardiology (ESC) and the European Atherosclerosis Society (EAS). Eur. Heart J. 2011;32:1769-1818.
Ridker, "C-Reactive Protein : A Simple Test to Help Predict Risk of Heart Attack and Stroke", Circulation: Journal of the American Heart Association, 2003, 108, e81-e85.
Riediger, N.D., et al., "A systemic review of the roles of n-3 fatty acids in health and disease." J Am Diet Assoc. 109:668-679. (2009).
Rifai, "High-Sensitivity C-Reactive Protein: A Novel and Promising Marker of Coronary Heart Disease", Clinical Chemistry, 2001, 47(3), 403-411.
Risé, P., et al., "Effects of simvastatin on the metabolism of polyunsaturated fatty acids and on glycerolipid, cholesterol, and de novo lipid synthesis in THP-1 cells." J. Lipid Res. 38:1299-1307 (1997).
Rissanen et al., "Fish Oil-Derived Fatty Acids, Docosahexaenoic Acid and Docosapentaenoic Acid, and the Risk of Acute Coronary Events The Kuopio Ischaemic Heart Disease Risk Factor Study," Circulation. (Nov. 28, 2000)(102):2677-2679 doi:10.1161/01.CIR. 102.22.2677.
Rizzo M, Bemeis K. Low-density lipoprotein size and cardiovascular risk assessment. Q. J. Med. 2006;99(1): 1-14.
Roach, P.D., et al., "The effects of dietary fish oil on hepatic high density and low density lipoprotein receptor activities in the rat." FEBS Lett., 222: 159-162 (1987).
Robinson, J.G., et al., "Meta-analysis of the relationship between non-high-density lipoprotein cholesterol reduction and coronary heart risk." J Am Coll Cardiol., 53: 316-322 (2009).
Roche, H.M., et al., "Effect of long-chain n-3 polyunsaturated fatty acids on fasting and postprandial triacylglycerol metabolism." Am J Clin Nutr 71:232S-7S (2000).
Roche, H.M., et al., "Long-chain n-3 polyunsaturated fatty acids and triacylglycerol metabolism in the postprandial state." Lipids 34: S259-S265 (1999).
Rodriguez, Y., et al., "Long-chain ω6 polyunsaturated fatty acids in erythrocyte phospholipids are associated with insulin resistance in non-obese type 2 diabetics." Clinica Chimica Acta 354:195-199 (2005).
Rogers, P. J., "No effect of n-3 long-chain polyunsaturated fatty acid (EPA and DHA) supplementation on depressed mood and cognitive function: a randomised controlled trial" British Journal of Nutrition, 99:421-431, (2008).
Rost KL, Roots I. Nonlinear kinetics after high-dose omeprazole caused by saturation of genetically variable CYP2C19. Hepatology Jun. 23, 1996 (6): 1491-7.
Rubins, HB, et al., "Distribution of lipids in 8,500 men with coronary artery disease: Department of Veterans Affairs HDL Intervention Trial Study Group," Am. J. Cardiol, 75:1196-1201, (1995).
Rubins, HB, et al., "Gemfibrozil for the prevention of coronary heart disease in men with low levels of high-density lipoprotein cholesterol: Veterans Affairs HDL-C Intervention Trial Study Group", N. Eng. J. Med., 341:410-418, (1999).
Ruiz-Narváez, E.A., et al., "Abdominal obesity and hyperglycemia mask the effect of a common APOC3 haplotype on the risk of myocardial infarction." Am J Clin Nutr 87:1932-8 (2008).
Ruocco MJ, Shipley GG. Interaction of cholesterol with galactocerebroside and galactocerebroside phosphatidylcholine bilayer membranes. Biophys. J. 1984;46:695-707.
Rustan, A.C., et al., "Eicosapentaenoic acid inhibits cholesterol esterification in cultured parenchymal cells and isolated microsomes from rat liver." J. Bio. Chem. 263(17):8126-32 (1988).
Rustan, A.C., et al., "Eicosapentaenoic acid reduces hepatic synthesis and secretion of triacylglycerol by decreasing the activity of acyl-coenzyme A:1,2-diacylglycerol acyltransferase." J. Lipid Res. 29:1417-1426 (1988).
Rustan, A.C., et al., "Postprandial decrease in plasma unesterified fatty acids during n-3 fatty acid feeding is not caused by accumulation of fatty acids in adipose tissue." Biochimica et Biophysica Acta 1390.245-25 (1998).
Ryan, A.M., et al., "Enteral nutrition enriched with eicosapentaenoic acid (EPA) preserves lean body mass following esophageal cancer surgery: results of a double-blinded randomized controlled trial." Ann Surg 249:355-363 (2009).
Ryan, A.S., et al., "Clinical overview of algal-docosahexaenoic acid: effects on triglyceride levels and other cardiovascular risk factors." Am J Ther., 16:183-192 (2009).
Sacks, Frank M., "The apolipoprotein story," Atherosclerosis Supplements, 23-27 (2006).
Saito et al., "Effects of EPA on coronary artery disease in hypercholesterolemic patients with multiple risk factors: Sub-analysis of primary prevention cases from the Japan EPA Lipid Intervention Study (JELIS)," Atherosclerosis, 200:135-140 (2008).
Saito et al., "Results of Clinical Usage of Improved Formulation (MND-21S) Epadel Capsule 300 with Respect to Hyperlipidemia," 26(12) Jpn. Pharmacol. Ther. 2047-62 (1998) (with English abstract).
Saito, J., et al., "Mechanisms of enhanced production of PGI2 in cultured rat vascular smooth muscle cells enriched with eicosapentaenoic acid." Atherosclerosis 131: 219-228 (1997).
Sampath H, Ntambi JM., Role of stearoyl-CoA desaturase in human metabolic disease, Future Lipidol. 2008;3.163-73.
Sampath H, Ntambi JM., The Role of stearoyl-CoA desaturase in obesity, insulin resistance, and inflammation, Ann. NY. Acad. Sci. 2011; 1243:4 7-53.
Samuels, Martin A., M. D., et al., "Huntington's Disease", Office Practice of Neurology, (122):654-655, (1996).
Sanders, A. Hinds and C.C. Pereira, "Influence of n-3 fatty acids on blood lipids in normal subjects" Journal of Internal Medicine. 225:99-104,(1989).
Sanders, et al., "Influence of an algal triacylglycerol containing docosahexaenoic acid (22:6n-3) and docosapentaenoic acid (22:5n-6) on cardiovascular risk factors in healthy men and women," British Journal of Nutrition, 95, 525-531 (2006).
Sanders, T.A., et al., "Effect of varying the ratio of n-6 to n-3 fatty acids by increasing the dietary intake of α-linolenic acid, eicosapentaenoic and docosahexaenoic acid, or both on fibrinogen and clotting factors VII and XII in persons aged 45-70 y: the OPTILIP Study." Am J Clin Nutr 84:513-22 (2006).
Sanders, T.A., et al., "Triglyceride-lowering effect of marine polyunsaturates in patients with hypertriglyceridemia." Arterioscler. Thromb. Vasc. Biol. 5:459-465 (1985).

(56) References Cited

OTHER PUBLICATIONS

Sasaki J, Miwa T, Odawara M. Administration of highly purified eicosapentaenoic acid to statintreated diabetic patients further improves vascular function. Endocr. J. 2012;59:297-304.

Sasaki J, Yokoyama M, Matsuzaki M, et al. Relationship between coronary artery disease and non-HDL-C, and effect of highly purified EPA on the risk of coronary artery disease in hypercholesterolemic patients treated with statins: sub-analysis of the Japan EPA Lipid Intervention Study (JELIS). J. Atheroscler. Thromb. 2012;19:194-204.

Sasaki, Y.F., et al., "Bio-anticlastogenic effects of unsaturated fatty acids included in fish oil—docosahexaenoic acid, docosapentaenoic acid, and eicosapentaenoic acid—in cultured Chinese hamster cells." Mutation Research, 320: 9-22 (1994).

Sato et al., "General Pharmacological Studies on 5 8 11 14 17 Eicosapentaenoic Acid Ethyl Ester EPA-E", Folia Pharmacol JPN, 94 (1), 35-47. (1989) (with English abstract).

Sato, "Effects of Highly Purified Ethyl All-cis-5,8,11,14,17-icosapentaenoate (EPA-E) on Rabbit Platelets," Biol. Pharm. Bull., 16(4)362-367 (1993).

Satoh et al., "Highly purified eicosapentaenoic acid reduces cardio-ankle vascular index in association with decreased serum amyloid A-LDL in metabolic syndrome," Hypertension Research (2009) (32):1004-1008.

Satoh, N., et al., "Purified eicosapentaenoic acid reduces small dense LDL, remnant lipoprotein particles, and C-reactive protein in metabolic syndrome." Diabetes Care, 30(1): 144-146 (2007).

Satoh-Asahara N, Shimatsu A, Sasaki Y, Nakaoka H, Himeno A, Tochiya M, Kono S, Takaya T, Ono K, Wada H, Suganami T, Hasegawa K, Ogawa Y., "Highly purified eicosapentaenoic acid increases interleukia-10 levels of peripheral blood monocytes in obese patients with dyslipidemia." Diabetes Care. 2012;35(12):2631-2639.

Schectman, G., et al., "Dietary fish oil decreases low-density-lipoprotein clearance in nonhuman primates." Am J Clin Nutr., 64:215-221 (1996).

Schmitz PG, McCloud LK, Reikes ST, et al. Prophylaxis of hemodialysis graft thrombosis with fish oil: double-blind, randomized, prospective trial. J. Am. Soc. Nephrol. Jan. 13, 2002 (1): 184-90.

Schmitz, G., et al., "The opposing effects of n-3 and n-6 fatty acids." Progress in Lipid Research, 47:147-155 (2008).

Schreiner et al., "Lipoprotein[a] as a Risk Factor for Preclinical Atherosclerosis, 13 Atherosclerosis, Thrombosis & Vascular Biology 826, 826 (1993).

Schuirmann, D.J. A comparison of the two one-sided tests procedure and the power approach for assessing the equivalence of average bioavailability. J. Pharmacokinet. Biopharm. 15, 657-680 (1987).

Schwellenbach et al., "The Triglyceride-Lowering Effects of a Modest Dose of Docosahexaenoic Acid Alone Versus in Combination with Low Dose Eicosapentaenoic Acid in Patients with Coronary Artery Disease and Elevated Triglycerides." J. Am. Coll. Nutr. 25(6):480-485 (2006).

Segrest et al., Structure of Apolipoprotein B-100 in Low Density Lipoproteins, J. Lipid Res. 42(9):1346-1367 (2001).

Self-Medlin Y, Byun J, Jacob RF, Mizuno Y, Mason RP. Glucose promotes membrane cholesterol crystalline domain formation by lipid peroxidation. Biochim. Biophys. Acta. 2009; 1788(6): 1398-1403.

Serhan, C.N., et al., "Resolvins: A family of bioactive products of omega-3 fatty acid transformation circuits initiated by aspirin treatment that counter proinflammation signals." J. Exp. Med. 196:1025-1037 (2002).

Sevanian A, Ursini F. Lipid peroxidation in membranes and low-density lipoproteins: similarities and differences. Free Radic. Biol. Med. 2000;29(3-4):306-311.

Shimizu et al., "Effects of Highly Purified Eicosapentaenoic Acid on Erythrocyte Fatty Acid Composition and Leukocyte and Colonic Mucosa Leukotriene B4 Production in Children with Ulcerative Colitis," J. Pediatr. Gastroenterol. Nutr., vol. 37, No. 5, pp. 581-585 (2003).

Shimizu, H., et al., "Long-term effect of eicosapentaenoic acid ethyl (EPA-E) on albuminuria of non-insulin dependent diabetic patients." Diabetes Research and Clinical Practice 28: 35-40 (1995).

Shimokawa H, Flavahan NA, Vanhoutte PM. Loss of endothelial pertussis toxin-sensitive g protein function in atherosclerotic porcine coronary arteries. Circulation. 1991;83:652-660.

Shinozaki K. et al., "The long-term effect of Eicosapentaenoic acid on serum levels of lipoprotein (a) and lipids in patients with vasciular disease" J Atheroscler Thromb. 2(2):207-9 (1996).

Shishehbor MH, Brenna ML, Aviles RJ, Fu X, Penn MS, Sprecher DL, Hazen SL. Statins promote potent systemic antioxidant effects through specific inflammatory pathways. Circulation. 2003;108(4):426-431.

Sicherer et al., "Prevalence of seafood allergy in the United States determined by a random telephone survey," J. Allergy Clin. Immunol., 114(1):159-165 (Jul. 2004).

Silvers, Karen M., et al., "Randomised double-blind placebo-controlled trial of fish oil in the treatment of depression", Prostagandins, Leukotrienes and Essential Fatty Acids, 72:211-218, (2005).

Simoens, C.M., et al., "Inclusion of 10% fish oil in mixed medium-chain triacylglycerol-long chain triacylglycerol emulsions increases plasma triacylglycerol clearance and induces rapid eicosapentaenoic acid (20:5n-3) incorporation into blood cell phospholipids." Am J Clin Nutr 88: 282-8 (2008).

Simopoulos, "Omega-3 fatty acids in health and disease and in growth and development," Am. J. Clin. Nutr. 54:438-63 (1991).

Singer, Peter, "Fluvastatin plus fish oil are more effective on cardiovascular risk factors than fluvastatin alone," Letter to the Editor, Prostaglandinis, Leukotrienes and Essential Fatty Acids, vol. 72, pp. 379-380 (2005).

Slides for the Oct. 16, 2013 Meeting of the Endocrinologic and Metabolic Drugs Advisory Committee, (158 pages).

Sniderman A, Kwiterovich PO. Update on the detection and treatment of atherogenic low-density lipoproteins. Curr. Opin. Endocrinol. Diabetes Obes. Apr. 20, 2013;20:140-147.

Stampfer MJ, Krauss RM, Ma J, et al. A prospective study of triglyceride level, lowdensity lipoprotein particle diameter, and risk of myocardial infarction. JAMA. 1996;276:882-888.

Steinberg D, Witztum JL. Is the oxidative modification hypothesis relevant to human atherosclerosis? Do the antioxidant trials conducted to date refute the hypothesis? Circulation. 2002;105:2107-2111.

Steinberg D. Lewis A. Conner Memorial Lecture: Oxidative modification of LDL and atherogenesis. Circulation. 1997;95(4):1062-1071.

Stepp DW, Ou J, Ackerman AW, Welak S, Klick D, Pritchard KA, Jr. Native ldl and minimally oxidized ldl differentially regulate superoxide anion in vascular endothelium in situ. Am. J. Physiol. 2002;283:H750-H759.

Sternbach "The Glasgow Coma Scale." The Journal of Emergency Medicine, 19(1):67-71 (Feb. 8, 2000).

Stiles, FDA approves EPA-only omega-3 PUFA capsule for high TG, http://www.medscape.com/viewarticle/791268, accessed Dec. 17, 2014 (1 page).

Stojancevic et al., "The impact of farnesoid X receptor activation on intestinal permeability in inflammatory bowel disease," Can. J Gastroenterol. 26(9):631-637 (2012).

Sugiyama et al., "A Comparison of the Hypotensive Effects of Eicosapentaenoic Acid Ethyl (EPA) on Three Diseases (Occluded Arteriosclerosis, Hyperlipidemia, and These Two Diseases Combined) P2-504 Abstract," Annual Meeting of the Japanese Society of Pharmaceutical Health Care and Sciences 20:473 (Nov. 2010) (with English translation)(3 pages).

Takaki A, Umemoto S, Ono K, Seki K, Ryoke T, Fujii A, Itagaki T, Harada M, Tanaka M, Yonezawa T, Ogawa H, Matsuzaki M. Add-on therapy of epa reduces oxidative stress and inhibits the progression of aortic stiffness in patients with coronary artery disease and statin therapy: A randomized controlled study. J. Atheroscler. Thromb. 2011;18:857-866.

Takaku et al., Study on the Efficacy and Safety of Ethyl Icosapentate (MND-21) in Treatment of Hyperlipidemia Based on a Long-Term Administration Test, 7 J. Clin. Ther. Med. 191 (1991) (with English Translation)(27 pages).

(56) References Cited

OTHER PUBLICATIONS

Talayero BG, Sacks FM. The role of triglycerides in atherosclerosis. Curr. Cardiol. Rep. 2011;13:544-552.

Tanaka et al., "Genome-Wide Association Study of Plasma Polyunsaturated Fatty Acids in the InCHIANTI Study." PLoS Genetics 5(1):1-8 (Jan. 2009).

Tanaka et al., "Suppression of prostaglandin synthesis by arachidonic acid or eicosapentaenoic acid in a macrophage-like cell line, RAW 264.7, treated with LPS," Biol. Pharm. Bull., 22(10):1057-7 (1999).

Takana et al., "Administration of high dose eicosapentaenoic acid enhances anti-inflammatory properties of high-density lipoprotein in Japanese patients with dyslipidemia," Atherosclerosis, 237(2):577-83 (Dec. 2014).

Tanaka et al., "Eicosapentaenoic Acid-Enriched High-Density Lipoproteins Exhibit Anti-Atherogenic Properties," Circ. J., doi: 10.1253/circj.CJ-17-0294. [Epub ahead of print] (Jun. 23, 2017)(6 pages).

Tanaka, K.T., et al., "Reduction in the recurrence of stroke by eicosapentaenoic acid for hypercholesterolemic patients—Subanalysis of the JELIS trial." Stroke, 39(7):2052-8 (2008).

Taylor et al., "Fish allergy: fish and products thereof," Journal Food Science (2004) 69.8 R175-R180.

Theobald et al., "LDL Cholesterol-Raising Effect of Low-Dose Docosahexaenoic in Middle-Aged Men and Women," Am. J. Clin. Nutr. 79:558-63 (2004).

Third Report of the NCEP Expert Panel on Detection, Evaluation, and Treatment of High Blood Cholesterol in Adults (Adult Treatment Panel III) Final Report, NIH Publication No. 02-5215 Sep. 2002 (220 pages in three parts).

Thorwest M, Balling E, Kristensen SD, et al. Dietary fish oil reduces microvascular thrombosis in a porcine experimental model. Thromb. Res. Jul. 2000 99 (2): 203-8.

Tilg H, Moschen AR. Inflammatory Mechanisms in the Regulation of Insulin Resistance. Mol. Med. 2008;14(3-4):222-231.

Transcript from Oct. 16, 2013 Meeting of the Endocrinologic and Metabolic Drugs Advisory Committee, 76 pages.

Tribble DL, Holl LG, Wood PD, Krauss RM. Variations in oxidative susceptibility among six low density lipoprotein subfractions of differing density and particle size. Atherosclerosis. 1992;93(3):189-199.

Tribble DL, Rizzo M, Chait A, Lewis DM, Blanche PJ, Krauss RM. Enhanced oxidative susceptibility and reduced antioxidant content of metabolic precursors of small, dense low-density lipoproteins. Am. J. Med. 2001;110(2):103-110.

Trilipix Package Insert (Sep. 2010)(10 pages).

Tsimikas S, Witztum JL, Miller ER, Sasiela WJ, Szarek M, Olsson AG, Schwartz GG. High-dose atorvastatin reduces total plasma levels of oxidized phospholipids and immune complexes present on apolipoprotein B-1 00 in patients with acute coronary syndromes in the MIRACL trial. Circulation. 2004;110(11):1406-1412.

Tulenko TN, Chen M, Mason PE, Mason RP. Physical effects of cholesterol on arterial smooth muscle membranes: Evidence of immiscible cholesterol domains and alterations in bilayer width C during atherogenesis. J. Lipid Res. 1998;39:947-956.

Turini et al., "Short-term fish oil supplementation improved innate immunity, but increased ex vivo oxidation of LDL in man—a pilot study." Eur. J. Nutr. 40:56-65 (2001).

U.S. Appl. No. 14/245,499, filed Apr. 4, 2014 (now abandoned)(43 pages).

Urquhart et al., "Profile of eicosanoids produced by human saphenous vein endothelial cells and the effect of dietary fatty acids," Prostaglandins Leukot. Essent. Fatty Acid, 65(1):15-22 (2001).

Vaagenes et al., "The Hypolipidaemic Effect of EPA is Potentiated by 2- and 3-Methylation." In P. Quant & S. Eaton (eds.) Current Views of Fatty Acid Oxidation and Ketogenesis from Organelles to Point Mutations; Advances in Experimental Medicine and Biology, vol. 466, pp. 221-226 (1999).

Vaddadi, K.S., et al., "A Randomised, Placebo-Controlled, Double-Blind Study of Treatment of Huntington's Disease with Unsaturated Fatty Acids", Clinical Neuroscience and Neuropathology, 13(1):29-33, (Jan. 2002).

Van der Steeg, W.A., et al., "High-density lipoprotein cholesterol, high-density lipoprotein particle size, and apolipoprotein A-I: Significance for cardiovascular risk—the IDEAL and EPIC-Norfolk studies." J. Am. Coll. Cardiol. 51;634-642 (2008).

Van Do et al., "Allergy to fish parvalbumins: Studies on the cross-reactivity of allergens from 9 commonly consumed fish," Journ. Allergy & Clin. Immunol., 16(6):1314-1320 (Dec. 1, 2005).

Van Wijk et al. Rosiglitazone improves postprandial triglyceride and free fatty acid metabolism in type 2 diabetes. Diabetes Care, vol. 28, No. 4, (2005) pp. 844-849.

Varbo et al., Remnant Cholesterol as a Causal Risk Factor for Ischemic Heart Disease, J. Am. Coll. Cardiol., vol. 61(4), pp. 427-436 (2013).

Varbo et al., Remnant cholesterol as a cause of ischemic heart disease: Evidence, definition, measurement, atherogenicity, high risk patients, and present and future treatment, Pharmacol. Ther., vol. 141(3), pp. 358-367 (2014).

Vascepa [package insert], Bedminster, NJ: Amarin Pharma Inc.; Jul. 2012. (12 pages).

Vascepa [package insert]. Bedminster, NJ: Amarin Pharma Inc.; Nov. 2013. (11 pages).

Vasudevan et al., "Effective Use of Combination of Lipid Therapy", Curr. Atheroscl. Rep., vol. 8, pp. 76-84 (2006).

Vedin, I., et al., "Effects of docosahexaenoic acid-rich n-3 fatty acid supplementation on cytokine release from blood mononuclear leukocytes: the OmegAD study." Am J Clin Nutr 87:1616-22 (2008).

Velliquette et al., "Regulation of human stearoyl-CoA desaturase by omega-3 and omega-6 fatty acids: Implications for the dietary management of elevated serum triglycerides," Journal of Clinical Lipdology. (2009) 3:281-288.

Vergnani L, Hatrik S, Ricci F, Passaro A, Manzoli N, Zuliani G, Brovkovych V, Fellin R, Malinski T. Effect of native and oxidized low-density lipoprotein on endothelial nitric oxide and superoxide production : Key role of 1-arginine availability. Circulation. 2000;101:1261-1266.

Vidal F, Colome C, Martinez-Gonzalez J, Badimon L. Atherogenic concentrations of native low density lipoproteins down-regulate nitric-oxide-synthase mma and protein levels in endothelial cells. Eur. J. Biochem. 1998;252:378-384.

Vidgren, H.M., et al., "Incorporation of n-3 fatty acids into plasma lipid fractions, and erythrocyte membranes and platelets during dietary supplementation with fish, fish oil, and docosahexaenoic acid-rich oil among healthy young men." Lipids 32: 697-705 (1997).

Virani et al., "The Role of Lipoprotein-associated Phospholipase A2 as a marker for atherosclerosis" Curr. Atheroscler. Rep. 9[2]: 97-103 (2007).

Volcik, K.A., et al., "Peroxisome proliferator—activated receptor agenetic variation interacts with n-6 and long-chain n-3 fatty acid intake to affect total cholesterol and LDL-cholesterol concentrations in the Atherosclerosis Risk in Communities Study." Am J Clin Nutr 87:1926-31 (2008).

Von Schacky C, Baumann K, Angerer P. The effect of n-3 fatty acids on coronary atherosclerosis: results from SCIMO, an angiographic study, background and implications. Lipids 2001 36 Suppl: S99-102.

Von Schacky, C., "A review of omega-3 ethyl esters for cardiovascular prevention and treatment of increased blood triglyceride levels." Vascular Health and Risk Management 2(3): 251-262 (2006).

Von Schacky, C., et al., "The Effect of Dietary ω-3 Fatty Acids on Cornoray Atherosclerosis: A Randomized, Double-Blind, Placebo-Controlled Trial", American College of Physicians-American Society of Internal Medicine, 130(7):554-562, (1999).

Wada, M., et al., "Enzymes and receptors of prostaglandin pathways with arachidonic acid-derived versus eicosapentaenoic acid-derived substrates and products." J. Biol. Chem. 282(31): 22254-22266 (2007).

Wagner AH, Kohler T, Ruckschloss U, Just I, Hecker M. Improvement of nitric oxide-dependent vasodilation by hmg-coa reductase inhibitors through attenuation of endothelial superoxide anion formation. Arterioscler. Thromb. Vasc. Biol. 2000;20:61-69.

(56) References Cited

OTHER PUBLICATIONS

Walker G, Mandagere A, Dufton C, et al. The pharmacokinetics and pharmacodynamics of warfarin in combination with ambrisentan in healthy volunteers. Br. J. Clin. Pharmacol. May 2009 67 (5): 527-34.
Walldius, G., et al., "Editorial: Rationale for using apolipoprotein B and apolipoprotein A-I as indicators of cardiac risk and as targets for lipid-lowering therapy." European Heart Journal 26, 210-212 (2005).
Walter MF, Jacob RF, Bjork RE, Jeffers B, Buch J, Mizuno Y, Mason RP. Circulating lipid hydroperoxides predict cardiovascular events in patients with stable coronary artery disease: the PREVENT study. J. Am. Coll. Cardiol. 2008;51(12):1196-1202.
Walter MF, Jacob RF, Jeffers B, Ghadanfar MM, Preston GM, Buch J, Mason RP. Serum levels of TBARS predict cardiovascular events in patients with stable coronary artery disease: A longitudinal analysis of the PREVENT study. J. Am. Coll. Cardiol. 2004;44(10):1996-2002.
Wander, R.C., et al., "Influence of long.chain polyunsaturated fatty acids on oxidation of low density lipoprotein." Prostaglandins, Leukotrienes and Essential Fatty Acids 59(2):143-151 (1998).
Wang, C., et al., "n-3 Fatty acids from fish or fish-oil supplements, but not α-linolenic acid, benefit cardiovascular disease outcomes in primary- and secondary-prevention studies: a systematic review." Am J Clin Nutr 84:5-17 (2006).
Wang, L., et al., "Triglyceride-rich lipoprotein lipolysis releases neutral and oxidized FFAs that induce endothelial cell inflammation." J. Lipid Res. 50:204-213 (2009).
Warren, Stephen T., "The Expanding World of Trinucleotide Repeats", Science, 271:1374-1375, (1996).
Wassmann S, Laufs U, Muller K, Konkol C, Ahlbory K, Baumer AT, Linz W, Bohm M, Nickenig G. Cellular antioxidant effects of atorvastatin in vitro and in vivo. Arterioscler. Thromb. Vasc. Biol. 2002;22:300-305.
Watanabe et al., "Bile acids lower triglyceride levels via a pathway involving FXR, SHP, and SREBP-1c," J Clin Invest. 113(10): 1408-1418 (May 2004).
Amarin Corporation, Annual Report, Jun. 24, 2010 (245 pages total)(submitted in three parts; Part I: Cover and pp. 1-39 (81 pages); Part II: pp. 40 through F-10 (81 pages); Part III: pp. F11-F51 (83 pages)).
Amarin Corporation, Executive Informational Overview, "Neurological Disease-Focused Biopharmaceutical Opportunity," SEC filing dated Oct. 11, 2005 (99 pages).
ASCEND Study Collaborative Group. Effects of n-3 fatty acid supplements in diabetes mellitus. N Engl J Med, 379(16):1540-1550 (publication date Oct. 18, 2018; epublication date Aug. 26, 2018).
Aung T, Halsey J, Kromhout D, et al. Associations of omega-3 fatty acid supplement use with cardiovascular disease risks: Meta-analysis of 10 trials involving 77917 individuals. JAMA Cardiol 3:225-34 (publication date Mar. 1, 2018; epublication date Jan. 31, 2018).
Balfour et al., "Rosiglitazone," Drugs, 57(6):921-930 (Jun. 1999).
Bhatt DL, Eagle KA, Ohman EM, et al. Comparative determinants of 4-year cardiovascular event rates in stable outpatients at risk of or with atherothrombosis. JAMA 304(12):1350-7 (publication date Sep. 22, 2010; epublication date Aug. 30, 2010).
Bhatt DL, Fox KAA, Hacke W, et al; CHARISMA Investigators. Clopidogrel and aspirin versus aspirin alone for the prevention of atherothrombotic events. N Engl J Med. 354(16):1706-1717 (publication date Apr. 20, 2006; epublication date Mar. 12, 2006).
Bhatt DL, Hulot JS, Moliterno DJ, Harrington RA. Antiplatelet and anticoagulation therapy for acute coronary syndromes. Circ Res 114(12):1929-43 (publication date Jun. 6, 2014).
Bhatt DL, Steg PG, Brinton EA, et al. Rationale and design of REDUCE-IT: Reduction of Cardiovascular Events with Icosapent Ethyl-Intervention Trial. Clin Cardiol 40:138-48 (publication date Mar. 2017; epublication date Mar. 15, 2017).
Bhatt DL, Steg PG, Ohman EM, et al; REACH Registry Investigators. International prevalence, recognition and treatment of cardiovascular risk factors in outpatients with atherothrombosis. JAMA. 295(2):180-189 (publication date Jan. 11, 2006).
Brinton et al., "Effects of icosapent ethyl on lipid and inflammatory parameters in patients with diabetes mellitus-2, residual elevated triglycerides (200-500 mg/dL), and on statin therapy at LDL-C goal: the ANCHOR study," Cardiovasc. Diabetol. Jul. 9, 2013;12:100. doi: 10.1186/1475-2840-12-100.
Cannon CP, Blazing MA, Giugliano RP, et al; IMPROVE-IT Investigators. "Ezetimibe added to statin therapy after acute coronary syndromes." N Engl J Med. 372:2387-2397. (Jun. 18, 2015/ epub Jun. 3, 2015).
Cannon CP, Braunwald E, McCabe CH, et al. Intensive versus moderate lipid lowering with statins after acute coronary syndromes. N Engl J Med 350(15):1495-1504 (publication date Apr. 8, 2004; epublication date Mar. 8, 2004).
Cavender MA, Steg PG, Smith SC, et al; REACH Registry Investigators. Impact of diabetes mellitus on hospitalization for heart failure, cardiovascular events, and death: outcomes at 4 years from the reduction of atherothrombosis for continued health (REACH) registry. Circulation. 132(10):923-931 (publication date Sep. 8, 2015; epublication date Jul. 7, 2015).
Daniel et al., "The Effect of Elevated Triglycerices on the Onset and Progression of Coronary Artery Disease: A Retrospective Chart Review," Cholesterol, vol. 2015 (epub Nov. 4, 2015), Article ID 292935, 5 pages.
De Morais et al., "Evaluation of lipid extraction and fatty acid composition of human plasma," Rev. Bras. Hematol. Hemoter. 32(6):439-443 (2010).
Doi M, Nosaka K, Miyoshi T, et al. Early eicosapentaenoic acid treatment after percutaneous coronary intervention reduced acute inflammatory responses and ventricular arrhythmias in patients with acute myocardial infarction: A randomized controlled study. Int J Cardiol., 176(3):577-82 (publication date Oct. 20, 2014; epublication date Aug. 19, 2014).
Ganda OP, Bhatt DL, Mason RP, Miller M, Boden WE. Unmet need for adjunctive dyslipidemia therapy in hypertriglyceridemia management. J Am Coll Cardiol 72(3):330-43 (publication date Jul. 17, 2018).
Hamazaki et al., "Effects of fish oil rich in eicosapentaenoic acid on serum lipid in hyperlipidemic hemodialysis patients," Kidney Int'l., 26:81-84 (Jul. 1984).
Hong KN, Fuster V, Rosenson RS, Rosendorff C, Bhatt DL. How low to go with glucose, cholesterol, and blood pressure in primary prevention of CVD. J Am Coll Cardiol 70(17):2171-85 (publication date Oct. 24, 2017; epublication date Oct. 16, 2017).
Katayama et al., Effect of long-term administration of ethyl eicosapentate (EPA-E) on local cerebral blood flow and glucose utilization in stroke-prone spontaneously hypertensive rats (SHRSP), Brain Research, vol. 761, pp. 300-305 (Dec. 31, 1997).
Klempfner R, Erez A, Sag it BZ, et al. Elevated triglyceride level is independently associated with increased all-cause mortality in patients with established coronary heart disease: Twenty-two-year follow-up of the Bezafibrate Infarction Prevention Study and Registry. Circ Cardiovasc Qual Outcomes 9(2):100-8 (publication date Mar. 8, 2016).
Laird et al., "Relationship of early hyperglcemia to mortality in trauma patients," J. Trauma, 56(5):1058-1062 (May 2004).
Law TK, Yan AT, Gupta A, et al. Primary prevention of cardiovascular disease: global cardiovascular risk assessment and management in clinical practice. Eur Heart J Qual Care Clin Outcomes. 1(1):31-36 (publication date Jul. 2, 2015; epublication date Jul. 1, 2015).
Libby P. Triglycerides on the rise: should we swap seats on the seesaw? Eur Heart J. 36(13):774-776 (publication date Apr. 1, 2015; epublication date Dec. 29, 2014).
Lovaza TM (omega-3-acid ethyl esters) Capsules, Aug. 2007 (Aug. 1, 2007)m oaget 1-2, XP055589332.
Mayo Clinic, Diabetes Diagnosis and Treatment, 1998, http://www.mayoclinic.org/diseases-conditions/diabetes/diagnosis-treatment/drc-20371451 (1998-2018).
Meyer et al., "Comparison of Seal Oil to Tuna Oil on Plasma Lipid Levels and Blood Pressure in Hypertiglyceridaemic Subjects," Lipids, 44:827-835 (Sep. 2009).

(56) References Cited

OTHER PUBLICATIONS

Murck et al., "Ethyl-EPA in Huntington disease—Potentially relevant mechanism of action," Brain Research Bulletin, 72:159-164 (2007) (available online Nov. 15, 2006).

Murphy SA, Cannon CP, Blazing MA, et al. Reduction in total cardiovascular events with ezetimibe/simvastatin post-acute coronary syndrome. *J Am Coll Cardiol.* 67(4):353-361 (publication date Feb. 2, 2016; epublication date Jan. 25, 2016).

Nambi V, Bhatt DL. Primary prevention of atherosclerosis: Time to take a selfie? J Am Coll Cardiol 2017;70(24):2992-4 (publication date Dec. 19, 2017; epublication date Dec. 11, 2017).

Nelson et al. "Icosapent Ethyl for Treatment of Elevated Triglyceide Levels," Annals of Pharmacotheraphy, 47(11):1517-1523 (Nov. 2013/epub Nov. 5, 2013).

Nelson JR, Wani O, May HT, Budoff M. Potential benefits of eicosapentaenoic acid on atherosclerotic plaques. Vascul Pharmacol. 91:1-9 (publication date Apr. 2017; epublication date Mar. 2, 2017).

Nichols GA, Philip S, Reynolds K, Granowitz CB, Fazio S. Increased cardiovascular risk in hypertriglyceridemic patients with statin-controlled LDL cholesterol. J Clin Endocrinol Metab 103(8):3019-27 (publication date Aug. 1, 2018; epublication date May 29, 2018).

Nichols GA, Philip S, Reynolds K, Granowitz CB, Fazio S. Increased residual cardiovascular risk in patients with diabetes and high vs. normal triglycerides despite statin-controlled LDL Cholesterol. Diabetes Obes Metab (publication date Sep. 17, 2018; epublication date Sep. 17, 2018).

Nobukata, H., et al., "Long-term administration of highly purified eicosapentaenoic acid ethyl ester improves the dysfunction of vascular endothelial and smooth muscle cells in male WBN/Kob rats." Metabolism, 49(12): 1588-1591 (Dec. 2000).

Otvos et al., "Clinical Implications of Discordance Between LDL Cholesterol and LDL Particle Number," J. Clin. Lipidol, 5(2):105-113 (Mar.-Apr. 2011)(available online Mar. 1, 2011).

Richter, Werner O., "Hypertriglyceridamie: Ein klinischer•Leitfaden," Wissenschaftliche Verlagsgesellschaft mbH Stuttgart, front page to p. V, pp. 2 to 55, 64 to 85, 90 to 97 (2008) (with English Summary).

Ridker PM, Everett BM, Thuren T, et al. Antiinflammatory Therapy with canakinumab for atherosclerotic disease. N Engl J Med 377(12):1119-31 (publication date Sep. 21, 2017; epublication date Aug. 27, 2017).

Roe MT, Armstrong PW, Fox KAA, et al: TRILOGY ACS Investigators. Prasugrel versus clopidogrel for acute coronary syndromes without revascularization. *N Engl J Med.* 367(14):1297-1309 (publication date Oct. 4, 2012; epublication Aug. 25, 2012).

Rupp, "Omega-3-Fettsauren in der Sekundarprevention nach Myokardinfarkt," Clin. Res. Cardiol., vol. 95:Suppl. 6, Vi/12/-V1-16 (2006)(with English summary).

Schwartz GG, Bessac L, Berdan LG, et al. Effect of alirocumab, a monoclonal antibody to PCSK9, on long-term cardiovascular outcomes following acute coronary syndromes: rationale and design of the ODYSSEY outcomes trial. Am Heart J 168(5):682-9 (publication date Nov. 2014, epublication date Aug. 7, 2017).

Shearer et al., "Red Blood Cell Fatty Acid Patters and Acute Coronary Syndrome," PLoS ONE 4(5): e5444 (doi:10.1371/journal/pone.0005444)(May 6, 2009).

Sherratt SCR, Mason RP. Eiconsapentaenoic acid and docosahexaenoic acid have distinct membrane locations and lipid interactions as determined by X-ray diffraction. Chem Phys Lipids 212:73-9 (publication date May 2018, epublication date Jan. 31, 2018).

Steg PG, Bhatt DL, Wilson PWF, et al; REACH Registry Investigators. One-year cardiovascular event rates in outpatients with atherothrombosis. *JAMA.* 297(11)1197-1206 (publication date May 21, 2007).

Stielow et al., "Novel Nox Inhibitor of oxLDL-Induced Reactive Oxygen Specis Formation in Human Endothelial Cells," Biochem. Biophys. Res. Comm., 344:200-205 (May 26, 2006/epub Mar. 26, 2006).

Thomas et al., "Renal Failure—Measuring the Glomerular Filtration Rate," Dtsch Arztebl Int., Dec. 18, 2009, 106(51-52); 849-54.

Toth PP, Granowitz C, Hull M, Liassou D, Anderson A, Philip S. High Triglycerides are associated with increased cardiovascular events, medical costs, and resource use: A real-world administrative claims analysis of statin-treated patients with high residual cardiovascular risk. Journal of the American Heart Association, 7(15):e008740 (publication date Jul. 25, 2018; epublication Aug. 7, 2018).

Vaduganathan M, Venkataramani AS, Bhatt DL. Moving toward global primordial prevention in cardiovascular disease: The heart of the matter. J Am Coll Cardiol Oct. 6, 2015;66(14):1535-7.

Verma S, Leiter LA, Bhatt DL. CANTOS ushers in a new calculus of inflammasome targeting for vascular protection-and maybe more. Cell Metab 26(5):703-5 (publication date Nov. 7, 2017; epublication date Oct. 19, 2017).

Watanabe T, Ando K, Daidoji H, et al. A randomized controlled trial of eicosapentaenoic acid in patients with coronary heart disease on statins. J Cardiol 70(6):537-44 (publication date Dec. 2017; epublication date Aug. 31, 2017).

Wei LJ, Lin DY, Weissfeld L. Regression analysis of multivariate incomplete failure time data by modeling marginal distributions. *J Am Stat Assoc.* 84(408):1065-1073 (publication date Dec. 1989).

Yao et al., "Oxidized high density lipoprotein induces macrophage apoptosis via toll-like receptor 4-dependent CHOIP pathway," Journ. Lipid Res., 58:164-177 (Jan. 2017)(First published Nov. 28, 2016).

\* cited by examiner

METHODS OF REDUCING APOLIPOPROTEIN C-III

CROSS-REFERENCE TO RELATED APPLICATIONS

This application is a continuation of U.S. patent application Ser. No. 14/261,160 filed on Apr. 24, 2014, which is a continuation-in-part of U.S. patent application Ser. No. 14/173,155 filed on Feb. 5, 2014 (now U.S. Pat. No. 9,452,151), the entire contents of each of which are incorporated herein by reference and relied upon.

BACKGROUND

Cardiovascular disease is one of the leading causes of death in the United States and most European countries. It is estimated that over 70 million people in the United States alone suffer from a cardiovascular disease or disorder including but not limited to high blood pressure, coronary heart disease, dyslipidemia, congestive heart failure and stroke. A need exists for improved treatments for cardiovascular diseases and disorders.

SUMMARY

In various embodiments, the present invention provides methods of treating and/or preventing cardiovascular-related diseases and, in particular, a method of blood lipid therapy comprising administering to a subject in need thereof a pharmaceutical composition comprising eicosapentaenoic acid or a derivative thereof. In one embodiment, the method comprises administering to a subject about 2 g to about 4 g per day (e.g., about 3.8 g to about 4 g per day) of eicosapentaenoic acid or derivative thereof.

In one embodiment, the composition contains not more than 10%, by weight, docosahexaenoic acid or derivative thereof, substantially no docosahexaenoic acid or derivative thereof, or no docosahexaenoic acid or derivative thereof. In another embodiment, eicosapentaenoic acid ethyl ester comprises at least 90%, by weight, of all fatty acids present in the composition. In one embodiment, the present invention provides methods of reducing the level of apolipoprotein C-III (also referred to as Apolipoprotein C3 or ApoC3) in a subject compared to baseline or to placebo control.

In one embodiment, a pharmaceutical composition useful in accordance with the invention comprises, consists of or consists essentially of at least 95% by weight ethyl eicosapentaenoate (EPA-E), about 0.2% to about 0.5% by weight ethyl octadecatetraenoate (ODTA-E), about 0.05% to about 0.25% by weight ethyl nonaecapentaenoate (NDPA-E), about 0.2% to about 0.45% by weight ethyl arachidonate (AA-E), about 0.3% to about 0.5% by weight ethyl eicosatetraenoate (ETA-E), and about 0.05% to about 0.32% ethyl heneicosapentaenoate (HPA-E). In another embodiment, the composition is present in a capsule shell. In another embodiment, the composition contains substantially no or no amount of docosahexaenoic acid (DHA) or derivative thereof such as ethyl-DHA (DHA-E).

In another embodiment, the invention provides a method of treating moderate to severe hypertriglyceridemia comprising administering a composition as described herein to a subject in need thereof one to about four times per day.

These and other embodiments of the present invention will be disclosed in further detail herein below.

DETAILED DESCRIPTION

Figure 1:
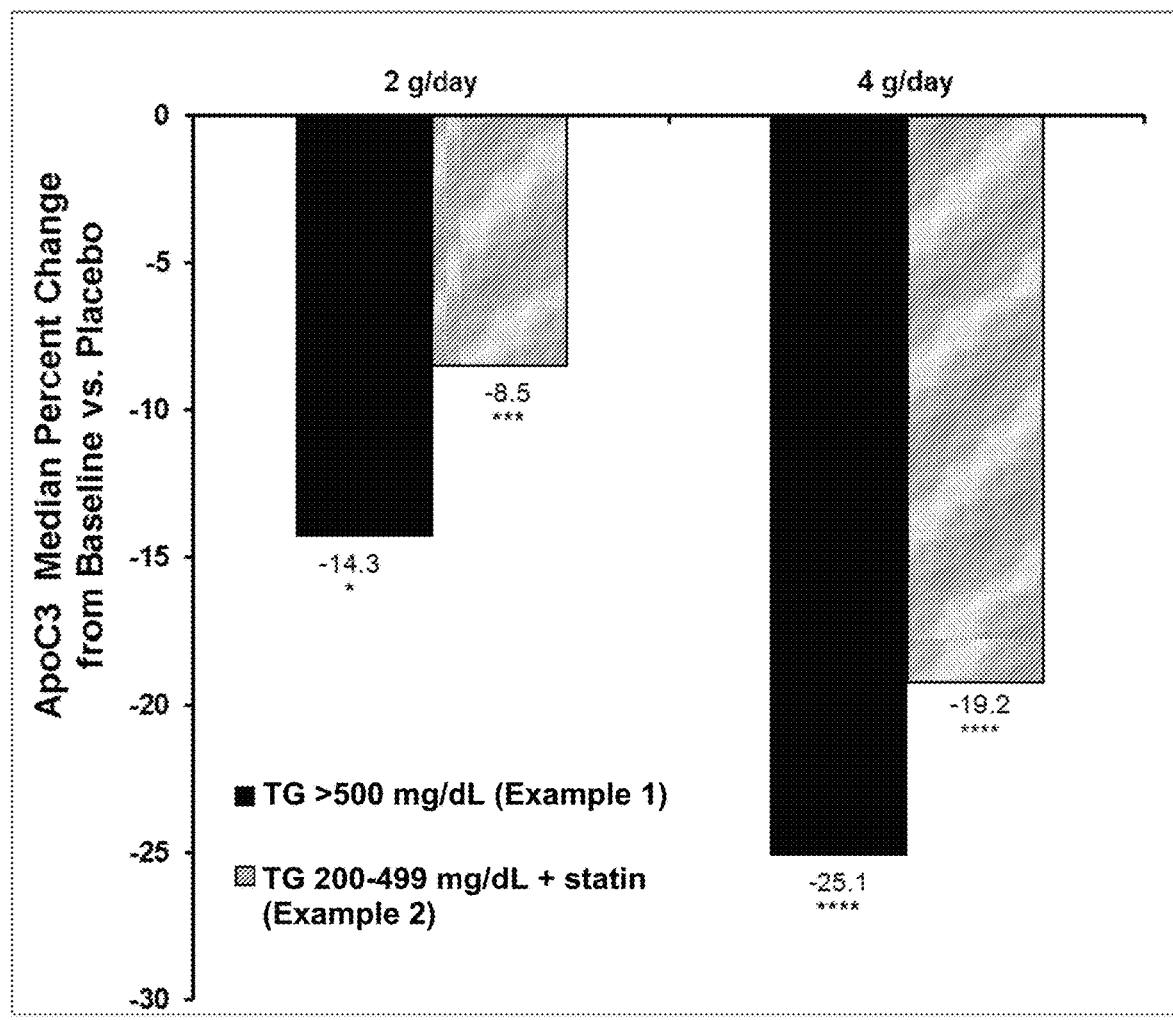
FIG. 1 depicts reductions in total apolipoprotein C3 values for subjects having fasting triglyceride levels ≥500 mg/dL (solid) and subjects on statin therapy having fasting triglyceride levels of 200-499 mg/dL (hashed) after being administered 2 g/day or 4 g/day of a composition according to the present disclosure (AMR101).

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

In one embodiment, the invention provides a method for treatment and/or prevention of a cardiovascular-related disease. The term "cardiovascular-related disease" herein refers to any disease or disorder of the heart or blood vessels (i.e. arteries and veins) or any symptom thereof. Non-limiting examples of cardiovascular-related disease and disorders include hypertriglyceridemia, hypercholesterolemia, mixed dyslipidemia, coronary heart disease, vascular disease, stroke, atherosclerosis, arrhythmia, hypertension, myocardial infarction, and other cardiovascular events.

The term "treatment" in relation a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving, preventing or treating symptoms of the disease or disorder. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

In one embodiment, the present invention provides a method of blood lipid therapy comprising administering to a subject or subject group in need thereof a pharmaceutical composition as described herein. In another embodiment, the subject or subject group has hypertriglyceridemia, hypercholesterolemia, mixed dyslipidemia and/or very high triglycerides.

In another embodiment, the subject or subject group being treated has a baseline triglyceride level (or mean or median baseline triglyceride level in the case of a subject group), fed or fasting, of about 200 mg/dl to about 499 mg/dl. In another embodiment, the subject or subject group has a baseline LDL-C level (or mean or median baseline LDL-C level), despite stable statin therapy, of about 40 mg/dl to about 115 or about 40 to about 100 mg/dl.

In one embodiment, the subject or subject group being treated in accordance with methods of the invention is on concomitant statin therapy, for example atorvastatin, rosuvastatin or simvastatin therapy (with or without ezetimibe). In another embodiment, the subject is on concomitant stable statin therapy at time of initiation of EPA therapy.

In another embodiment, the subject or subject group being treated in accordance with methods of the invention has a body mass index (BMI or mean BMI) of not more than about 45 kg/m².

In one embodiment, the invention provides a method of lowering triglycerides in a subject on stable statin therapy having baseline fasting triglycerides of about 200 mg/dl to about 499 mg/dl, the method comprising administering to the subject a pharmaceutical composition comprising about 1 g to about 4 g of EPA or a derivative thereof, wherein upon administering the composition to the subject daily for a period of 1 to about 12 weeks the subject exhibits at least 10%, at least 15%, at least 20%, at least 25%, at least 30%, at least 35%, at least 40%, at least 45%, at least 50%, at least 55%, at least 60%, at least 65%, at least 70%, or at least 75% lower fasting triglycerides than a control subject maintained on stable statin therapy (and optionally placebo matching the EPA) without concomitant EPA for a period of 1 to about 12 weeks, wherein the control subject also has baseline fasting triglycerides of about 200 mg/dl to about 500 mg/dl. The term "stable statin therapy" herein means that the subject, subject group, control subject or control subject group in question has been taking a stable daily dose of a statin (e.g. atorvastatin, rosuvastatin or simvastatin) for at least 4 weeks prior to the baseline fasting triglyceride measurement (the "qualifying period"). For example, a subject or control subject on stable statin therapy would receive a constant daily (i.e. the same dose each day) statin dose for at least 4 weeks immediately prior to baseline fasting triglyceride measurement. In one embodiment, the subject's and control subject's LDL-C is maintained between about 40 mg/dl and about 115 mg/dl or about 40 mg/dl to about 100 mg/dl during the qualifying period. The subject and control subject are then continued on their stable statin dose for the 12 week period post baseline.

In one embodiment, the statin is administered to the subject and the control subject in an amount of about 1 mg to about 500 mg, about 5 mg to about 200 mg, or about 10 mg to about 100 mg, for example about 1 mg, about 2 mg, about 3 mg, about 4 mg, about 5 mg, about 6 mg, about 7 mg, about 8 mg, about 9 mg, or about 10 mg; about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg. In another embodiment, the subject (and optionally the control subject) has a baseline LDL-C level, despite stable statin therapy, of about 40 mg/dl to about 115 mg/dl or about 40 mg/dl to about 100 mg/dl. In another embodiment, the subject and/or control subject has a body mass index (BMI; or mean BMI) of not more than about 45 kg/m².

In another embodiment, the invention provides a method of lowering triglycerides in a subject group on stable statin therapy having mean baseline fasting triglycerides of about 200 mg/dl to about 499 mg/dl, the method comprising administering to members of the subject group a pharmaceutical composition comprising about 1 g to about 4 g of EPA per day, wherein upon administering the composition to the members of the subject group daily for a period of 1 to about 12 weeks the subject group exhibits at least 10%, at least 15%, at least 20%, at least 25%, at least 30%, at least 35%, at least 40%, at least 45%, at least 50%, at least 55%, at least 60%, at least 65%, at least 70%, at least 75% lower mean fasting triglycerides than a control subject group maintained on stable statin therapy without concomitant EPA (optionally with matching placebo) for a period of 1 to about 12 weeks, wherein the control subject group also has mean baseline fasting triglycerides of about 200 mg/dl to about 499 mg/dl. In a related embodiment, the stable statin therapy will be sufficient such that the subject group has a mean LDL-C level about at least about 40 mg/dl and not more than about 100 mg/dl or about 40 mg/dl to about 100 mg/dl for the 4 weeks immediately prior to the baseline fasting triglyceride measurement.

In another embodiment, the invention provides a method of lowering triglycerides in subject group on stable statin therapy and having a mean baseline fasting triglyceride level of about 200 mg/dl to about 499 mg/dl, the method comprising administering to members of the subject group a pharmaceutical composition comprising about 1 g to about 4 g of EPA, wherein upon administering the composition to members of the subject group daily for a period of 1 to about 12 weeks the subject group exhibits: (a) at least 10%, at least 15%, at least 20%, at least 25%, at least 30%, at least 35%, at least 40%, at least 45%, at least 50%, at least 55%, at least 60%, at least 65%, at least 70%, at least 75% lower mean fasting triglycerides by comparison with a control subject group maintained on stable statin therapy without concomitant EPA (optionally with matching placebo) for a period of 1 to about 12 weeks, and (b) no serum LDL-C increase, no statistically significant serum LDL-C increase, a serum LDL-C decrease, or the subject is statistically non-inferior to the control subjects (statin plus optional placebo) in regard to serum LDL-C elevation) no increase in mean serum LDL-C levels compared to baseline, wherein the control subject also has mean baseline fasting triglycerides of about 200 mg/dl to about 499 mg/dl.

In another embodiment, the invention provides a method of lowering triglycerides in subject on stable statin therapy and having mean baseline fasting triglyceride level of about 200 mg/dl to about 499 mg/dl, the method comprising administering to the subject a pharmaceutical composition comprising about 1 g to about 4 g of EPA, wherein upon administering the composition to the subject daily for a period of 1 to about 12 weeks the subject exhibits (a) at least 10%, at least 15%, at least 20%, at least 25%, at least 30%, at least 35%, at least 40%, at least 45%, at least 50%, at least 55%, at least 60%, at least 65%, at least 70%, or at least 75% lower fasting triglycerides by comparison with a control subject maintained on stable statin therapy without concomitant EPA for a period of 1 to about 12 weeks and (b) no increase in serum LDL-C levels compared to baseline, wherein the control subject also has baseline fasting triglycerides of about 200 mg/dl to about 499 mg/dl.

In another embodiment, the invention provides a method of lowering triglycerides in subject group on stable statin therapy and having mean baseline fasting triglyceride level of about 200 mg/dl to about 499 mg/dl, the method comprising administering to members of the subject group a pharmaceutical composition comprising about 1 g to about 4 g of EPA, wherein upon administering the composition to the members of the subject group daily for a period of 1 to about 12 weeks the subject group exhibits: (a) at least 10%, at least 15%, at least 20%, at least 25%, at least 30%, at least 35%, at least 40%, at least 45%, at least 50%, at least 55%, at least 60%, at least 65%, at least 70%, at least 75% lower mean fasting triglycerides and (b) at least 5%, at least 10%, at least 15%, at least 20%, at least 25%, at least 30%, at least 35%, at least 40%, at least 45% or at least 50% lower mean serum LDL-C levels by comparison with a control subject group maintained on stable statin therapy without concomitant EPA (optionally with matching placebo) for a period of 1 to about 12 weeks, no serum LDL-C increase, no statistically significant serum LDL-C increase, no statistically significant serum LDL-C increase, a serum LDL-C decrease, or the subject group is statistically non-inferior to the control subject group (statin plus optional placebo) in regard to serum LDL-C elevation), wherein the control subject group also has mean baseline fasting triglycerides of about 200 mg/dl to about 499 mg/dl.

In another embodiment, the invention provides a method of lowering triglycerides in subject group on stable statin therapy and having mean baseline fasting triglyceride level of about 200 mg/dl to about 499 mg/dl, the method comprising administering to members of the subject group a pharmaceutical composition comprising about 1 g to about 4 g of EPA, wherein upon administering the composition to the members of the subject group daily for a period of 1 to about 12 weeks the subject group exhibits (a) at least 10%, at least 15%, at least 20%, at least 25%, at least 30%, at least 35%, at least 40%, at least 45%, at least 50%, at least 55%, at least 60%, at least 65%, at least 70%, at least 75% lower mean fasting triglycerides and (b) at least 5%, at least 10%, at least 15%, at least 20%, at least 25%, at least 30%, at least 35%, at least 40%, at least 45% or at least 50% lower mean serum LDL-C levels by comparison with a control subject group maintained on stable statin therapy without concomitant EPA (optionally with matching placebo) for a period of 1 to about 12 weeks, no serum LDL-C increase, no statistically significant serum LDL-C increase, no statistically significant serum LDL-C increase, a serum LDL-C decrease, or the subject group is statistically non-inferior to the control subject group (statin plus optional placebo) in regard to serum LDL-C elevation), wherein the control subject group also has mean baseline fasting triglycerides of about 200 mg/dl to about 500 mg/dl.

In another embodiment, the subject or subject group being treated in accordance with methods of the invention exhibits a fasting baseline absolute plasma level of free total fatty acid (or mean thereof) not greater than about 300 nmol/ml, not greater than about 250 nmol/ml, not greater than about 200 nmol/ml, not greater than about 150 nmol/ml, not greater than about 100 nmol/ml, or not greater than about 50 nmol/ml.

In another embodiment, the subject or subject group being treated has a baseline triglyceride level (or median baseline triglyceride level in the case of a subject group), fed or fasting, of at least about 300 mg/dl, at least about 400 mg/dl, at least about 500 mg/dl, at least about 600 mg/dl, at least about 700 mg/dl, at least about 800 mg/dl, at least about 900 mg/dl, at least about 1000 mg/dl, at least about 1100 mg/dl, at least about 1200 mg/dl, at least about 1300 mg/dl, at least about 1400 mg/dl, or at least about 1500 mg/dl, for example about 200 mg/dl to about 499 mg/dl, about 400 mg/dl to about 2500 mg/dl, about 450 mg/dl to about 2000 mg/dl or about 500 mg/dl to about 1500 mg/dl.

In one embodiment, the subject or subject group being treated in accordance with methods of the invention has previously been treated with Lovaza® and has experienced an increase in, or no decrease in, LDL-C levels and/or non-HDL-C levels. In one such embodiment, Lovaza® therapy is discontinued and replaced by a method of the present invention.

In another embodiment, the subject or subject group being treated in accordance with methods of the invention exhibits a fasting baseline absolute plasma level of free EPA (or mean thereof in the case of a subject group) not greater than about 0.70 nmol/ml, not greater than about 0.65 nmol/ml, not greater than about 0.60 nmol/ml, not greater than about 0.55 nmol/ml, not greater than about 0.50 nmol/ml, not greater than about 0.45 nmol/ml, or not greater than about 0.40 nmol/ml. In another embodiment, the subject or subject group being treated in accordance with methods of the invention exhibits a baseline fasting plasma level (or mean thereof) of free EPA, expressed as a percentage of total free fatty acid, of not more than about 3%, not more than about 2.5%, not more than about 2%, not more than about 1.5%, not more than about 1%, not more than about 0.75%, not more than about 0.5%, not more than about 0.25%, not more than about 0.2% or not more than about 0.15%. In one such embodiment, free plasma EPA and/or total fatty acid levels are determined prior to initiating therapy.

In another embodiment, the subject or subject group being treated in accordance with methods of the invention exhibits a fasting baseline absolute plasma level of total fatty acid (or mean thereof) not greater than about 250 nmol/ml, not greater than about 200 nmol/ml, not greater than about 150 nmol/ml, not greater than about 100 nmol/ml, or not greater than about 50 nmol/ml.

In another embodiment, the subject or subject group being treated in accordance with methods of the invention exhibits a fasting baseline plasma, serum or red blood cell membrane EPA level not greater than about 70 μg/ml, not greater than about 60 μg/ml, not greater than about 50 μg/ml, not greater than about 40 μg/ml, not greater than about 30 μg/ml, or not greater than about 25 μg/ml.

In another embodiment, methods of the present invention comprise a step of measuring the subject's (or subject group's mean) baseline lipid profile prior to initiating therapy. In another embodiment, methods of the invention comprise the step of identifying a subject or subject group having one or more of the following: baseline non-HDL-C value of about 200 mg/dl to about 400 mg/dl, for example at least about 210 mg/dl, at least about 220 mg/dl, at least about 230 mg/dl, at least about 240 mg/dl, at least about 250 mg/dl, at least about 260 mg/dl, at least about 270 mg/dl, at least about 280 mg/dl, at least about 290 mg/dl, or at least about 300 mg/dl; baseline total cholesterol value of about 250 mg/dl to about 400 mg/dl, for example at least about 260 mg/dl, at least about 270 mg/dl, at least about 280 mg/dl or at least about 290 mg/dl; baseline vLDL-C value of about 140 mg/dl to about 200 mg/dl, for example at least about 150 mg/dl, at least about 160 mg/dl, at least about 170 mg/dl, at least about 180 mg/dl or at least about 190 mg/dl; baseline HDL-C value of about 10 to about 60 mg/dl, for example not more than about 40 mg/dl, not more than about 35 mg/dl, not more than about 30 mg/dl, not more than about 25 mg/dl, not more than about 20 mg/dl, or not more than about 15 mg/dl; and/or baseline LDL-C value of about 50 to about 300 mg/dl, for example not less than about 100 mg/dl, not less than about 90 mg/dl, not less than about 80 mg/dl, not less than about 70 mg/dl, not less than about 60 mg/dl or not less than about 50 mg/dl.

In a related embodiment, upon treatment in accordance with the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits one or more of the following outcomes:

(a) reduced triglyceride levels compared to baseline or placebo control;

(b) reduced Apo B levels compared to baseline or placebo control;

(c) increased HDL-C levels compared to baseline or placebo control;

(d) no increase in LDL-C levels compared to baseline or placebo control;

(e) a reduction in LDL-C levels compared to baseline or placebo control;

(f) a reduction in non-HDL-C levels compared to baseline or placebo control;

(g) a reduction in vLDL levels compared to baseline or placebo control;

(h) an increase in apo A-I levels compared to baseline or placebo control;

(i) an increase in apo A-I/apo B ratio compared to baseline or placebo control;

(j) a reduction in lipoprotein A levels compared to baseline or placebo control;

(k) a reduction in LDL particle number compared to baseline or placebo control;

(l) an increase in LDL size compared to baseline or placebo control;

(m) a reduction in remnant-like particle cholesterol compared to baseline or placebo control;

(n) a reduction in oxidized LDL compared to baseline or placebo control;

(o) no change or a reduction in fasting plasma glucose (FPG) compared to baseline or placebo control;

(p) a reduction in hemoglobin $A_{1c}$ (Hb$A_{1c}$) compared to baseline or placebo control;

(q) a reduction in homeostasis model insulin resistance compared to baseline or placebo control;

(r) a reduction in lipoprotein associated phospholipase A2 compared to baseline or placebo control;

(s) a reduction in intracellular adhesion molecule-1 compared to baseline or placebo control;

(t) a reduction in interleukin-6 compared to baseline or placebo control;

(u) a reduction in plasminogen activator inhibitor-1 compared to baseline or placebo control;

(v) a reduction in high sensitivity C-reactive protein (hsCRP) compared to baseline or placebo control;

(w) an increase in serum or plasma EPA compared to baseline;

(x) an increase in red blood cell (RBC) membrane EPA compared to baseline or placebo control;

(y) a reduction or increase in one or more of serum phospholipid and/or red blood cell content of docosahexaenoic acid (DHA), docosapentaenoic acid (DPA), arachidonic acid (AA), palmitic acid (PA), staeridonic acid (SA) or oleic acid (OA) compared to baseline or placebo control;

(z) a reduction in one or more protein components of VLDL such as apolipoprotein C-III (hereinafter "APOC3"; also referred to as APOCIII or HALP2) compared to baseline or placebo control;

(aa) no significant increase in, or a reduction in HDL-APOC3, compared to baseline or placebo control; and/or (bb) no significant increase in, or a reduction in non-HDL-APOC3, compared to baseline or placebo control.

In one embodiment, upon administering a composition of the invention to a subject, the subject exhibits a decrease in triglyceride levels, an increase in the concentrations of EPA and DPA (n-3) in red blood cells, and an increase of the ratio of EPA: arachidonic acid in red blood cells. In a related embodiment the subject exhibits substantially no or no increase in RBC DHA.

In one embodiment, methods of the present invention comprise measuring baseline levels of one or more markers set forth in (a)-(bb) above prior to dosing the subject or subject group. In another embodiment, the methods comprise administering a composition as disclosed herein to the subject after baseline levels of one or more markers set forth in (a)-(bb) are determined, and subsequently taking an additional measurement of said one or more markers.

In another embodiment, upon treatment with a composition of the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits any 2 or more of, any 3 or more of, any 4 or more of, any 5 or more of, any 6 or more of, any 7 or more of, any 8 or more of, any 9 or more of, any 10 or more of, any 11 or more of, any 12 or more of, any 13 or more of, any 14 or more of, any 15 or more of, any 16 or more of, any 17 or more of, any 18 or more of, any 19 or more of, any 20 or more of, any 21 or more of, any 22 or more of, any 23 or more of, any 24 or more of, any 25 or more of, any 26 or more of, any 27 or more of, or all 28 of outcomes (a)-(bb) described immediately above.

In another embodiment, upon treatment with a composition of the present invention, the subject or subject group exhibits one or more of the following outcomes:

(a) a reduction in triglyceride level of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or placebo control;

(b) a less than 30% increase, less than 20% increase, less than 10% increase, less than 5% increase or no increase in non-HDL-C levels or a reduction in non-HDL-C levels of at least about 1%, at least about 3%, at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or placebo control;

(c) substantially no change in HDL-C levels, no change in HDL-C levels, or an increase in HDL-C levels of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or placebo control;

(d) a less than 60% increase, a less than 50% increase, a less than 40% increase, a less than 30% increase, less than 20% increase, less than 10% increase, less than 5% increase or no increase in LDL-C levels or a reduction in LDL-C levels of at least about 5%, at least about 10%, at least about 15%, at least about 20%, at least about 25%, at least about 30%, at least about 35%, at least about 40%, at least about 45%, at least about 50%, at least about 55%, at least about 55% or at least about 75% (actual % change or median % change) as compared to baseline or placebo control;

(e) a decrease in Apo B levels of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or placebo control;

(f) a reduction in vLDL levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(g) an increase in apo A-I levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(h) an increase in apo A-I/apo B ratio of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(i) a reduction in lipoprotein (a) levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(j) a reduction in mean LDL particle number of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(k) an increase in mean LDL particle size of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(l) a reduction in remnant-like particle cholesterol of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(m) a reduction in oxidized LDL of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(n) substantially no change, no significant change, or a reduction (e.g. in the case of a diabetic subject) in fasting plasma glucose (FPG) of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(o) substantially no change, no significant change or a reduction in hemoglobin $A_{1c}$ ($HbA_{1c}$) of at least about 5%, at least about 10%, at least about 15%, at least about 20%, at least about 25%, at least about 30%, at least about 35%, at least about 40%, at least about 45%, or at least about 50% (actual % change or median % change) compared to baseline or placebo control;

(p) a reduction in homeostasis model index insulin resistance of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(q) a reduction in lipoprotein associated phospholipase A2 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(r) a reduction in intracellular adhesion molecule-1 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(s) a reduction in interleukin-6 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(t) a reduction in plasminogen activator inhibitor-1 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(u) a reduction in high sensitivity C-reactive protein (hsCRP) of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or placebo control;

(v) an increase in serum, plasma and/or RBC EPA of at least about 5%, at least about 10%, at least about 15%, at least about 20%, at least about 25%, at least about 30%, at least about 35%, at least about 40%, at least about 45%, at least about 50%, at least about 100%, at least about 200% or at least about 400% (actual % change or median % change) compared to baseline or placebo control;

(w) an increase in serum phospholipid and/or red blood cell membrane EPA of at least about 5%, at least about 10%, at least about 15%, at least about 20%, at least about 25%, at least about 30%, at least about 35%, at least about 40%, at least about 45%, r at least about 50%, at least about 100%, at least about 200%, or at least about 400% (actual % change or median % change) compared to baseline or placebo control;

(x) a reduction or increase in one or more of serum phospholipid and/or red blood cell DHA, DPA, AA, PA and/or OA of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) compared to baseline or placebo control;

(y) a reduction in total cholesterol of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) compared to baseline or placebo control;

(z) no significant increase in, or a reduction in one or more protein components of VLDL such as APOC3, of at least about 0.2%, at least about 0.3%, at least about 0.5%, at least about 0.6%, at least about 1%, at least about 5%, at least about 8%, at least about 8.5%, at least about 9%, at least about 9.4%, at least about 10%, at least about 10.1%, at least about 14.3%, at least about 15%, at least about 19%, at least about 19.2%, at least about 20%, at least about 25%, at least about 25.1%, at least about 30%, at least about 35%, at least about 40%, at least about 45%, at least about 50%, at least about 55%, at least about 65%, at least about 70%, at least about 75%, at least about 80%, at least about 85%, at least about 90%, at least about 95%, at least about 100%, at least about 105%, at least about 110%, at least about 115%, at least about 120%, at least about 125%, at least about 130%, at least about 135%, at least about 140%, at least about 145%, at least about 150%, at least about 155%, at least about 160%, at least about 165%, at least about 170%, at least about 175%, at least about 180%, at least about 185%, at least about 190%, at least about 195%, or at least about 200% (actual % change or median % change) compared to baseline or placebo control;

(aa) no significant increase in, or a reduction in HDL-APOC3, of at least about 0.2%, at least about 0.3%, at least about 0.5%, at least about 0.6%, at least about 1%, at least about 5%, at least about 5.9%, at least about 8%, at least about 9%, at least about 10%, at least about 15%, at least about 20%, at least about 21%, at least about 21.4%, at least about 23%, at least about 23.3%, at least about 25%, at least about 30%, at least about 35%, at least about 40%, at least about 45%, at least about 50%, at least about 55%, at least about 65%, at least about 70%, at least about 75%, at least about 80%, at least about 85%, at least about 90%, at least about 95%, at least about 100%, at least about 105%, at least about 110%, at least about 115%, at least about 120%, at least about 125%, at least about 130%, at least about 135%, at least about 140%, at least about 145%, at least about 150%, at least about 155%, at least about 160%, at least about 165%, at least about 170%, at least about 175%, at least about 180%, at least about 185%, at least about 190%, at least about 195%, or at least about 200% (actual % change or median % change) compared to baseline or placebo control; and/or (bb) no significant increase in, or a reduction in non-HDL-APOC3, of at least about 0.2%, at least about 0.3%, at least about 0.5%, at least about 0.6%, at least about 1%, at least about 1.4%, at least about 5%, at least about 5.4%, at least about 8%, at least about 9%, at least about 10%, at least about 15%, at least about 20%, at least about 22%, at least about 22.5%, at least about 25%, at least about 30%, at least about 31%, at least about 31.8%, at least about 35%, at least about 40%, at least about 45%, at least about 50%, at least about 55%, at least about 65%, at least about 70%, at least about 75%, at least about 80%, at least about 85%, at least about 90%, at least about 95%, at least about 100%, at least about 105%, at least about 110%, at least about 115%, at least about 120%, at least about 125%, at least about 130%, at least about 135%, at least about 140%, at least about 145%, at least about 150%, at least about 155%, at least about 160%, at least about 165%, at least about 170%, at least about 175%, at least about 180%, at least about 185%, at least about 190%, at least about 195%, or at least about 200% (actual % change or median % change) compared to baseline or placebo control.

In one embodiment, methods of the present invention comprise measuring baseline levels of one or more markers set forth in (a)-(bb) prior to dosing the subject or subject group. In another embodiment, the methods comprise administering a composition as disclosed herein to the subject after baseline levels of one or more markers set forth in (a)-(bb) are determined, and subsequently taking a second measurement of the one or more markers as measured at baseline for comparison thereto.

In another embodiment, upon treatment with a composition of the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits any 2 or more of, any 3 or more of, any 4 or more of, any 5 or more of, any 6 or more of, any 7 or more of, any 8 or more of, any 9 or more of, any 10 or more of, any 11 or more of, any 12 or more of, any 13 or more of, any 14 or more of, any 15 or more of, any 16 or more of, any 17 or more of, any 18 or more of, any 19 or more of, any 20 or more of, any 21 or more of, any 22 or more of, any 23 or more of, any 24 or more of, any 25 or more of, any 26 or more of, any 27 or more of, or all 28 of outcomes (a)-(bb) described immediately above.

Parameters (a)-(bb) can be measured in accordance with any clinically acceptable methodology. For example, triglycerides, total cholesterol, HDL-C and fasting blood sugar can be sample from serum and analyzed using standard photometry techniques. VLDL-TG, LDL-C and VLDL-C can be calculated or determined using serum lipoprotein fractionation by preparative ultracentrifugation and subsequent quantitative analysis by refractometry or by analytic ultracentrifugal methodology. Apo A1, Apo B and hsCRP can be determined from serum using standard nephelometry techniques. Lipoprotein (a) can be determined from serum using standard turbidimetric immunoassay techniques. LDL particle number and particle size can be determined using nuclear magnetic resonance (NMR) spectrometry. Remnants lipoproteins and LDL-phospholipase A2 can be determined from EDTA plasma or serum and serum, respectively, using enzymatic immunoseparation techniques. Oxidized LDL, intercellular adhesion molecule-1 and interleukin-6 levels can be determined from serum using standard enzyme immunoassay techniques. APOC3 levels can be determined by known quantitative methods including, for example, antibody-based assays such as ELISA. These techniques are described in detail in standard textbooks, for example Tietz Fundamentals of Clinical Chemistry, $6^{th}$ Ed. (Burtis, Ashwood and Borter Eds.), WB Saunders Company.

In one embodiment, the present invention provides a method of reducing an APOC3 level of a subject having baseline fasting triglycerides of about 200 mg/dl to about 499 mg/dl and on statin therapy (e.g., stable statin therapy), the method comprising administering to the subject a pharmaceutical composition comprising about 1 g to about 4 g of EPA per day, wherein upon administering the composition to the subject daily for a period of 1 to about 12 weeks, the subject exhibits a decrease in APOC3 of at least about 5% compared to a control subject on stable statin therapy without EPA, wherein the control subject also has baseline fasting triglycerides of about 200 mg/dl to about 499 mg/dl. In some embodiments, the decrease in APOC3 level is at least about 7.6%, at least about 10%, at least about 13.1%, at least about 25%, at least about 50%, at least about 75%, at least about 100%, at least about 125%, at least about 150%, at least about 175%, or at least about 200%. In some embodiments, the subject is administered about 2 g per day of EPA. In some embodiments, the subject is administered about 3.8 g to about 4 g per day of EPA. In any of the methods described herein, the EPA can be ethyl eicosapentaenoate. In some embodiments, the subject exhibits a decrease in HDL-ApoC3 of at least about 5%, at least about 10%, at least about 15%, at least about 20%, at least about 21%, about 21.4%, or at least about 25% compared to baseline. In some embodiments, the subject exhibits a decrease in HDL-ApoC3 of at least about 5%, at least about 10%, at least about 15%, at least about 20%, at least about 23%, about 23.3%, at least about 25% compared to the control subject. In some embodiments, the subject exhibits a decrease in non-HDL-ApoC3 of at least about 5%, about 5.4%, at least about 10%, at least about 15%, or at least about 20% compared to baseline. In some embodiments, the subject exhibits a decrease in non-HDL-ApoC3 of at least about 5%, at least about 10%, at least about 15%, at least about 20%, at least about 22%, about 22.5%, at least about 25%, at least about 30%, at least about 31%, about 31.8%, or at least about 35% compared to the control subject.

Apolipoprotein C-III (APOC3, APOCIII or HALP2) is a 9-kDa protein component of VLDL. It is synthesized in the liver and is known to inhibit lipoprotein lipase and hepatic lipase, and is additionally believed to inhibit hepatic uptake of triglyceride-rich particles by modulating the binding of chylomicron remnants and VLDL to receptors. Accordingly, APOC3 is thought to inhibit the clearance of triglycerides from the blood. APOC3 is typically glycosylated; at least three polymorphic forms with varying amounts of sialic acid have been identified (Apo C-III-0, Apo C-III-1, and Apo C-III-2). Clinically, subjects with normal or non-insulin diabetes mellitus who have certain haplotypes in the ApoAI-CIII-AIV gene cluster on chromosome 11q23 have an approximately threefold higher risk of coronary heart disease. People who do not produce APOC3 have lower levels of triglycerides and lower instances of cardiovascular disease.

In one embodiment, the present invention provides a method of reducing an APOC3 level of a subject having baseline fasting triglycerides of about 500 mg/dl to about 1500 mg/dl, the method comprising administering to the subject a pharmaceutical composition comprising about 1 g to about 4 g of EPA per day, wherein upon administering the composition to the subject daily for a period of 1 to about 12 weeks, the subject exhibits a decrease in APOC3 in plasma and/or RBCs of at least about 5% compared to a control subject who has not received about 1 g to about 4 g of EPA per day, wherein the control subject also has baseline fasting triglycerides of about 500 mg/dl to about 1500 mg/dl. In some embodiments, the decrease in APOC3 level is at least about 10%, at least about 11%, at least about 14%, at least about 25%, or at least about 50%, at least about 75%, at least about 100%, at least about 125%, at least about 150%, at least about 175%, or at least about 200%. In some embodiments, the subject is administered about 2 g per day of EPA. In some embodiments, the subject is administered about 3.8 g to about 4 g per day of EPA. In any of the methods described herein, the EPA can be ethyl eicosapentaenoate. In some embodiments, the subject exhibits a decrease in HDL-ApoC3 of at least about 5% compared to baseline.

In one embodiment, subjects fast for up to 12 hours prior to blood sample collection, for example about 10 hours.

In another embodiment, the present invention provides a method of treating or preventing primary hypercholesterolemia and/or mixed dyslipidemia (Fredrickson Types IIa and IIb) in a patient in need thereof, comprising administering to the patient one or more compositions as disclosed herein. In a related embodiment, the present invention provides a method of reducing triglyceride levels in a subject or subjects when treatment with a statin or niacin extended-release monotherapy is considered inadequate (Frederickson type IV hyperlipidemia).

In another embodiment, the present invention provides a method of treating or preventing risk of recurrent nonfatal myocardial infarction in a patient with a history of myocardial infarction, comprising administering to the patient one or more compositions as disclosed herein.

In another embodiment, the present invention provides a method of slowing progression of or promoting regression of atherosclerotic disease in a patient in need thereof, comprising administering to a subject in need thereof one or more compositions as disclosed herein.

In another embodiment, the present invention provides a method of treating or preventing very high serum triglyceride levels (e.g. Types IV and V hyperlipidemia) in a patient in need thereof, comprising administering to the patient one or more compositions as disclosed herein.

In another embodiment, the present invention provides a method of treating subjects having very high serum triglyceride levels (e.g. greater than 1000 mg/dl or greater than 2000 mg/dl) and that are at risk of developing pancreatitis, comprising administering to the patient one or more compositions as disclosed herein.

In one embodiment, a composition of the invention is administered to a subject in an amount sufficient to provide a daily dose of eicosapentaenoic acid of about 1 mg to about 10,000 mg, 25 about 5000 mg, about 50 to about 3000 mg, about 75 mg to about 2500 mg, about 2 g to about 4 g, about 3.8 g to about 4 g, or about 100 mg to about 1000 mg, for example about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, about 2750 mg, about 3000 mg, about 3250 mg, about 3500 mg, about 3750 mg, about 3800 mg, about 4000 mg, about 4250 mg, about 4500 mg, about 4750 mg, about 5000 mg, about 5500 mg, about 6000 mg, about 6500 mg, about 7000 mg, about 7500 mg, about 8000 mg, about 8500 mg, about 9000 mg, about 9500 mg, or about 10,000 mg.

In another embodiment, any of the methods disclosed herein are used in treatment or prevention of a subject or subjects that consume a traditional Western diet. In one embodiment, the methods of the invention include a step of identifying a subject as a Western diet consumer or prudent diet consumer and then treating the subject if the subject is deemed a Western diet consumer. The term "Western diet" herein refers generally to a typical diet consisting of, by percentage of total calories, about 45% to about 50% carbohydrate, about 35% to about 40% fat, and about 10% to about 15% protein. A Western diet may alternately or additionally be characterized by relatively high intakes of red and processed meats, sweets, refined grains, and desserts, for example more than 50%, more than 60% or more or 70% of total calories come from these sources.

In one embodiment, a composition for use in methods of the invention comprises eicosapentaenoic acid, or a pharmaceutically acceptable ester, derivative, conjugate or salt thereof, or mixtures of any of the foregoing, collectively referred to herein as "EPA." The term "pharmaceutically acceptable" in the present context means that the substance in question does not produce unacceptable toxicity to the subject or interaction with other components of the composition.

In one embodiment, the EPA comprises all-cis eicosa-5,8,11,14,17-pentaenoic acid. In another embodiment, the EPA comprises an eicosapentaenoic acid ester. In another embodiment, the EPA comprises a $C_1$-$C_5$ alkyl ester of eicosapentaenoic acid. In another embodiment, the EPA comprises eicosapentaenoic acid ethyl ester, eicosapentaenoic acid methyl ester, eicosapentaenoic acid propyl ester, or eicosapentaenoic acid butyl ester. In another embodiment, the EPA comprises In one embodiment, the EPA comprises all-cis eicosa-5,8,11,14,17-pentaenoic acid ethyl ester.

In another embodiment, the EPA is in the form of ethyl-EPA, lithium EPA, mono-, di- or triglyceride EPA or any other ester or salt of EPA, or the free acid form of EPA. The EPA may also be in the form of a 2-substituted derivative or other derivative which slows down its rate of oxidation but does not otherwise change its biological action to any substantial degree.

In another embodiment, EPA is present in a composition useful in accordance with methods of the invention in an amount of about 50 mg to about 5000 mg, about 75 mg to about 2500 mg, or about 100 mg to about 1000 mg, for example about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, 2525 mg, about 2550 mg, about 2575 mg, about 2600 mg, about 2625 mg, about 2650 mg, about 2675 mg, about 2700 mg, about 2725 mg, about 2750 mg, about 2775 mg, about 2800 mg, about 2825 mg, about 2850 mg, about 2875 mg, about 2900 mg, about 2925 mg, about 2950 mg, about 2975 mg, about 3000 mg, about 3025 mg, about 3050 mg, about 3075 mg, about 3100 mg, about 3125 mg, about 3150 mg, about 3175 mg, about 3200 mg, about 3225 mg, about 3250 mg, about 3275 mg, about 3300 mg, about 3325 mg, about 3350 mg, about 3375 mg, about 3400 mg, about 3425 mg, about 3450 mg, about 3475 mg, about 3500 mg, about 3525 mg, about 3550 mg, about 3575 mg, about 3600 mg, about 3625 mg, about 3650 mg, about 3675 mg, about 3700 mg, about 3725 mg, about 3750 mg, about 3775 mg, about 3800 mg, about 3825 mg, about 3850 mg, about 3875 mg, about 3900 mg, about 3925 mg, about 3950 mg, about 3975 mg, about 4000 mg, about 4025 mg, about 4050 mg, about 4075 mg, about 4100 mg, about 4125 mg, about 4150 mg, about 4175 mg, about 4200 mg, about 4225 mg, about 4250 mg, about 4275 mg, about 4300 mg, about 4325 mg, about 4350 mg, about 4375 mg, about 4400 mg, about 4425 mg, about 4450 mg, about 4475 mg, about 4500 mg, about 4525 mg, about 4550 mg, about 4575 mg, about 4600 mg, about 4625 mg, about 4650 mg, about 4675 mg, about 4700 mg, about 4725 mg, about 4750 mg, about 4775 mg, about 4800 mg, about 4825 mg, about 4850 mg, about 4875 mg, about 4900 mg, about 4925 mg, about 4950 mg, about 4975 mg, or about 5000 mg.

In another embodiment, a composition useful in accordance with the invention contains not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight, docosahexaenoic acid (DHA), if any. In another embodiment, a composition of the invention contains substantially no docosahexaenoic acid. In still another embodiment, a composition useful in the present invention contains no docosahexaenoic acid and/or derivative thereof.

In another embodiment, EPA comprises at least 70%, at least 80%, at least 90%, at least 95%, at least 96%, at least 97%, at least 98%, at least 99%, or 100%, by weight, of all fatty acids present in a composition that is useful in methods of the present invention.

In one embodiment, a composition of the invention comprises ultra-pure EPA. The term "ultra-pure" as used herein with respect to EPA refers to a composition comprising at least 95% by weight EPA (as the term "EPA" is defined and exemplified herein). Ultra-pure EPA comprises at least 96% by weight EPA, at least 97% by weight EPA, or at least 98% by weight EPA, wherein the EPA is any form of EPA as set forth herein.

In another embodiment, a composition useful in accordance with methods of the invention contains less than 10%, less than 9%, less than 8%, less than 7%, less than 6%, less than 5%, less than 4%, less than 3%, less than 2%, less than 1%, less than 0.5% or less than 0.25%, by weight of the total composition or by weight of the total fatty acid content, of any fatty acid other than EPA. Illustrative examples of a "fatty acid other than EPA" include linolenic acid (LA), arachidonic acid (AA), docosahexaenoic acid (DHA), alpha-linolenic acid (ALA), stearadonic acid (STA), eicosatrienoic acid (ETA) and/or docosapentaenoic acid (DPA). In another embodiment, a composition useful in accordance with methods of the invention contains about 0.1% to about 4%, about 0.5% to about 3%, or about 1% to about 2%, by weight, of total fatty acids other than EPA and/or DHA.

In another embodiment, a composition useful in accordance with the invention has one or more of the following features: (a) eicosapentaenoic acid ethyl ester represents at least about 96%, at least about 97%, or at least about 98%, by weight, of all fatty acids present in the composition; (b) the composition contains not more than about 4%, not more than about 3%, or not more than about 2%, by weight, of total fatty acids other than eicosapentaenoic acid ethyl ester; (c) the composition contains not more than about 0.6%, not more than about 0.5%, or not more than about 0.4% of any individual fatty acid other than eicosapentaenoic acid ethyl ester; (d) the composition has a refractive index (20° C.) of about 1 to about 2, about 1.2 to about 1.8 or about 1.4 to about 1.5; (e) the composition has a specific gravity (20° C.) of about 0.8 to about 1.0, about 0.85 to about 0.95 or about 0.9 to about 0.92; (e) the composition contains not more than about 20 ppm, not more than about 15 ppm or not more than about 10 ppm heavy metals, (f) the composition contains not more than about 5 ppm, not more than about 4 ppm, not more than about 3 ppm, or not more than about 2 ppm arsenic, and/or (g) the composition has a peroxide value of not more than about 5 meq/kg, not more than about 4 meq/kg, not more than about 3 meq/kg, or not more than about 2 meq/kg.

In another embodiment, a composition useful in accordance with the invention comprises, consists of or consists essentially of at least 95% by weight ethyl eicosapentaenoate (EPA-E), about 0.2% to about 0.5% by weight ethyl octadecatetraenoate (ODTA-E), about 0.05% to about 0.25% by weight ethyl nonaecapentaenoate (NDPA-E), about 0.2% to about 0.45% by weight ethyl arachidonate (AA-E), about 0.3% to about 0.5% by weight ethyl eicosatetraenoate (ETA-E), and about 0.05% to about 0.32% ethyl heneicosapentaenoate (HPA-E). In another embodiment, the composition is present in a capsule shell.

In another embodiment, compositions useful in accordance with the invention comprise, consist essential of, or consist of at least 95%, 96% or 97%, by weight, ethyl eicosapentaenoate, about 0.2% to about 0.5% by weight ethyl octadecatetraenoate, about 0.05% to about 0.25% by weight ethyl nonaecapentaenoate, about 0.2% to about 0.45% by weight ethyl arachidonate, about 0.3% to about 0.5% by weight ethyl eicosatetraenoate, and about 0.05% to about 0.32% ethyl heneicosapentaenoate. Optionally, the composition contains not more than about 0.06%, about 0.05%, or about 0.04%, by weight, DHA or derivative thereof such as ethyl-DHA. In one embodiment the composition contains substantially no or no amount of DHA or derivative thereof such as ethyl-DHA. The composition further optionally comprises one or more antioxidants (e.g. tocopherol) or other impurities in an amount of not more than about 0.5% or not more than 0.05%. In another embodiment, the composition comprises about 0.05% to about 0.4%, for example about 0.2% by weight tocopherol. In another embodiment, about 500 mg to about 1 g of the composition is provided in a capsule shell.

In another embodiment, compositions useful in accordance with the invention comprise, consist essential of, or consist of at least 96% by weight ethyl eicosapentaenoate, about 0.22% to about 0.4% by weight ethyl octadecatetraenoate, about 0.075% to about 0.20% by weight ethyl nonaecapentaenoate, about 0.25% to about 0.40% by weight ethyl arachidonate, about 0.3% to about 0.4% by weight ethyl eicosatetraenoate and about 0.075% to about 0.25% ethyl heneicosapentaenoate. Optionally, the composition contains not more than about 0.06%, about 0.05%, or about 0.04%, by weight, DHA or derivative thereof such as ethyl-DHA. In one embodiment the composition contains substantially no or no amount of DHA or derivative thereof such as ethyl-DHA. The composition further optionally comprises one or more antioxidants (e.g. tocopherol) or other impurities in an amount of not more than about 0.5% or not more than 0.05%. In another embodiment, the composition comprises about 0.05% to about 0.4%, for example about 0.2% by weight tocopherol. In another embodiment, the invention provides a dosage form comprising about 500 mg to about 1 g of the foregoing composition in a capsule shell. In one embodiment, the dosage form is a gel or liquid capsule and is packaged in blister packages of about 1 to about 20 capsules per sheet.

In another embodiment, compositions useful in accordance with the invention comprise, consist essential of, or consist of at least 96%, 97% or 98%, by weight, ethyl eicosapentaenoate, about 0.25% to about 0.38% by weight ethyl octadecatetraenoate, about 0.10% to about 0.15% by weight ethyl nonaecapentaenoate, about 0.25% to about 0.35% by weight ethyl arachidonate, about 0.31% to about 0.38% by weight ethyl eicosatetraenoate, and about 0.08% to about 0.20% ethyl heneicosapentaenoate. Optionally, the composition contains not more than about 0.06%, about 0.05%, or about 0.04%, by weight, DHA or derivative thereof such as ethyl-DHA. In one embodiment the composition contains substantially no or no amount of DHA or derivative thereof such as ethyl-DHA. The composition further optionally comprises one or more antioxidants (e.g. tocopherol) or other impurities in an amount of not more than about 0.5% or not more than 0.05%. In another embodiment, the composition comprises about 0.05% to about 0.4%, for example about 0.2% by weight tocopherol. In another embodiment, the invention provides a dosage form comprising about 500 mg to about 1 g of the foregoing composition in a capsule shell.

In another embodiment, a composition as described herein is administered to a subject once or twice per day. In another embodiment, 1, 2, 3 or 4 capsules, each containing about 1 g of a composition as described herein, are administered to a subject daily. In another embodiment, 1 or 2 capsules, each containing about 1 g of a composition as described herein, are administered to the subject in the morning, for example between about 5 am and about 11 am, and 1 or 2 capsules, each containing about 1 g of a composition as described herein, are administered to the subject in the evening, for example between about 5 pm and about 11 pm.

In one embodiment, a subject being treated in accordance with methods of the invention is not otherwise on lipid-altering therapy, for example statin, fibrate, niacin and/or ezetimibe therapy.

In another embodiment, compositions useful in accordance with methods of the invention are orally deliverable. The terms "orally deliverable" or "oral administration" herein include any form of delivery of a therapeutic agent or a composition thereof to a subject wherein the agent or composition is placed in the mouth of the subject, whether or not the agent or composition is swallowed. Thus "oral administration" includes buccal and sublingual as well as esophageal administration. In one embodiment, the composition is present in a capsule, for example a soft gelatin capsule.

A composition for use in accordance with the invention can be formulated as one or more dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (i.e. 1 to about 10, 1 to 8, 1 to 6, 1 to 4 or 1 to 2) of times per day, or as many times as needed to elicit a therapeutic response.

In another embodiment, the invention provides use of any composition described herein for treating moderate to severe hypertriglyceridemia in a subject in need thereof, comprising: providing a subject having a fasting baseline triglyceride level of about 500 mg/dl to about 1500 mg/dl and administering to the subject a pharmaceutical composition as described herein. In one embodiment, the composition comprises about 1 g to about 4 g of eicosapentaenoic acid ethyl ester, wherein the composition contains substantially no docosahexaenoic acid.

In one embodiment, compositions of the invention, upon storage in a closed container maintained at room temperature, refrigerated (e.g. about 5 to about 5-10° C.) temperature, or frozen for a period of about 1, 2, 3, 4, 5, 6, 7, 8, 9, 10, 11, or 12 months, exhibit at least about 90%, at least about 95%, at least about 97.5%, or at least about 99% of the active ingredient(s) originally present therein.

In one embodiment, the invention provides use of a composition as described herein in manufacture of a medicament for treatment of any of a cardiovascular-related disease. In another embodiment, the subject is diabetic.

In one embodiment, a composition as set forth herein is packaged together with instructions for using the composition to treat a cardiovascular disorder.

EXAMPLES

Example 1: Reduction of APOC3 Levels in Subjects with Baseline Fasting Triglyceride Levels of ≥500 mg/dl A multi-center, placebo-controlled randomized, double-blind, 12-week study with an open-label extension was performed to evaluate the efficacy and safety of AMR101 in patients with fasting triglyceride levels ≥500 mg/dL. The primary objective of the study was to determine the efficacy of AMR101 2 g daily and 4 g daily, compared to placebo, in lowering fasting TG levels in patients with fasting TG levels ≥500 mg/dL and ≤1500 mg/dL (≥5.65 mmol/L and ≤16.94 mmol/L).

The secondary objectives of this study were the following:
1. To determine the safety and tolerability of AMR101 2 g daily and 4 g daily;
2. To determine the effect of AMR101 on lipid and apolipoprotein profiles;
3. To determine the effect of AMR101 on low-density lipoprotein (LDL) particle number and size;
4. To determine the effect of AMR101 on oxidized LDL;
5. To determine the effect of AMR101 on fasting plasma glucose (FPG) and hemoglobin $A_{1c}$ (Hb$A_{1c}$);
6. To determine the effect of AMR101 on insulin resistance;
7. To determine the effect of AMR101 on high-sensitivity C-reactive protein (hsCRP);
8. To determine the effects of AMR101 2 g daily and 4 g daily on the incorporation of fatty acids into red blood cell membranes and into plasma phospholipids;
9. To explore the relationship between baseline fasting TG levels and the reduction in fasting TG levels; and
10. To explore the relationship between an increase in red blood cell membrane eicosapentaenoic acid (EPA) concentrations and the reduction in fasting TG levels.

The population for this study was men and women (women of childbearing potential needed to be on contraception or practice abstinence) >18 years of age with a body mass index ≤45 kg/m$^2$ who were not on lipid-altering therapy or were not currently on lipid-altering therapy. Patients currently on statin therapy (with or without ezetimibe) were evaluated by the investigator as to whether this therapy could be safely discontinued at screening, or if it should have been continued. If statin therapy (with or without ezetimibe) was to be continued, dose(s) must have been stable for ≥4 weeks prior to randomization. Patients taking non-statin, lipid-altering medications (niacin >200 mg/day, fibrates, fish oil, other products containing omega-3 fatty acids, or other herbal products or dietary supplements with potential lipid-altering effects), either alone or in combination with statin therapy (with or without ezetimibe), must have been able to safely discontinue non-statin, lipid-altering therapy at screening.

Approximately 240 patients were randomized at approximately 50 centers in North America, South America, Central America, Europe, India, and South Africa. The study was a 58- to 60-week, Phase 3, multi-center study consisting of 3 study periods: (1) a 6- to 8-week screening period that included a diet and lifestyle stabilization and washout period and a TG qualifying period; (2) a 12-week, double-blind, randomized, placebo-controlled treatment period; and (3) a 40-week, open-label, extension period.

During the screening period and double-blind treatment period, all visits were within ±3 days of the scheduled time. During the open-label extension period, all visits were within ±7 days of the scheduled time. The screening period included a 4- or 6-week diet and lifestyle stabilization period and washout period followed by a 2-week TG qualifying period.

The screening visit (Visit 1) occurred for all patients at either 6 weeks (for patients not on lipid-altering therapy at screening or for patients who did not need to discontinue their current lipid-altering therapy) or 8 weeks (for patients who required washout of their current lipid-altering therapy at screening) before randomization, as follows:

Patients who did not require a washout: The screening visit will occur at Visit 1 (Week −6). Eligible patients entered a 4-week diet and lifestyle stabilization period. At the screening visit, all patients received counseling regarding the importance of the National Cholesterol Education Program (NCEP) Therapeutic Lifestyle Changes (TLC) diet and received instructions on how to follow this diet. Patients who required a washout: The screening visit occurred at Visit 1 (Week −8). Eligible patients began a 6-week washout period at the screening visit. Patients received counseling regarding the NCEP TLC diet and received instructions on how to follow this diet. Site personnel contacted patients who did not qualify for participation based on screening laboratory test results to instruct them to resume their prior lipid-altering medications.

At the end of the 4-week diet and lifestyle stabilization period or the 6-week diet and stabilization and washout period, eligible patients entered the 2-week TG qualifying period and had their fasting TG level measured at Visit 2 (Week −2) and Visit 3 (Week −1). Eligible patients must have had an average fasting TG level ≥500 mg/dL and ≤1500 mg/dL (≥5.65 mmol/L and ≤16.94 mmol/L) to enter the 12-week double-blind treatment period. The TG level for qualification was based on the average (arithmetic mean) of the Visit 2 (Week −2) and Visit 3 (Week −1) values. If a patient's average TG level from Visit 2 and Visit 3 fell outside the required range for entry into the study, an additional sample for fasting TG measurement was collected 1 week later at Visit 3.1. If a third sample was collected at Visit 3.1, entry into the study was based on the average (arithmetic mean) of the values from Visit 3 and Visit 3.1.

After confirmation of qualifying fasting TG values, eligible patients entered a 12-week, randomized, double-blind treatment period. At Visit 4 (Week 0), patients were randomly assigned to one of the following treatment groups:
AMR101 2 g daily,
AMR101 4 g daily, or
Placebo.

During the double-blind treatment period, patients returned to the site at Visit 5 (Week 4), Visit 6 (Week 11), and Visit 7 (Week 12) for efficacy and safety evaluations.

Patients who completed the 12-week double-blind treatment period were eligible to enter a 40-week, open-label, extension period at Visit 7 (Week 12). All patients received open-label AMR101 4 g daily. From Visit 8 (Week 16) until the end of the study, changes to the lipid-altering regimen were permitted (e.g., initiating or raising the dose of statin or adding non-statin, lipid-altering medications to the regimen), as guided by standard practice and prescribing information. After Visit 8 (Week 16), patients returned to the site every 12 weeks until the last visit at Visit 11 (Week 52).

Eligible patients were randomly assigned at Visit 4 (Week 0) to orally receive AMR101 2 g daily, AMR101 4 g daily, or placebo for the 12-week double-blind treatment period. AMR101 was provided in 1 g liquid-filled, oblong, gelatin capsules. The matching placebo capsule was filled with light liquid paraffin and contained 0 g of AMR101. During the double-blind treatment period, patients took 2 capsules (AMR101 or matching placebo) in the morning and 2 in the evening for a total of 4 capsules per day. Patients in the AMR101 2 g/day treatment group received 1 AMR101 1 g capsule and 1 matching placebo capsule in the morning and in the evening. Patients in the AMR101 4 g/day treatment group received 2 AMR101 1 g capsules in the morning and evening.

Patients in the placebo group received 2 matching placebo capsules in the morning and evening. During the extension period, patients received open-label AMR101 4 g daily. Patients took 2 AMR101 1 g capsules in the morning and 2 in the evening.

The primary efficacy variable for the double-blind treatment period was percent change in TG from baseline to Week 12 endpoint. The secondary efficacy variables for the double-blind treatment period included the following:

Percent changes in total cholesterol (TC), high-density lipoprotein cholesterol (HDL-C), calculated low-density lipoprotein cholesterol (LDL-C), calculated non-high-density lipoprotein cholesterol (non-HDL-C), and very low-density lipoprotein cholesterol (VLDL-C) from baseline to Week 12 endpoint;

Percent change in very low-density lipoprotein TG from baseline to Week 12;

Percent changes in apolipoprotein A-I (apo A-I), apolipoprotein B (apo B), and apo A-I/apo B ratio from baseline to Week 12;

Percent changes in lipoprotein (a) from baseline to Week 12 (selected sites only);

Percent changes in LDL particle number and size, measured by nuclear magnetic resonance, from baseline to Week 12 (selected sites only);

Percent change in remnant-like particle cholesterol from baseline to Week 12 (selected sites only);

Percent change in oxidized LDL from baseline to Week 12 (selected sites only);

Changes in FPG and $HbA_{1c}$ from baseline to Week 12;

Change in insulin resistance, as assessed by the homeostasis model index insulin resistance, from baseline to Week 12;

Percent change in lipoprotein associated phospholipase A2 from baseline to Week 12 (selected sites only);

Change in intracellular adhesion molecule-1 from baseline to Week 12 (selected sites only);

Change in interleukin-6 from baseline to Week 12 (selected sites only);

Change in plasminogen activator inhibitor-1 from baseline to Week 12 (selected sites only);

Change in hsCRP from baseline to Week 12 (selected sites only);

Change in serum phospholipid EPA content from baseline to Week 12;

Change in red blood cell membrane EPA content from baseline to Week 12; and

Change in serum phospholipid and red blood cell membrane content in the following fatty acids from baseline to Week 12: docosapentaenoic acid, docosahexaenoic acid, arachidonic acid, palmitic acid, stearic acid, and oleic acid.

The efficacy variable for the open-label extension period was percent change in fasting TG from extension baseline to end of treatment. Safety assessments included adverse events, clinical laboratory measurements (chemistry, hematology, and urinalysis), 12-lead electrocardiograms (ECGs), vital signs, and physical examinations For TG, TC, HDL-C, calculated LDL-C, calculated non-HDL-C, and VLDL-C, baseline was defined as the average of Visit 4 (Week 0) and the preceding lipid qualifying visit (either Visit 3 [Week −1] or if it occurs, Visit 3.1) measurements. Baseline for all other efficacy parameters was the Visit 4 (Week 0) measurement.

For TC, HDL-C, calculated LDL-C, calculated non-HDL-C, and VLDL-C, Week 12 endpoint was defined as the average of Visit 6 (Week 11) and Visit 7 (Week 12) measurements. Week 12 endpoint for all other efficacy parameters was the Visit 7 (Week 12) measurement.

The primary efficacy analysis was performed using a 2-way analysis of covariance (ANCOVA) model with treatment as a factor and baseline TG value as a covariate. The least-squares mean, standard error, and 2-tailed 95% confidence interval for each treatment group and for each comparison was estimated. The same 2-way ANCOVA model was used for the analysis of secondary efficacy variables.

The primary analysis was repeated for the per-protocol population to confirm the robustness of the results for the intent-to-treat population.

The primary efficacy variable was the percent change in fasting TG levels from baseline to Week 12. A sample size of 69 completed patients per treatment group was expected to provide ≥90% power to detect a difference of 30% between AMR101 and placebo in percent change from baseline in fasting TG levels, assuming a standard deviation of 45% in TG measurements and a significance level of p<0.01. To accommodate a 15% drop-out rate from randomization to completion of the double-blind treatment period, a total of 240 randomized patients was planned (80 patients per treatment group).

As shown in Table 1 and corresponding FIG. 1, subjects in the 2 g/day treatment population exhibited a non-significant increase in total ApoC3 compared to baseline (+0.3%), and a 14.3% reduction compared to placebo (p=0.0154); a non-significant increase in HDL-ApoC3 compared to baseline (+0.3%) and a 5.9% reduction compared to placebo (p=0.4062); and a 1.4% increase in non-HDL-ApoC3 compared to baseline and a 22.5% reduction compared to placebo (p=0.0142). Subjects in the 4 g/day treatment group exhibited reductions in total ApoC3 (10.1%), HDL-ApoC3 (21.4%) and non-HDL-ApoC3 (5.4%) compared to baseline, which correspond to statistically significant median placebo-adjusted reductions in total ApoC3 (25.1%, p<0.0001), HDL-ApoC3 (23.3%, p=0.002) and non-HDL-ApoC3 (31.8%, p=0.0002).

Figure 2:
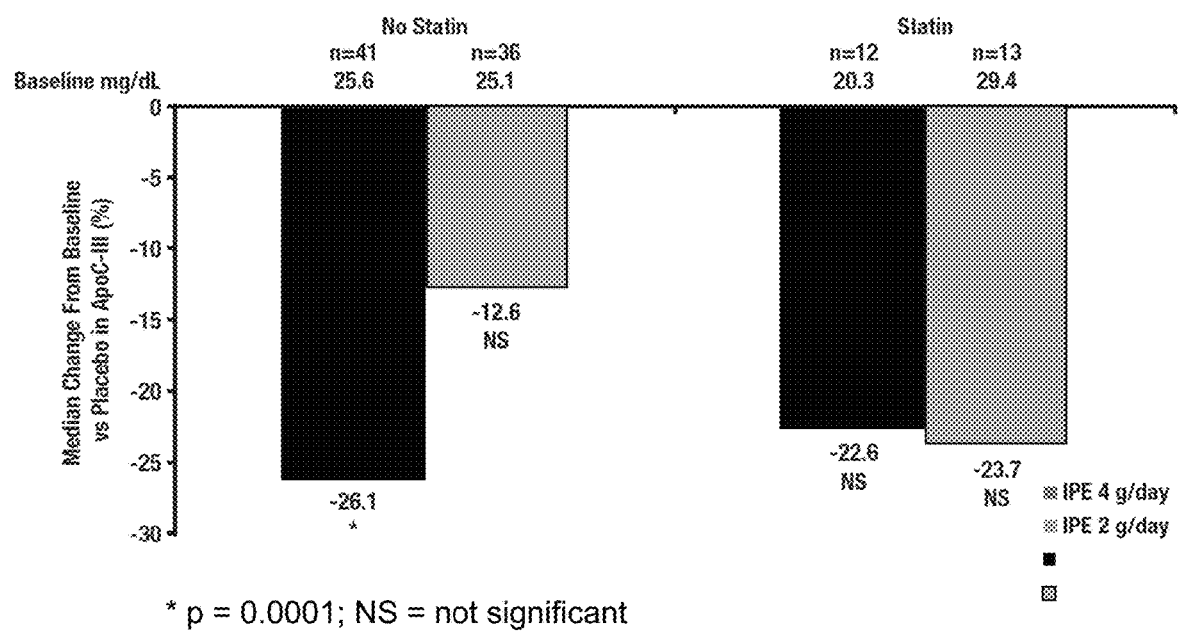
FIG. 2 depicts reductions in total apolipoprotein C-III in patients having fasting triglyceride levels ≥500 mg/dL after being administered 2 g/day or 4 g/day of a composition according to the present disclosure (AMR101).

As shown in Table 2 and corresponding FIG. 2, subjects in the 2 g/day group who did not receive a statin experienced a 12.6% non-significant reduction in ApoC3 levels compared to placebo after 12 weeks. Subjects in the 2 g/day group who also received a statin experienced a 23.7% non-significant decrease in ApoC3 compared to placebo. Subjects in the 4 g/day group who also received a statin experienced a 22.6% non-significant decrease in ApoC3 compared to placebo, while those not receiving a statin experienced a 26.1% significant (p=0.0001) decrease in ApoC3 compared to placebo.

Example 2: Reduction of APOC3 Levels in Subjects with Baseline Fasting Triglyceride Levels of 200 mg/dl to 500 mg/dl A multi-center, placebo-controlled, randomized, double-blind, 12-week study was performed to evaluate the efficacy and safety of >96% E-EPA in patients with fasting triglyceride levels ≥200 mg/dl and <500 mg/dl despite statin therapy (the mean of two qualifying entry values needed to be ≥185 mg/dl and at least one of the values needed to be ≥200 mg/dl). The primary objective of the study was to determine the efficacy of >96% E-EPA 2 g daily and 4 g daily, compared to placebo, in lowering fasting TG levels in patients with high risk for cardiovascular disease and with fasting TG levels ≥200 mg/dl and <500 mg/dl, despite treatment to LDL-C goal on statin therapy.

The secondary objectives of this study were the following:
1. To determine the safety and tolerability of >96% E-EPA 2 g daily and 4 g daily;
2. To determine the effect of >96% E-EPA on lipid and apolipoprotein profiles including total cholesterol (TC), non-high-density lipoprotein cholesterol (non-HDL-C), low density lipoprotein cholesterol (LDL-C), high density lipoprotein cholesterol (HDL-C), and very high density lipoprotein cholesterol (VHDL-C);
3. To determine the effect of >96% E-EPA on lipoprotein associated phospholipase $A_2$ (Lp-$PLA_2$) from baseline to week 12;
4. To determine the effect of >96% E-EPA on low-density lipoprotein (LDL) particle number and size;
5. To determine the effect of >96% E-EPA on oxidized LDL;
6. To determine the effect of >96% E-EPA on fasting plasma glucose (FPG) and hemoglobin $A_{1c}$ (Hb$A_{1c}$);
7. To determine the effect of >96% E-EPA on insulin resistance;
8. To determine the effect of >96% E-EPA on high-sensitivity C-reactive protein (hsCRP);
9. To determine the effects of >96% E-EPA 2 g daily and 4 g daily on the incorporation of fatty acids into red blood cell membranes and into plasma phospholipids;
10. To explore the relationship between baseline fasting TG levels and the reduction in fasting TG levels; and
11. To explore the relationship between changes of fatty acid concentrations in plasma and red blood cell membranes, and the reduction in fasting TG levels.

The population for this study was men and women >18 years of age with a body mass index ≤45 kg/m² with fasting TG levels greater than or equal to 200 mg/dl and less than 500 mg/dl and on a stable does of statin therapy (with or without ezetimibe). The statin was atorvostatin, rosuvastatin or simvastatin. The dose of statin must have been stable for ≥4 weeks prior to the LDL-C/TG baseline qualifying measurement for randomization. The statin dose was optimized such that the patients are at their LDL-C goal at the LDL-C/TG baseline qualifying measurements. The same statin at the same dose was continued until the study ended.

Patients taking any additional non-statin, lipid-altering medications (niacin >200 mg/day, fibrates, fish oil, other products containing omega-3 fatty acids, or other herbal products or dietary supplements with potential lipid-altering effects), either alone or in combination with statin therapy (with or without ezetimibe), must have been able to safely discontinue non-statin, lipid-altering therapy at screening.

Patients at high risk for CVD, i.e., patients with clinical coronary heart disease (CHD) or clinical CHD risk equivalents (10-year risk >20%) as defined in the National Cholesterol Education Program (NCEP) Adult Treatment Panel III (ATP III) Guidelines were eligible to participate in this study. Those included patients with any of the following criteria: (1) Known CVD, either clinical coronary heart disease (CHD), symptomatic carotid artery disease (CAD), peripheral artery disease (PAD) or abdominal aortic aneurism; or (2) Diabetes Mellitus (Type 1 or 2).

Approximately 702 patients were randomized at approximately 80 centers in the U.S. The study was a 18- to 20-week, Phase 3, multi-center study consisting of 2 study periods: (1) A 6- to 8-week screening period that included a diet and lifestyle stabilization, a non-statin lipid-altering treatment washout, and an LDL-C and TG qualifying period and (2) A 12-week, double-blind, randomized, placebo-controlled treatment period.

During the screening period and double-blind treatment period, all visits were within ±3 days of the scheduled time. All patients continued to take the statin product (with or without ezetimibe) at the same dose they were taking at screening throughout their participation in the study.

The 6- to 8-week screening period included a diet and lifestyle stabilization, a non-statin lipid-altering treatment washout, and an LDL-C and TG qualifying period. The screening visit (Visit 1) occurred for all patients at either 6 weeks (for patients on stable statin therapy [with or without ezetimibe] at screening) or 8 weeks (for patients who will require washout of their current non-statin lipid-altering therapy at screening) before randomization, as follows:

Patients who did not require a washout: The screening visit occurred at Visit 1 (Week −6). Eligible patients entered a 4-week diet and lifestyle stabilization period. At the screening visit, all patients received counseling regarding the importance of the National Cholesterol Education Program (NCEP) Therapeutic Lifestyle Changes (TLC) diet and received basic instructions on how to follow this diet.

Patients who required a washout: The screening visit occurred at Visit 1 (Week −8). Eligible patients began a 6-week washout period at the screening visit (i.e. 6 weeks washout before the first LDL-C/TG qualifying visit). Patients received counseling regarding the NCEP TLC diet and received basic instructions on how to follow this diet. Site personnel contacted patients who did not qualify for participation based on screening laboratory test results to instruct them to resume their prior lipid-altering medications.

At the end of the 4-week diet and lifestyle stabilization period or the 6-week diet and stabilization and washout period, eligible patients entered the 2-week LDL-C and TG qualifying period and had their fasting LDL-C and TG levels measured at Visit 2 (Week −2) and Visit 3 (Week −1). Eligible patients must have had an average fasting LDL-C level ≥40 mg/dL and <100 mg/dL and an average fasting TG level ≥200 mg/dL and <500 mg/dL to enter the 12-week double-blind treatment period. The LDL-C and TG levels for qualification were based on the average (arithmetic mean) of the Visit 2 (Week −2) and Visit 3 (Week −1) values. If a patient's average LDL-C and/or TG levels from Visit 2 and Visit 3 fell outside the required range for entry into the study, an additional fasting lipid profile was collected 1 week later at Visit 3.1. If a third sample was collected at Visit 3.1, entry into the study was based on the average (arithmetic mean) of the values from Visit 3 and Visit 3.1.

After confirmation of qualifying fasting LDL-C and TG values, eligible patients entered a 12-week, randomized, double-blind treatment period. At Visit 4 (Week 0), patients were randomly assigned to 1 of the following treatment groups:

>96% E-EPA 2 g daily,
>96% E-EPA 4 g daily, or
Placebo.

226 to 234 patients per treatment group were randomized in this study. Stratification was by type of statin (atorvastatin, rosuvastatin or simvastatin), the presence of diabetes, and gender.

During the double-blind treatment period, patients returned to the site at Visit 5 (Week 4), Visit 6 (Week 11), and Visit 7 (Week 12) for efficacy and safety evaluations.

Eligible patients were randomly assigned at Visit 4 (Week 0) to receive orally >96% E-EPA 2 g daily, >96% E-EPA 4 g daily, or placebo.

>96% E-EPA was provided in 1 g liquid-filled, oblong, gelatin capsules. The matching placebo capsule was filled with light liquid paraffin and contained 0 g of >96% E-EPA. >96% E-EPA capsules were to be taken with food (i.e. with or at the end of a meal).

During the double-blind treatment period, patients were to take 2 capsules (>96% E-EPA or matching placebo) in the morning and 2 capsules in the evening for a total of 4 capsules per day.

Patients in the >96% E-EPA 2 g/day treatment group received 1>96% E-EPA 1 g capsule and 1 matching placebo capsule in the morning and in the evening.

Patients in the >96% E-EPA 4 g/day treatment group received 2>96% E-EPA 1 g capsules in the morning and evening.

Patients in the placebo group received 2 matching placebo capsules in the morning and evening.

The primary efficacy variable for the double-blind treatment period was percent change in TG from baseline to Week 12 endpoint. The secondary efficacy variables for the double-blind treatment period included the following:

Percent changes in total cholesterol (TC), high-density lipoprotein cholesterol (HDL-C), LDL-C, calculated non-HDL-C, and very low-density lipoprotein cholesterol (VLDL-C) from baseline to Week 12 endpoint;

Percent change in very low-density lipoprotein TG from baseline to Week 12;

Percent changes in apolipoprotein A-I (apo A-I), apolipoprotein B (apo B), and apo A-I/apo B ratio from baseline to Week 12;

Percent changes in lipoprotein(a) from baseline to Week 12;

Percent changes in LDL particle number and size, measured by nuclear magnetic resonance, from baseline to Week 12;

Percent change in remnant-like particle cholesterol from baseline to Week 12;

Percent change in oxidized LDL from baseline to Week 12;

Changes in FPG and $HbA_{1c}$ from baseline to Week 12;

Change in insulin resistance, as assessed by the homeostasis model index insulin resistance, from baseline to Week 12;

Percent change in lipoprotein associated phospholipase $A_2$ ($Lp$-$PLA_2$) from baseline to Week 12;

Change in intracellular adhesion molecule-1 from baseline to Week 12;

Change in interleukin-2 from baseline to Week 12;

Change in plasminogen activator inhibitor-1 from baseline to Week 12. Note: this parameter will only be collected at sites with proper storage conditions;

Change in hsCRP from baseline to Week 12; and

Change in plasma concentration and red blood cell membrane content of fatty acid from baseline to Week 12 including EPA, docosapentaenoic acid (DPA), docosahexaenoic acid (DHA), arachidonic acid (AA), dihomo-γ-linolenic acid (DGLA), the ratio of EPA/AA, ratio of oleic acid/stearic acid (OA/SA), and the ratio of total omega-3 acids over total omega-6 acids.

Safety assessments included adverse events, clinical laboratory measurements (chemistry, hematology, and urinalysis), 12-lead electrocardiograms (ECGs), vital signs, and physical examinations.

For TG, TC, HDL-C, LDL-C, calculated non-HDL-C, and VLDL-C, baseline was defined as the average of Visit 4 (Week 0) and the preceding lipid qualifying visit (either Visit 3 [Week −1] or if it occurs, Visit 3.1) measurements. Baseline for all other efficacy parameters was the Visit 4 (Week 0) measurement.

For TG, TC, HDL-C, LDL-C, calculated non-HDL-C, and VLDL-C, Week 12 endpoint was defined as the average of Visit 6 (Week 11) and Visit 7 (Week 12) measurements.

Week 12 endpoint for all other efficacy parameters were the Visit 7 (Week 12) measurement.

The primary efficacy analysis was performed using a 2-way analysis of covariance (ANCOVA) model with treatment as a factor and baseline TG value as a covariate. The least-squares mean, standard error, and 2-tailed 95% confidence interval for each treatment group and for each comparison were estimated. The same 2-way ANCOVA model was used for the analysis of secondary efficacy variables.

The primary analysis was repeated for the per-protocol population to confirm the robustness of the results for the intent-to-treat population.

Non-inferiority tests for percent change from baseline in LDL-C were performed between >96% E-EPA doses and placebo using a non-inferiority margin of 6% and a significant level at 0.05.

For the following key secondary efficacy parameters, treatment groups were compared using Dunnett's test to control the Type 1 error rate: TC, LDL-C, HDL-C, non-HDL-C, VLDL-C, Lp-PLA$_2$, and apo B. For the remaining secondary efficacy parameters, Dunnett's test was be used and the ANCOVA output were considered descriptive.

The evaluation of safety was based primarily on the frequency of adverse events, clinical laboratory assessments, vital signs, and 12-lead ECGs. The primary efficacy variable is the percent change in fasting TG levels from baseline to Week 12. A sample size of 194 completed patients per treatment group provided 90.6% power to detect a difference of 15% between >96% E-EPA and placebo in percent change from baseline in fasting TG levels, assuming a standard deviation of 45% in TG measurements and a significance level of p<0.05.

Previous data on fasting LDL-C show a difference in percent change from baseline of 2.2%, with a standard deviation of 15%, between study drug and placebo. A sample size of 194 completed patients per treatment group provided 80% power to demonstrate non-inferiority (p<0.05, one-sided) of the LDL-C response between >96% E-EPA 4 g daily and placebo, within a 6% margin. To accommodate a 10% drop-out rate from randomization to completion of the double-blind treatment period, a total of 648 randomized patients was planned (216 patients per treatment group); 702 subjects were randomized, as further described below.

Results

Of the 702 randomized subjects, 687 were in the intent-to-treat ("ITT") population as follows:
Ultra-pure EPA, 4 g/day: 226 subjects
Ultra-pure EPA, 2 g/day: 234 subjects
Placebo: 227 subjects Lipids were extracted from plasma and red blood cell ("RBC") suspensions and converted into fatty acid methyl esters for analysis using a standard validated gas chromatography/flame ionization detection method. Fatty acid parameters were compared between EPA treatment groups and placebo using an ANCOVA model with treatment, gender, type of statin therapy, and presence of diabetes as factors, and the baseline parameter value as a covariate. LSMs, SEs, and 2-tailed 95% confidence intervals for each treatment group and for each comparison were determined.

Baseline characteristics of the three ITT groups were comparable, with 61.4% of the ITT subjects being male, 96.3% being white, having a mean age of 61.4 years, a weight of 95.7 kg and a BMI of 32.9 kg/m$^2$. ITT subjects with incomplete fatty acid data at baseline and/or at 12 weeks were excluded from the analyses.

As shown in Table 3 and corresponding FIG. 1, subjects in the 2 g/day treatment population exhibited a decrease in total ApoC3 compared to baseline (−0.6%), and an 8.5% reduction compared to placebo (p=0.0008). Subjects in the 4 g/day treatment group exhibited reductions in total ApoC3 (9.4%) compared to baseline, which corresponds to a statistically significant median placebo-adjusted reduction in total ApoC3 of 19.2% (p<0.0001).

Figure 3:
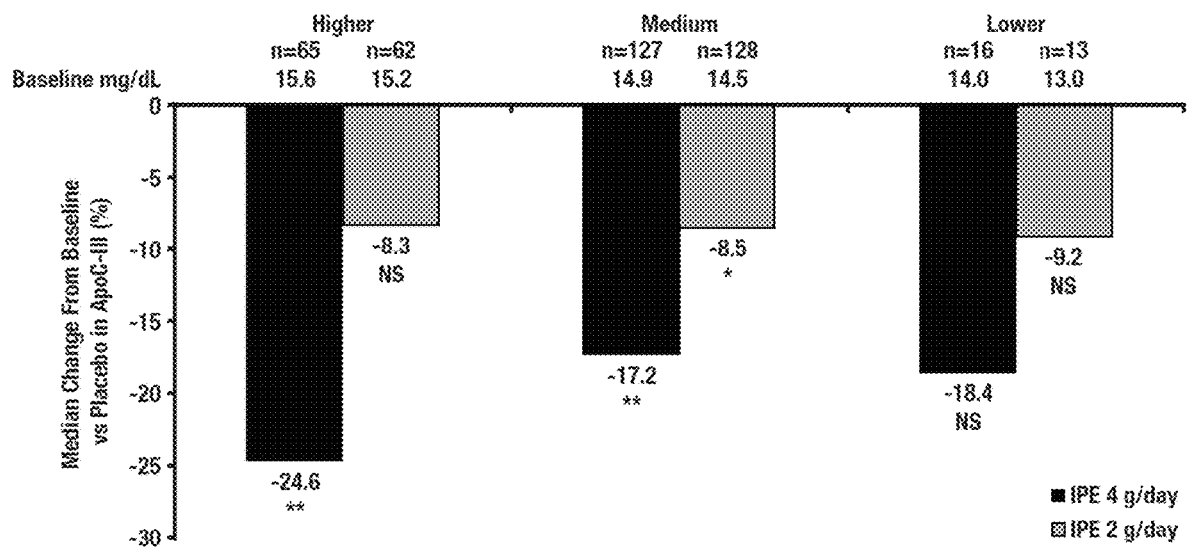
FIG. 3 depicts reductions in total apolipoprotein C-III in patients having fasting triglyceride levels of 200-499 mg/dL as a function of statin efficacy level after being administered 2 g/day or 4 g/day of a composition according to the present disclosure (AMR101).

As shown in Table 4 and corresponding FIG. 3, subjects in the 2 g/day treatment population exhibited non-significant decreases in ApoC3 compared to placebo when also on a higher-efficacy or lower-efficacy statin regimen (−8.3%, p=0.0862; −9.2%, p=0.7524, respectively), while subjects on a medium efficacy statin regimen exhibited a significant 8.5% reduction in ApoC3 compared to placebo (p=0.0038). Subjects in the 4 g/day treatment population exhibited significant reductions in ApoC3 levels compared to placebo when on higher-efficacy or medium efficacy statin regimens (−24.6%, p<0.0001; −17.2%, p<0.0001, respectively), while subjects in the 4 g/day group on a lower-efficacy statin regimen exhibited a non-significant 18.4% reduction in ApoC3 compared to placebo.

Example 3: Determination of APOC3 in Serum or Plasma

Apolipoprotein C3 levels can be determined in serum or plasma by an in vitro immunoturbidimetric immunoassay as follows.

A blood sample is centrifuged and the serum (plasma) separated. An 8 µL aliquot of the serum is combined with 300 µL of a buffer solution (e.g., a 100 mmol/L 2-amino-2-hydroxymethyl-1,3-propanediol buffer at pH 8.5). After stabilizing at 37° C. for about 5 minutes, the difference in absorbance at 800 nm and 340 nm is determined by a suitable analyzer (e.g., a Hitachi 7150 series Automatic Analyzer). A 100 µL aliquot of a 10 U/mL anti-human apolipoprotein C3 goat-polyclonal antibody is then added, and the difference in absorbance at 800 nm and 340 nm is determined after stabilization for about 5 minutes at 37° C. Comparison of the absorbance to a calibration curve derived from samples of known ApoC3 concentration allows calculation of the ApoC3 concentration in the blood sample.

TABLE 1

Reductions in ApoC3, HDL-ApoC3 and non-HDL-ApoC3

| | Placebo (N = 75) | | | AMR101 2 g/day (N = 73) | | | AMR101 4 g/day (N = 76) | | | Median (%)/p-value | |
|---|---|---|---|---|---|---|---|---|---|---|---|
| | Baseline value (IQR) | End-of-treatment value (IQR) | Change from baseline % (IQR) | Baseline value (IQR) | End-of-treatment value (IQR) | Change from baseline % (IQR) | Baseline value (IQR) | End-of-treatment value (IQR) | Change from baseline % (IQR) | AMR101 4 g/day vs placebo | AMR101 2 g/day vs placebo |
| Total ApoC3 (mg/dL) N = 46, 49, 53 | 26.8 (17.3) | 32.7 (14.6) | 12.3% (41.5) | 25.9 (11.1) | 28.4 (12.0) | 0.3% (29.9) | 25.6 (11.6) | 19.7 (10.5) | −10.1% (27.1) | −25.1% <0.0001 | −14.3% 0.0154 |
| HDL-ApoC3 (mg/dL) N = 39, 46, 47 | 14.3 (8.0) | 15.8 (7.4) | 2.9% (41.0) | 14.7 (6.1) | 15.6 (8.0) | 0.3% (29.3) | 12.6 (5.4) | 10.5 (4.1) | −21.4% (26.9) | −23.3% 0.002 | −5.9% 0.4062 |
| Non-HDL-ApoC3 (mg/dL) N = 39, 46, 47 | 11.0 (6.6) | 12.6 (10.2) | 22.4% (68.3) | 10.9 (5.5) | 10.2 (5.1) | 1.4% (36.9) | 9.3 (5.34) | 9.3 (4.2) | −5.4% (29.4) | −31.8% 0.0002 | −22.5% 0.0142 |

IQR = interquartile range.
ApoC3 concentrations were measured using an in vitro immunoturbidimetric immunoassay.
Median values and interquartile ranges (IQR) are reported for all endpoint values.
Baseline is defined as Visit 4 (Week 0).
The end-of-treatment value is from Visit 7 (Week 12).
P-values are from the Wilcoxon rank-sum test.

TABLE 2

Reductions in ApoC3 in Subjets Having Baseline Tryglycerides of ≥500 mg/dL

| | Placebo (N = 75) | | | AMR101 2 g/day (N = 73) | | | AMR101 4 g/day (N = 76) | | | Median (%)/p-value | |
|---|---|---|---|---|---|---|---|---|---|---|---|
| | Baseline value (IQR) | End-of-treatment Value (IQR) | Change from baseline % (IQR) | Baseline value (IQR) | End-of-treatment value (IQR) | Change from baseline % (IQR) | Baseline value (IQR) | End-of-treatment value (IQR) | Change from baseline % (IQR) | AMR101 4 g/day vs placebo | AMR101 2 g/day vs placebo |
| No Statin | 26.1 (16.5) | 30.5 (16.4) | 12.6 (41.5) | 25.1 (11.4) | 23.5 (12.0) | 1.3 (29.3) | 25.6 (11.5) | 19.7 (9.1) | −11.6 (27.0) | −26.1 0.0001 | −12.6 0.0543 |
| With Statin | 38.7 (13.5) | 42.3 (21.1) | 9.3 (68.9) | 29.4 (10.8) | 28.9 (4.6) | −6.7 (33.2) | 20.3 (12.9) | 18.9 (12.5) | −7.9 (28.1) | −22.6 0.0832 | −23.7 0.0961 |

IQR = interquartile range.
ApoC3 concentrations were measured using an in vitro immunoturbidimetric immunoassay.
Median values and interquartile ranges (IQR) are reported for all endpoint values.
Baseline is defined as Visit 4 (Week 0).
The end-of-treatment value is from Visit 7 (Week 12).
P-values are from the Wilcoxon rank-sum test.

TABLE 3

Reductions in ApoC3, HDL-ApoC3 and non-HDL-ApoC3

| | Placebo (N = 227) | | | AMR101 2 g/day (N = 234) | | | AMR101 4 g/day (N = 226) | | | Median (%)/p-value | |
|---|---|---|---|---|---|---|---|---|---|---|---|
| | Baseline value (IQR) | End-of-treatment Value (IQR) | Change from baseline % (IQR) | Baseline value (IQR) | End-of-treatment value (IQR) | Change from baseline % (IQR) | Baseline value (IQR) | End-of-treatment value (IQR) | Change from baseline % (IQR) | AMR101 4 g/day vs placebo | AMR101 2 g/day vs placebo |
| Total ApoC3 (mg/dL) N = 201, 203, 208 | 14.8 (4.5) | 16.2 (5.6) | 10.9% (30.0) | 14.8 (4.2) | 14.8 (5.0) | −0.6% (30.5) | 15.2 (4.8) | 13.7 (4.8) | −9.4% (25.9) | −19.2% <0.0001 | −8.5% 0.0008 |

IQR = interquartile range.
ApoC3 concentrations were measured using an in vitro immunoturbidimetric immunoassay.
Median values and interquartile ranges (IQR) are reported for all endpoint values.
Baseline is defined as Visit 4 (Week 0).
The end-of-treatment value is from Visit 7 (Week 12).
P-values are from the Wilcoxon rank-sum test.

TABLE 4

Reductions in ApoC3 in Subjets Having Baseline Tryglecerides of 200-499 mg/dL and on Statin Therapy

| | Placebo (N = 75) | | | AMR101 2 g/day (N = 73) | | | AMR101 4 g/day (N = 76) | | | Median (%)/p-value | |
|---|---|---|---|---|---|---|---|---|---|---|---|
| | Baseline value (IQR) | End-of-treatment Value (IQR) | Change from baseline % (IQR) | Baseline value (IQR) | End-of-treatment value (IQR) | Change from baseline % (IQR) | Baseline value (IQR) | End-of-treatment value (IQR) | Change from baseline % (IQR) | AMR101 4 g/day vs placebo | AMR101 2 g/day vs placebo |
| Higher Efficacy Statin Regimen | 15.2 (4.3) | 16.2 (6.5) | 16.2 (6.5) | 15.2 (4.4) | 15.5 (6.4) | −0.3 (34.8) | 15.6 (4.4) | 14.3 (5.0) | −13.9 (25.1) | −24.6 <0.0001 | −8.3 0.0862 |
| Medium Efficacy Statin Regimen | 14.7 (4.5) | 16.2 (5.6) | 10.6 (25.9) | 14.5 (4.3) | 14.6 (4.8) | −0.9 (27.8) | 14.9 (4.9) | 13.4 (4.6) | −7.3 (25.3) | −17.2 <0.0001 | −8.5 0.0038 |
| Lower Efficacy Statin Regimen | 15.3 (8.5) | 16.2 (4.0) | 16.9 (58.3) | 13.0 (2.6) | 13.1 (2.3) | 0.4 (30.3) | 14.0 (4.1) | 13.4 (3.7) | 0.2 (26.8) | −18.4 0.2891 | −9.2 0.7524 |

Higher Statin Efficacy Regimen means rosuvastatin 20 to 40 mg, atorvastatin 40 to 80 mg, simvastatin 80 mg, or simvastatin 40 to 80 mg plus ezetimibe 5 to 10 mg.
Medium Statin Efficacy Regimen means rosuvastatin 5 to 10 mg, atorvastatin 10 to 20 mg, simvastatin 20 to 40 mg, or simvastatin 10 to 20 mg plus ezetimibe 5 to 10 mg.
Lower Efficacy Statin Regimen means simvastatin 5 to 10 mg.
IQR = interquartile range.
ApoC3 concentrations were measured using an in vitro immunoturbidimetric immunoassay.
Median values and interquartile ranges (IQR) are reported for all endpoint values.
Baseline is defined as Visit 4 (Week 0).
The end-of-treatment value is from Visit 7 (Week 12).
P-values are from the Wilcoxon rank-sum test.

What is claimed is:

1. A method of reducing an apolipoprotein C-III (APOC3) level of a subject on statin therapy and having baseline fasting triglycerides of about 200 mg/dl to about 499 mg/dl, the method comprising administering to the subject a pharmaceutical composition comprising about 1 g to about 4 g of ethyl eicosapentaenoate per day,
   wherein the subject is on a high statin efficacy regimen selected from the group consisting of about 20 to about 40 mg rosuvastatin, about 40 to about 80 mg atorvastatin, about 80 mg simvastatin, and about 40 to about 80 mg simvastatin plus about 5 to about 10 mg ezetimibe or the subject is on a medium statin efficacy regimen selected from the group consisting of about 5 to about 10 mg rosuvastatin, about 10 to about 20 mg atorvastatin, about 20 to about 40 mg simvastatin, and about 10 to about 20 mg simvastatin plus about 5 to about 10 mg ezetimibe.

2. The method of claim 1, wherein the APOC3 level is reduced by at least about 5%.

3. The method of claim 1, wherein the APOC3 level is reduced by at least about 15%.

4. The method of claim 1, wherein about 2 g per day of ethyl eicosapentaenoate is administered to the subject.

5. The method of claim 1, wherein about 3.8 g to about 4 g per day of ethyl eicosapentaenoate is administered to the subject.

6. The method of claim 1, wherein the pharmaceutical composition is administered to the subject daily for a period of 1 to about 12 weeks.

7. The method of claim 1, wherein the reduction in APOC3 level is in comparison to control subjects having fasting triglycerides of about 200 mg/dl to about 499 mg/dl who have received the statin but not the pharmaceutical composition.

8. The method of claim 1, wherein the pharmaceutical composition comprises at least about 95%, by weight of all fatty acids present, ethyl eicosapentaenoate.

9. The method of claim 1, wherein the pharmaceutical composition comprises no more than about 10%, by weight of all fatty acids present, docosahexaenoic acid or a derivative thereof, if any.

10. The method of claim 1, wherein the pharmaceutical composition comprises at least about 95%, by weight of all fatty acids present, ethyl eicosapentaenoate and no more than about 2%, by weight of all fatty acids present, docosahexaenoic acid or a derivative thereof, if any.

11. A method of reducing an apolipoprotein C-III (APOC3) level of a subject having fasting baseline triglycerides of at least about 500 mg/dl, the method comprising administering to the subject a pharmaceutical composition comprising about 1 g to about 4 g of ethyl eicosapentaenoate per day,
   wherein the subject is on a high statin efficacy regimen selected from the group consisting of about 20 to about 40 mg rosuvastatin, about 40 to about 80 mg atorvastatin, about 80 mg simvastatin, and about 40 to about 80 mg simvastatin plus about 5 to about 10 mg ezetimibe or the subject is on a medium statin efficacy regimen selected from the group consisting of about 5 to about 10 mg rosuvastatin, about 10 to about 20 mg atorvastatin, about 20 to about 40 mg simvastatin, and about 10 to about 20 mg simvastatin plus about 5 to about 10 mg ezetimibe.

12. The method of claim 11, wherein the APOC3 level is reduced by at least about 5%.

13. The method of claim 11, wherein the APOC3 level is reduced by at least about 25%.

14. The method of claim 11, wherein about 2 g per day of ethyl eicosapentaenoate is administered to the subject.

15. The method of claim 11, wherein about 3.8 g to about 4 g per day of ethyl eicosapentaenoate is administered to the subject.

16. The method of claim 11, wherein the pharmaceutical composition is administered to the subject daily for a period of 1 to about 12 weeks.

17. The method of claim 11, wherein the reduction in APOC3 level is in comparison to control subjects having fasting triglycerides of at least about 500 mg/dl who have not received the pharmaceutical composition.

18. The method of claim 11, wherein the pharmaceutical composition comprises at least about 95%, by weight of all fatty acids present, ethyl eicosapentaenoate.

19. The method of claim 11, wherein the pharmaceutical composition comprises no more than about 10%, by weight of all fatty acids present, docosahexaenoic acid or a derivative thereof, if any.

20. The method of claim 11, wherein the pharmaceutical composition comprises at least about 95%, by weight of all fatty acids present, ethyl eicosapentaenoate and no more than about 2%, by weight of all fatty acids present, docosahexaenoic acid or a derivative thereof, if any.

* * * * *